(12) United States Patent
Frederick et al.

(10) Patent No.: US 9,168,247 B2
(45) Date of Patent: Oct. 27, 2015

(54) BETA CARBOLINE DERIVATIVES USEFUL IN THE TREATMENT OF PROLIFERATIVE DISORDERS

(75) Inventors: Raphael Frederick, Godinne (BE); Bernard Masereel, Fize-Fontaine (BE); Jeremy Reniers, Biercee (BE); Johan Wouters, Beez (BE); Celine Bruyere, Forest (BE); Robert Kiss, Sint-Pieters-Leeuw (BE); Céline Anne Marie Michelle Meinguet, Ciney (BE); Véronique Emmanuelle Julie Mathieu, Brussels (BE)

(73) Assignees: FACULTES UNIVERSITAIRES NOTRE DAME DE LA PAIX, Namur (BE); UNIVERSITE LIBRE BRUXELLES, Brussels (BE)

( * ) Notice: Subject to any disclaimer, the term of this patent is extended or adjusted under 35 U.S.C. 154(b) by 0 days.

(21) Appl. No.: 13/704,109

(22) PCT Filed: Jun. 24, 2011

(86) PCT No.: PCT/EP2011/060658
§ 371 (c)(1),
(2), (4) Date: Dec. 13, 2012

(87) PCT Pub. No.: WO2011/161256
PCT Pub. Date: Dec. 29, 2011

(65) Prior Publication Data
US 2013/0116273 A1 May 9, 2013
US 2014/0005220 A9 Jan. 2, 2014

Related U.S. Application Data

(60) Provisional application No. 61/358,609, filed on Jun. 25, 2010.

(30) Foreign Application Priority Data

Jun. 25, 2010 (WO) .................. PCT/EP2010/059083

(51) Int. Cl.
*A61K 31/437* (2006.01)
*C07D 471/04* (2006.01)

(52) U.S. Cl.
CPC ............ *A61K 31/437* (2013.01); *C07D 471/04* (2013.01)

(58) Field of Classification Search
None
See application file for complete search history.

(56) References Cited

U.S. PATENT DOCUMENTS

2009/0227619 A1  9/2009  Wu et al.

FOREIGN PATENT DOCUMENTS

| CN | 101139347 | 10/2007 |
|---|---|---|
| CN | 101429198 | 11/2007 |
| DE | 198 07 993 | 9/1999 |
| GB | 2 447 791 | 9/2008 |
| JP | 2003-527394 | 9/2003 |
| JP | 2006-526580 | 11/2006 |
| JP | 2012-051804 A | 3/2012 |
| WO | WO 01/68648 | 9/2001 |
| WO | WO 2008/157358 | 12/2008 |
| WO | WO 2009/047298 | 4/2009 |
| WO | WO 2010/015636 | 2/2010 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface).*
Jordan, V. C. (Nature Reviews: Drug Discovery, 2, 2003, 205-213).*
SciFinder record of Abu-Shady reference (Preparation of Harmol Derivatives, Bulletin of the Faculty of Pharmacy (Cairo University), vol. 9; Issue 1, date 1971).*
Cao, et al. "Design, Synthesis, and 3D-QSAR of β-carboline Derivatives as Potent Antitumor Agents," *European Journal of Medicinal Chemistry*, vol. 45, No. 6, pp. 2503-2515, Jun. 1, 2010.

(Continued)

*Primary Examiner* — Jeffrey S Lundgren
*Assistant Examiner* — William Lee
(74) *Attorney, Agent, or Firm* — Knobbe Martens Olson & Bear LLP

(57) ABSTRACT

The invention provides novel beta-carboline derivatives of formulae (Ia) and (Ib) useful in the treatment of proliferative disorders including cancer, intermediates used in their preparation, processes for preparing the same and uses thereof.

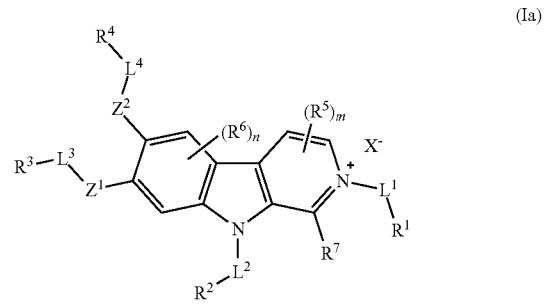

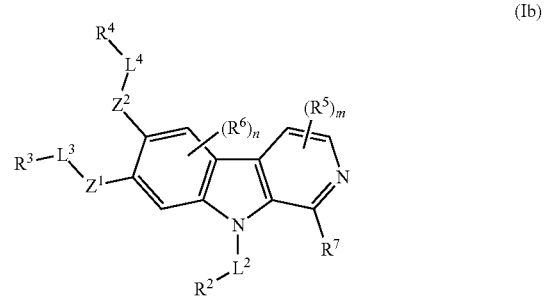

17 Claims, 3 Drawing Sheets

(56) References Cited

OTHER PUBLICATIONS

Database CA [Online], Chemical Abstracts Service, Begum, et al., "Synthesis and Antimycobacterial Activity of Some β-carboline Alkaloids," retrieved from STN Database accession No. 2004:536160 abstract, 2004.
Reniers, et al. "Synthesis and Evaluation of β-carboline Derivatives as Potential Monoamine Oxidase Inhibitors," *Bioorganic & Medicinal Chemistry*, vol. 19, No. 1, pp. 134-144, Jan. 1, 2011.
Song, et al. "β-Carbolines as Specific Inhibitors of Cyclin-dependent Kinases," *Bioorganic & Medicinal Chemistry Letters*, vol. 12, No. 7, pp. 1129-1132, Apr. 8, 2002.
Zhang, et al. "DH166, a Beta-carboline Derivative, Inhibits the Kinase Activity of PLK1," *Cancer Biology & Therapy*, vol. 8, No. 24, pp. 2374-2383, Dec. 15, 2009.
International Search Report dated Sep. 2, 2011 issued to priority international application No. PCT/EP2011/060658.
Ishida, et al. "Antitumor Agents 201. Cytotoxicity of Harmine and β-carboline Analogs," *Bioorganic & Medicinal Chemistry Letters* 9, pp. 3319-3324, 1999.
Basler, et al. "Effets de la dihydroflavopereirine et de la sempervirine sur des cellules cancereuses en culture" Annales Pharmaceutiques Françaises, 1985, 43(1), 83-88.
Cao, R., et al. "Design, synthesis and in vitro and in vivo antitumor activities of novel β-carboline derivatives." European Journal of Medicinal Chemistry 40.10 (2005): 991-1001.
Cao, Rihui, et al. "Synthesis, acute toxicities, and antitumor effects of novel 9-substituted β-carboline derivatives." Bioorganic & Medicinal Chemistry 12.17 (2004): 4613-4623.
Castro, Alfredo C., et al. "Novel IKK inhibitors: β-carbolines." Bioorganic & medicinal chemistry letters 13.14 (2003): 2419-2422.
Ishida J et al, Antitumor Agents 201. Cytotoxicity of Harmine and beta-Carboline Analogs—Bioorganic & Medicinal Chemistry Letters, Pergamon, Amsterdam, NL, vol. 9, No. 23, pp. 3319-3324, Jun. 12, 1999.
Rashid, et al. "New Cytotoxic N-Methylated β-Carboline Alkaloids from the Marine Ascidian Eudistoma g ilboverde." Journal of Natural Products 64.11 (2001): 1454-1456.
Wieczorek, J., et al. "Antineoplastic activity of azacarbazoles. I. Synthesis and antitumor properties of alpha-carboline and its selected derivatives." Archivum immunologiae et therapiae experimentalis 34.3 (1986): 315-321.

* cited by examiner

BETA CARBOLINE DERIVATIVES USEFUL IN THE TREATMENT OF PROLIFERATIVE DISORDERS

CROSS-REFERENCE TO RELATED APPLICATIONS

This application is the U.S. National Phase under 35 U.S.C §371 of International Application PCT/EP2011/060658, filed Jun. 24, 2011, which claims priority to U.S. Provisional Application No. 61/358,609, filed Jun. 25, 2010, and PCT/EP2010/059083, filed Jun. 25, 2010.

FIELD OF THE INVENTION

The invention is in the medical field, more precisely in the field of new therapeutic compounds, more particularly compounds useful in the treatment of proliferative disorders including cancer. The invention relates to alkaloid compounds, more specifically to beta-carboline derivatives, intermediates used in their preparation, processes for preparing the same and uses thereof.

BACKGROUND OF THE INVENTION

The search for novel anti-cancer drugs is a never ending story, since cancer is becoming a more and more important cause of death amongst humans. More than 80% of all anti-cancer drugs are directed towards the apoptosis pathway of tumour cells and are cytotoxic upon activating said pathway.

A large number of cancer cells such as glioblastomas (brain cancers), brain metastases, melanomas, pancreatic cancers, lung cancers of the NSCLC-type, refractory prostate cancers (HRPC), breast cancers such as triple negatives and other types are naturally resistant to apoptosis and cannot be treated by the many known drugs and chemotherapeutics. Development of new compounds having cytotoxic and/or cytostatic effects in tumour or cancer cells, and particularly in tumour or cancer cells which are resistant to apoptosis, is of considerable importance.

A naturally-occurring beta carboline, harmine, has been previously isolated from plants such as the Middle Eastern plant harmal or Syrian rue (*Peganum harmala*) and the South American vine (*Banisteriopsis caapi*) and shown to exhibit anti-cancer properties. However, previous reports demonstrated that harmine and its derivatives caused remarkable acute neurotoxicity characterized by tremble, twitch, and jumping in experimental mice model. Results of investigation on the in vitro anti-tumour activity of harmine and certain of its derivatives showed that these compounds had significant inhibition effect on several cultured tumour cell lines, such as HeLa cells (cervical carcinoma), S-180 cells (sarcoma), BEL-7402 cells (hepatoma), MGC-803 cells (gastric carcinoma), CNE2 cells (nasopharyngeal carcinoma), MA782/5S cells (breast cancer) and K562 cells (leucocythemia) (Wu, US 20090227619). EP 0357122 showed cytostatic properties of certain beta-carbolines.

Moreover, harmine and certain of its derivatives exhibited DNA intercalation capacity and topoisomerase I inhibition, which was related to their anti-tumour activity (Cao et al., 2005, Biochem. Biophys. Res. Com. 338: 1557-63).

Additionally, harmine was repeatedly shown to inhibit the protein kinase DYRK1A (Göckler, 2009, FEBS J. 276(21): 6324-37; Seifert, 2008, FEBS J. 275(24): 6268-80; Bain et al., 2007, Biochem J 408: 297-315). Over-expression of the DYRK1A kinase (dual specificity tyrosine-phosphorylated and regulated kinase 1a) has been implicated in multiple diseases or disorders or syndromes prominently including cancer, tumorigenesis and uncontrolled cell proliferation (Laguna et al., 2008, Dev Cell. 15(6): 841-53), but also Alzheimer disease, Pick disease (Ferrer et al., 2005, Neurobiol Dis. 20(2): 392-400) and Down Syndrome (Lepagnol-Bestel et al., 2009, Hum Mol Genet. 18(8): 1405-14).

Moreover, caspase-9 is a substrate of DYRK1A: inhibition of DYRK1A, by, e.g., harmine, induces the activation of caspase-9 and leads to massive apoptosis in different human cell types (Seifert et al., supra). It was also shown that melanomas are intrinsically resistant to pro-apoptosis stimuli and over-express DYRK1A (de Wit et al., 2002, Melanoma Res 12: 57-69). Recently, it was shown that harmine could reverse resistance to anticancer drugs by inhibiting BCRP (Ma et al., 2010, Phytother. Res. 24(1): 146-9).

There is therefore a continuous need in the art for identifying novel anti-proliferative drugs and for improving the efficacy of existing anti-proliferative treatments by combining the latter with novel anti-proliferative drugs.

SUMMARY OF THE INVENTION

The invention addresses the problems of the art by providing novel beta carboline derivative compounds showing anti-tumour and anti-cancer activity and useful in the treatment of proliferative disorders.

In particular, as set out in the experimental section the inventors devised a chemical synthesis process allowing to generate the present novel beta carboline derivatives suitably mono-, di-, tri- or tetra-substituted at positions 2, 6, 7 and/or 9 of the beta carboline ring system.

The anti-proliferative effects of the present compounds were evaluated by means of the colorimetric MTT assay in several human cancer cell-lines including a) U373, T98G and Hs683 glioblastoma cells, and b) OE21 and OE33 oesophageal cancer cells. It was unexpectedly found that the compounds had important cytostatic and/or anti-cancer effects which were not correlated with the compounds' ability to inhibit the protein kinase DYRK1A, a known and prominent target for beta-carbolines such as harmine Whereas the compounds showed mean anti-proliferative effect on glioma cell lines in the low micromolar range, some highly effective compounds denoted herein as CV18, CV23, CV24 and CV26 displayed mean anti-proliferative effect on the glioma cell lines in the submicromolar range (e.g., as low as 0.34 to 0.8 µM).

Even more promisingly, the inventors found that the present compounds exerted their effect via a non-apoptosis-related mechanism, which makes them particularly good candidates as anti-proliferative drugs for treating apoptosis-resistant tumours or cancers and for reducing or overcoming problems linked to known anti-cancer drugs, such as acquisition of resistance, non-specific cytotoxicity, etc.

It is thus an object of the invention to provide novel compounds useful for treating proliferative disorders including tumours and cancers, as well as to provide pharmaceutical compositions comprising said compounds and therapeutic uses and methods employing the compounds and pharmaceutical compositions in the treatment of proliferative disorders. Another object of the invention is to provide processes for preparing the present compounds and, more generally, processes for preparing carboline derivatives mono-, di-, tri- or tetra-substituted at positions 2, 6, 7 and/or 9 of the beta carboline ring system.

Accordingly, in an aspect the invention provides a compound of any one of Formulas (Ia) or (Ib), or stereoisomeric forms thereof,

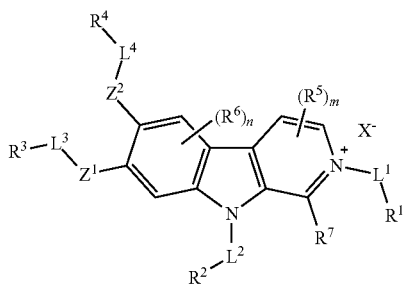

(Ia)

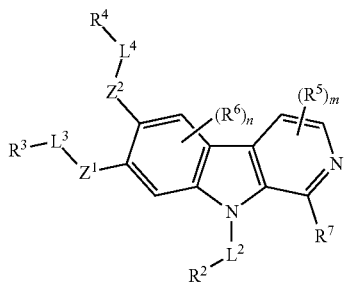

(Ib)

wherein m is an integer selected from 0, 1 or 2;

n is an integer selected from 0, 1 or 2;

$L^1$ is a direct bond, —O—, —S—, —$NR^8$— or —($CR^{9a}R^{9b})_p$—; and $R^8$ is hydrogen or $C_{1-6}$alkyl; and p is an integer selected from 1, 2, 3, 4, 5 or 6; and each $R^{9a}$ and $R^{9b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;

$L^2$ is a direct bond, —O—, —S—, —$NR^{10}$— or —($CR^{11a}R^{11b})_q$—; and $R^{10}$ is hydrogen or $C_{1-6}$alkyl; and q is an integer selected from 1, 2, 3, 4, 5 or 6; and each $R^{11a}$ and $R^{11b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;

$Z^1$ is a direct bond, —O—, —S— or —$NR^{12}$; and $R^{12}$ is hydrogen or $C_{1-6}$alkyl;

$L^3$ is a direct bond or —($CR^{13a}R^{13b})_r$—; and r is an integer selected from 1, 2, 3, 4, 5 or 6; and each $R^{13a}$ and $R^{13b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;

$Z^2$ is a direct bond, —O—, —S— or —$NR^{14}$; and $R^{14}$ is hydrogen or $C_{1-6}$alkyl;

$L^4$ is a direct bond or —($CR^{15a}R^{15b})_s$—; and s is an integer selected from 1, 2, 3, 4, 5 or 6; and each $R^{15a}$ and $R^{15b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;

$R^1$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl; heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo; preferably $R^1$ is hydrogen, $C_{1-8}$alkyl, $C_{2-8}$alkenyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl; heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo or $R^1$ is hydrogen, $C_{1-8}$alkyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl; heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo; more preferably $R^1$ is hydrogen, $C_{1-8}$alkyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl; heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo;

$R^2$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; preferably R$^2$ is hydrogen, C$_{1-8}$alkyl, C$_{2-8}$alkenyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo or R$^2$ is hydrogen, C$_{1-8}$alkyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; more preferably R$^2$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo R$^3$ is hydrogen, C$_{1-8}$alkyl, C$_{2-8}$alkenyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; preferably R$^3$ is hydrogen, C$_{1-8}$alkyl, C$_{2-8}$alkenyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo or R$^3$ is hydrogen, C$_{1-8}$alkyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; more preferably R$^3$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo;

R$^4$ is hydrogen, C$_{1-8}$alkyl, C$_{2-8}$alkenyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; preferably R$^4$ is hydrogen, C$_{1-8}$alkyl, C$_{2-8}$alkenyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo or R$^4$ is hydrogen, C$_{1-8}$alkyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; more preferably R$^4$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo;

with the proviso that in formula Ia at least one of R$^1$-L$^1$-, R$^2$-L$^2$-, R$^3$-L$^4$-Z$^1$- or R$^4$-L$^4$-Z$^2$— is not hydrogen and in formula Ib at least one of R$^2$-L$^2$-, R$^3$-L$^3$-Z$^1$— or R$^4$-L$^4$-Z$^2$— is not hydrogen;

R$^7$ is hydrogen, C$_{1-6}$alkyl or C$_{1-6}$alkyloxy, optionally substituted with one or more substituents independently selected from halo, hydroxy, C$_{1-4}$alkyloxy, aryl or oxo;

R$^5$ is halo, C$_{1-6}$alkyl, C$_{1-6}$alkyloxy, haloC$_{1-6}$alkyl or haloC$_{1-6}$alkyloxy;

R$^6$ is halo, C$_{1-6}$alkyl, C$_{1-6}$alkyloxy, haloC$_{1-6}$alkyl or haloC$_{1-6}$alkyloxy;

X$^-$ is an organic or inorganic anion;

or pharmaceutically acceptable addition salts, hydrates or solvates thereof.

Also disclosed are methods for the preparation of compounds of the general Formulas (Ia) or (Ib), the stereoisomeric forms thereof or the pharmaceutically acceptable addition salts, hydrates or solvates thereof, as well as intermediates used in said methods.

Another aspect provides the compound according to the general Formulas (Ia) or (Ib), the stereoisomeric forms thereof or the pharmaceutically acceptable addition salts, hydrates or solvates thereof, for use as a medicament, preferably for use in the treatment of a proliferative disorder.

Another aspect provides the compound according to the general Formulas (Ia) or (Ib), the stereoisomeric forms thereof or the pharmaceutically acceptable addition salts, hydrates or solvates thereof, for inducing cell cycle arrest in a subject, particularly in the course of the treatment of a proliferative disorder in said subject.

Also disclosed is the use of the compound according to the general Formulas (Ia) or (Ib), the stereoisomeric forms thereof or the pharmaceutically acceptable addition salts, hydrates or solvates thereof, for the manufacture of a medicament for the treatment of a proliferative disorder.

Also disclosed is the use of the compound according to the general Formulas (Ia) or (Ib), the stereoisomeric forms thereof or the pharmaceutically acceptable addition salts, hydrates or solvates thereof, for the manufacture of a medicament for inducing cell cycle arrest in a subject, particularly in the course of the treatment of a proliferative disorder in said subject.

A further aspect provides a method for treating a proliferative disorder in a subject in need of such treatment, comprising administering to said subject a therapeutically effective amount of the compound according to the general Formulas (Ia) or (Ib), the stereoisomeric forms thereof or the pharmaceutically acceptable addition salts, hydrates or solvates thereof.

A further aspect provides a method for inducing cell cycle arrest in a subject, particularly in the course of the treatment of a proliferative disorder in a subject in need of such treatment, comprising administering to said subject a therapeutically effective amount of the compound according to the general Formulas (Ia) or (Ib), the stereoisomeric forms thereof or the pharmaceutically acceptable addition salts, hydrates or solvates thereof.

A further aspect provides a method for inducing cell cycle arrest in vitro, comprising administering to proliferating cells in vitro the compound according to the general Formulas (Ia) or (Ib), the stereoisomeric forms thereof or the pharmaceutically acceptable addition salts, hydrates or solvates thereof, in an amount effective to induce cell cycle arrest in said cells.

A further aspect discloses a pharmaceutical composition comprising the compound according to the general Formulas (Ia) or (Ib), the stereoisomeric forms thereof or the pharmaceutically acceptable addition salts, hydrates or solvates thereof, and one or more pharmaceutically acceptable excipients. Also disclosed is a method for producing the pharmaceutical composition comprising admixing the compound according to the general Formulas (Ia) or (Ib), the stereoisomeric forms thereof or the pharmaceutically acceptable addition salts, hydrates or solvates thereof, with the one or more pharmaceutically acceptable excipients.

Another aspect provides a kit of parts comprising (a) the compound according to the general Formulas (Ia) or (Ib), the stereoisomeric forms thereof or the pharmaceutically acceptable addition salts, hydrates or solvates thereof and/or (b) the pharmaceutical composition, and further comprising (c) at least one other pharmaceutically or biologically active ingredient.

The kit of parts may be configured for separate, simultaneous or sequential in any order administration of its constituents (a) and/or (b) and (c). The constituents (a) and/or (b) and the constituent (c) in said kit may be admixed or may be separate, particularly may be separate such as for example contained in separate containers. Disclosed is as well a method for producing said kit of parts comprising including the constituents (a) and/or (b) and (c) in a kit of parts.

Another aspect provides said pharmaceutical composition for use as a medicament, preferably for use in the treatment of a proliferative disorder.

Also disclosed is a method for treating a proliferative disorder in a subject in need of such treatment, comprising administering to said subject a therapeutically effective amount of said pharmaceutical composition.

A proliferative disorder as intended herein may particularly but without limitation include neoplasm and cancers, dysplasia, premalignant or precancerous lesions, abnormal cell growths, benign tumours, malignant tumours, cancer or metastasis, wherein the cancer is selected from the group of: leukaemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, haematological cancer and lymphoma.

Preferably, the cancer may be selected from the group of: leukaemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, haematological cancer and lymphoma.

Preferably, the cancer may be selected from the group of: non-small cell lung cancer, prostate cancer (more preferably refractory prostate cancer), breast cancer (preferably triple-negative breast cancer, i.e., breast cancer not expressing oestrogen receptor (ER), progesterone receptor (PR) and Her2/neu), glioma preferably glioblastoma, colon cancer and melanoma.

Preferably, the proliferative disorder such as cancer is an apoptosis-resistant tumour or cancer.

The above and additional aspects, preferred embodiments and features of the invention are described in the following sections and in the appended claims. Each aspect or embodiment described herein may be combined with any other aspect(s) or embodiment(s) unless clearly indicated to the contrary. In particular, any feature indicated as being preferred or advantageous may be combined with any other feature or features indicated as being preferred or advantageous. The subject matter of appended claims 1 to 20 is hereby specifically incorporated in this specification.

DETAILED DESCRIPTION OF THE INVENTION

Figure 1A:
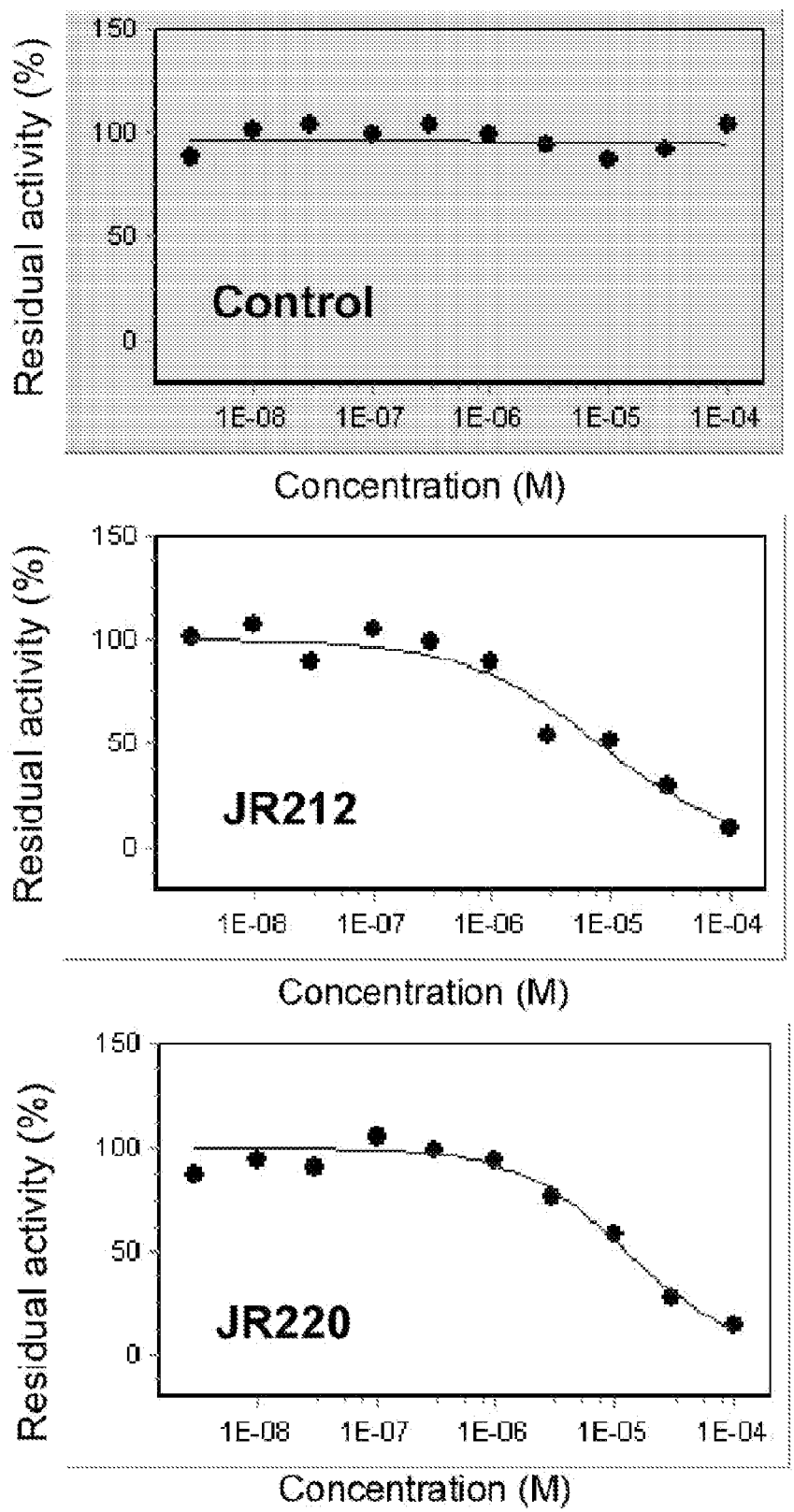
FIG. 1A-C: Kinase inhibition activity with JR212, JR220, JR84, CV12, CV24, JR95 was tested on dyrk1a protein kinase. This FIGURE illustrates the inhibition of dyrk1A by concentrations of the compounds of the invention ranging from about $5.10^{-5}$ M to about $1.5 \times 10^{-9}$ M ($_{33}$Pan Qinase® Activity Assay). The Residual Activity was calculated by using the formula: Res Activity (%)=100×[(cpm of compound–"low control")/("high control"–"low control")].

As used herein, the singular forms "a", "an", and "the" include both singular and plural referents unless the context clearly dictates otherwise. By way of example, "a compound" means one compound or more than one compound.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The term "about" as used herein when referring to a measurable value such as a parameter, an amount, a temporal duration, and the like, is meant to encompass variations of and from the specified value, in particular variations of +/−20% or less, preferably +/−10% or less, more preferably +/−5% or less, even more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present disclosure are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, definitions of terms may be included to better appreciate the teaching of the present invention, and the terms used may be preferably construed in accordance with the respective definitions, unless a context dictates otherwise.

The term "substituted" denotes that one or more hydrogens on one or more atoms (typically C, N, O or S atoms, usually C atoms) of a group indicated by the modifier "substituted" is replaced with a selection from the recited group, provided that the normal valency of the atoms of the indicated group is not exceeded, and that the substitution results in a chemically stable compound, i.e., a compound that is sufficiently robust to survive isolation to a useful degree of purity from a reaction mixture, and formulation into an useful agent. The term "one or more" covers the possibility of one, more or all available atoms of an indicated group to be substituted where appropriate; preferably of one, two or three, more preferably of one or two, and even more preferably of one available atoms of an indicated group to be substituted. When any variable, e.g., halogen or alkyl, occurs more than one time in any constituent or group, each definition is independent.

The term "halo" or "halogen" as a group or part of a group is generic for fluoro, chloro, bromo and iodo, and may particularly preferably refer to fluoro, chloro or bromo, even more preferably to fluoro.

The terms "$C_{1-8}$alkyl", "$C_{1-6}$alkyl", "$C_{1-4}$alkyl" or "$C_{1-2}$alkyl" as a group or part of a group refer to a hydrocarbyl radicals of Formula $C_nH_{2n+1}$ wherein n is a number ranging from 1 to 8, or from 1 to 6, or from 1 to 4 or from 1 to 2, respectively. Generally, alkyl groups as intended herein comprise from 1 to 8 carbon atoms, preferably 1 to 6 carbon atoms, more preferably from 1 to 4 carbon atoms, even more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, such as for example methyl, ethyl, n-propyl, i-propyl, 2-methyl-ethyl, butyl and its isomers (e.g. n-butyl, i-butyl and tert-butyl); pentyl and its isomers, hexyl and its isomers, and the like.

The term "$C_{2-8}$alkenyl" by itself or as part of another substituent, refers to an unsaturated hydrocarbyl group, which may be linear, or branched, comprising one or more carbon-carbon double bonds. Preferred alkenyl groups thus comprise between 2 and 8 carbon atoms, preferably between 2 and 4 carbon atoms. Non-limiting examples of $C_{2-8}$alkenyl groups include ethenyl, 2-propenyl, 2-butenyl, 3-butenyl, 2-pentenyl and its chain isomers, 2-hexenyl and its chain isomers, 2,4-pentadienyl and the like.

The term "$C_{2-8}$alkynyl" by itself or as part of another substituent, refers to an unsaturated hydrocarbyl group, which may be linear, or branched, comprising one or more carbon-carbon triple bonds. Preferred alkynyl groups thus comprise between 2 and 8 carbon atoms, preferably between 2 and 4 carbon atoms. Non limiting examples of $C_{2-8}$alkynyl groups include ethynyl, 2-propynyl, 2-butyryl, 3-butynyl, 2-pentynyl and its chain isomers, 2-hexynyl and its chain isomers and the like.

The terms "$C_{1-8}$alkyloxy", "$C_{1-6}$alkyloxy" or "$C_{1-4}$alkyloxy" as a group or part of a group refer to a radical having the Formula $—OR^a$ wherein $R^a$ is $C_{1-8}$alkyl, $C_{1-6}$alkyl or $C_{1-4}$alkyl, respectively, as defined herein. Non-limiting examples of suitable alkyloxy include methyloxy, ethyloxy, propyloxy, isopropyloxy, butyloxy, isobutyloxy, sec-butyloxy, tert-butyloxy, pentyloxy and hexyloxy.

The terms "$C_{1-8}$alkylthio", "$C_{1-6}$alkylthio" or "$C_{1-4}$alkylthio" as a group or part of a group refer to a radical having the Formula $—SR^b$ wherein $R^b$ is $C_{1-8}$alkyl, $C_{1-6}$alkyl or $C_{1-4}$alkyl, respectively, as defined herein. Non-limiting examples of suitable alkylthio include methylthio, ethylthio, propylthio, isopropylthio, butylthio, isobutylthio, sec-butylthio, tert-butylthio, pentylthio and hexylthio.

The terms "$C_{1-8}$alkylamino", "$C_{1-6}$alkylamino" or "$C_{1-4}$alkylamino" alone or as part of another group mean a secondary or tertiary amino radical, wherein a hydrogen atom of the amino radical is replaced with $C_{1-8}$alkyl, $C_{1-6}$alkyl or $C_{1-4}$alkyl, respectively, as defined herein. Specifically included are secondary alkylamino radicals of the formula —NHalkyl. Examples of secondary alkylamino radicals include methylamino (—NHCH$_3$), ethylamino (—NHCH$_2$CH$_3$), n-propylamino, isopropylamino, n-butylamino, isobutylamino, sec-butylamino, tert-butylamino, n-hexylamino, and the like. Specifically included are also tertiary alkylamino radicals, such as dialkylamino radicals of the formula —N(alkyl)(alkyl), wherein the alkyl moieties may be the same or different. Examples of dialkylamino radicals include dimethylamino (—N(CH$_3$)CH$_3$), methyl-ethylamino (—N(CH$_2$CH$_3$)CH$_3$), and the like.

Hydroxy denotes —OH, oxo denotes =O, nitro denotes —NO$_2$, and cyano denotes —CN.

The term "cycloalkyl" as a group or part of a group refers to a saturated or partially unsaturated hydrocarbyl radical having 1 or 2 cyclic structures. Specifically, cycloalkyl denotes all saturated hydrocarbon groups containing 1 (i.e., monocyclic) to 2 (i.e., bicyclic) rings. Cycloalkyl groups may comprise 3 or more carbon atoms in a ring and preferably comprise from 3 to 10 carbon atoms, more preferably from 3 to 8 carbon atoms, still more preferably from 3 to 6 carbon atoms in a ring. Specifically, the term "$C_{3-8}$cycloalkyl" as a group or part of a group refers to monocyclic or bicyclic cycloalkyl groups, preferably to monocyclic cycloalkyl groups, comprising independently from 3 to 8 carbon atoms in each ring. The further rings of multi-ring cycloalkyl radicals may be either fused, bridged and/or joined through one or more spiro atoms. Examples of monocyclic cycloalkyl radicals include cyclopropyl, cyclobutyl, cyclopentyl, cyclohexyl, cycloheptyl, cyclooctyl and the like. Examples of polycyclic cycloalkyl radicals include decahydronaphthyl, bicyclo[5.4.0]undecyl, adamantyl, and the like.

The term "aryl" as a group or part of a group refers to a polyunsaturated, aromatic hydrocarbyl group comprising a single aromatic ring (e.g., phenyl) or multiple (e.g., two, three or four) aromatic rings fused together (e.g., naphthyl) or linked covalently (e.g., biphenyl), typically containing 5 to 12 carbon atoms, preferably 6 to 10 carbon atoms in a ring. An aromatic ring in an aryl group may optionally include one or two additional rings (cycloalkyl, heterocyclyl and/or heteroaryl) fused thereto. Non-limiting examples of aryl comprise phenyl, biphenylyl, 5- or 6-tetralinyl, 1-, 2-, 3-, 4-, 5-, 6-, 7- or 8-azulenyl, naphthalen-1- or -2-yl, 4-, 5-, 6 or 7-indenyl, 1-, 2-, 3-, 4- or 5-acenaphtylenyl, 3-, 4- or 5-acenaphtenyl, 1-, 2-, 3-, 4- or 10-phenanthryl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "heterocyclyl" as a group or part of a group refers to non-aromatic, fully saturated or partially unsaturated cyclic groups (e.g., 3 to 7 member monocyclic groups, preferably 5 or 6 member monocyclic groups, or 7 to 11 member bicyclic groups, or groups containing a total of 3 to 10 ring atoms) which comprise at least one heteroatom in at least one carbon atom-containing ring. Each ring of a heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

Where a carbon atom in an aryl group is replaced with a heteroatom, the resultant ring is referred to herein as a heteroaryl ring.

The term "heteroaryl" as a group or part of a group refers to but is not limited to 5 to 12 carbon-atom aromatic rings or ring systems containing 1 to 2 rings which are fused together or linked covalently, typically containing 5 to 6 atoms; at least one of which is aromatic in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "direct bond" refers to a single covalent bond.

It will be appreciated that some of the compounds described herein and their pharmaceutically acceptable addition salts may contain one or more centers of chirality and may exist as stereoisomeric forms.

The term "stereoisomeric forms" as used hereinbefore defines all the possible isomeric forms that the compounds described herein may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds described herein are embraced within the scope of this invention.

For therapeutic use, salts of the compounds described herein are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The term "pharmaceutically acceptable" as generally used herein, inter alia in connection with salts and excipients, is consistent with the art and means compatible with the other ingredients of a pharmaceutical composition and not deleterious to the recipient thereof.

The pharmaceutically acceptable acid and base addition salts as mentioned hereinabove or hereinafter are meant to comprise the therapeutically active non-toxic acid and base addition salt forms which the compounds as described herein are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds as described herein containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, aluminum salts, zinc salts, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds as described herein are able to form, as well as the salts thereof. Examples of such forms are, e.g., hydrates, alcoholates and the like.

Throughout this specification, any compound described herein is inherently intended to comprise all isotopic combinations of its chemical elements. Throughout this specification, a chemical element, in particular when mentioned in relation to a compound as described herein, comprises all isotopes and isotopic mixtures of this element. For example, when hydrogen is mentioned, it is understood to refer to $^{1}$H, $^{2}$H, $^{3}$H and mixtures thereof.

Any compound as described herein therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound as described herein, or a pharmaceutically acceptable salt thereof, which contains at least one radioactive atom. For example, a compound can be labelled with positron or with gamma emitting radioactive isotopes. For radioligand-binding techniques, the $^{3}$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^{3}$H, $^{11}$C, $^{18}$F, $^{122}$I, $^{123}$I, $^{125}$I, $^{131}$I, $^{75}$Br, $^{76}$Br, $^{77}$Br and $^{82}$Br.

Preferred features of the compounds described herein of this invention are now set forth.

Disclosed herein is a compound of any one of Formulas (Ia) or (Ib), and any subgroup thereof, or stereoisomeric forms thereof,

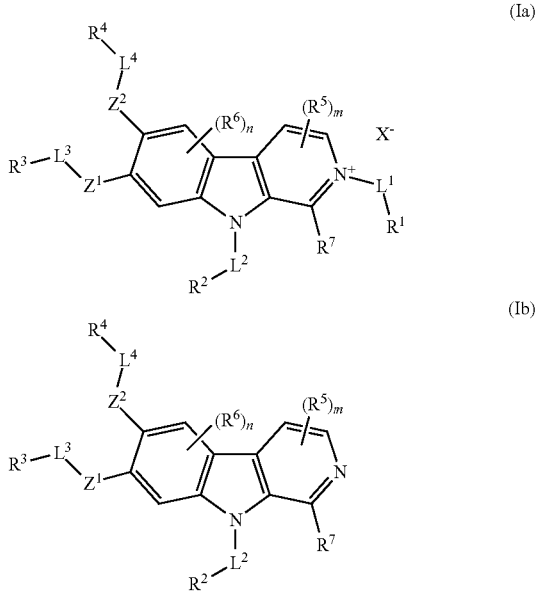

wherein m is an integer selected from 0, 1 or 2; preferably m is 0 or 1; more preferably m is 0;

n is an integer selected from 0, 1 or 2; preferably n is 0 or 1; more preferably n is 0;

$L^1$ is a direct bond, —O—, —S—, —$NR^8$— or —($CR^{9a}R^{9b}$)$_p$—; and $R^8$ is hydrogen or $C_{1-6}$alkyl, preferably hydrogen; preferably $L^1$ is —($CR^{9a}R^{9b}$)$_p$—; and p is an integer selected from 1, 2, 3, 4, 5 or 6; preferably p is 1, 2 or 3; more preferably p is 1 or 2; even more preferably p is 1; and each $R^{9a}$ and $R^{9b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo, preferably selected from halo; preferably each $R^{9a}$ and $R^{9b}$ is independently hydrogen, $C_{1-6}$alkyl, $C_{1-6}$alkyloxy, hydroxy or halo, each group being optionally substituted with one or more substituents independently selected from halo, hydroxy, $C_{1-4}$alkyloxy or oxo, preferably selected from halo; more preferably each $R^{9a}$ and $R^{9b}$ is hydrogen; equally preferably $L^1$ is a direct bond;

$L^2$ is a direct bond, —O—, —S—, —$NR^{10}$— or —($CR^{11a}R^{11b}$)$_q$—; and $R^{10}$ is hydrogen or $C_{1-6}$alkyl, preferably hydrogen; preferably $L^2$ is a direct bond or —($CR^{11a}R^{11b}$)$_q$—; and q is an integer selected from 1, 2, 3, 4, 5 or 6; preferably q is 1, 2 or 3; more preferably q is 1 or 2; even more preferably q is 1; and each $R^{11a}$ and $R^{11b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo, preferably selected from halo; preferably each $R^{11a}$ and $R^{11b}$ is independently hydrogen, $C_{1-6}$alkyl, $C_{1-6}$alkyloxy, hydroxy or halo, each group being optionally substituted with one or more substituents independently selected from halo, hydroxy, $C_{1-4}$alkyloxy or oxo, preferably selected from halo; more preferably each $R^{11a}$ and $R^{11b}$ is hydrogen; equally preferably $L^2$ is a direct bond;

$Z^1$ is a direct bond, —O—, —S— or —$NR^{12}$; and $R^{12}$ is hydrogen or $C_{1-6}$alkyl, preferably hydrogen; more preferably $Z^1$ is —O— or —S—; most preferably $Z^1$ is —O—;

$L^3$ is a direct bond or —($CR^{13a}R^{13b}$)$_r$—; and r is an integer selected from 1, 2, 3, 4, 5 or 6; preferably r is 1, 2 or 3; more preferably r is 1 or 2; even more preferably r is 1; and each $R^{13a}$ and $R^{13b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo, preferably selected from halo; preferably each $R^{13a}$ and $R^{13b}$ is independently hydrogen, $C_{1-6}$alkyl, $C_{1-6}$alkyloxy, hydroxy or halo, each group being optionally substituted with one or more substituents independently selected from halo, hydroxy, $C_{1-4}$alkyloxy or oxo, preferably selected from halo; more preferably each $R^{13a}$ and $R^{13b}$ is hydrogen;

$Z^2$ is a direct bond, —O—, —S— or —$NR^{14}$; and $R^{14}$ is hydrogen or $C_{1-6}$alkyl, preferably hydrogen; more preferably $Z^2$ is —O— or —S—; most preferably $Z^2$ is —O—;

$L^4$ is a direct bond or —($CR^{15a}R^{15b}$)$_s$—; and s is an integer selected from 1, 2, 3, 4, 5 or 6; preferably s is 1, 2 or 3; more preferably s is 1 or 2; even more preferably s is 1; and each $R^{15a}$ and $R^{15b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo, preferably selected from halo; preferably each $R^{15a}$ and $R^{15b}$ is independently hydrogen, $C_{1-6}$alkyl, $C_{1-6}$alkyloxy, hydroxy or halo, each group being optionally substituted with one or more substituents independently selected from halo, hydroxy, $C_{1-4}$alkyloxy or oxo, preferably selected from halo; more preferably each $R^{15a}$ and $R^{15b}$ is hydrogen;

$R^1$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo, even more preferably fluoro; preferably $R^1$ is hydrogen, $C_{1-8}$alkyl, $C_{2-8}$alkenyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro or R$^1$ is hydrogen, C$_{1-8}$alkyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro: more preferably R$^1$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$ alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; further preferably R$^1$ is hydrogen, C$_{1-8}$alkyl, C$_{1-8}$alkyloxy, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, aryl, arylC$_{1-6}$alkyl, aryloxy, arylC$_{1-6}$alkyloxy, heterocyclyl, heterocyclylC$_{1-6}$alkyl, heterocyclyloxy, heterocyclylC$_{1-6}$alkyloxy, heteroaryl, heteroarylC$_{1-6}$alkyl, heteroaryloxy or heteroarylC$_{1-6}$alkyloxy, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; more preferably R$^1$ is C$_{1-6}$alkyl optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; even more preferably R$^1$ is propyl (preferably n-propyl), butyl, pentyl or hexyl (preferably n-hexyl), each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; equally more preferably R$^1$ is C$_{3-8}$cycloalkyl, aryl, arylC$_{1-6}$alkyl, heterocyclyl or heteroaryl, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; further preferably R$^1$ is C$_{3-8}$cycloalkyl, aryl, heterocyclyl or heteroaryl, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; even more preferably R$^1$ is aryl optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; still more preferably R$^1$ is cyclopentyl, cyclohexyl, phenyl, pentalenyl, naphthalenyl, azulenyl, pyrrolidinyl, pyrrolinyl, piperidinyl, piperazinyl, morpholinyl, dioxanyl, pyrrolyl, pyrazolyl, imidazolyl, furanyl, pyridyl (pyridinyl), pyridazinyl, pyrimidinyl, pyrazinyl, pyranyl or oxazinyl, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; most preferably R$^1$ is phenyl optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro;

R$^2$ is hydrogen, C$_{1-8}$alkyl, C$_{2-8}$alkenyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; preferably R$^2$ is hydrogen, C$_{1-8}$alkyl, C$_{2-8}$alkenyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$ alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro or R$^2$ is hydrogen, C$_{1-8}$alkyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; more preferably R$^2$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$ alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; further preferably R$^2$ is hydrogen, C$_{1-8}$alkyl, C$_{1-8}$alkyloxy, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, aryl, arylC$_{1-6}$alkyl, aryloxy, arylC$_{1-6}$alkyloxy, heterocyclyl, heterocyclylC$_{1-6}$alkyl, heterocyclyloxy, heterocyclylC$_{1-6}$alkyloxy, heteroaryl, heteroarylC$_{1-6}$alkyl, heteroaryloxy or heteroarylC$_{1-6}$alkyloxy, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; more preferably R$^2$ is C$_{1-6}$alkyl and even more preferably C$_{1-4}$alkyl, optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; even more preferably R$^2$ is propyl (more preferably n-propyl), butyl, pentyl or hexyl, optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo; equally more preferably R$^2$ is hydrogen, C$_{3-8}$cycloalkyl, aryl, heterocyclyl or heteroaryl, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; even more preferably R$^2$ is hydrogen, C$_{3-8}$cycloalkyl or aryl, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; yet more preferably R$^2$ is hydrogen, cyclopentyl, cyclohexyl, phenyl, pentalenyl, naphthalenyl, azulenyl, pyrrolidinyl, pyrrolinyl, piperidinyl, piperazinyl, morpholinyl, dioxanyl, pyrrolyl, pyrazolyl, imidazolyl, furanyl, pyridyl (pyridinyl), pyridazinyl, pyrimidinyl, pyrazinyl, pyranyl or oxazinyl, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro; and most preferably R$^2$ is hydrogen, cyclohexyl or phenyl, said cyclohexyl or phenyl being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo, even more preferably fluoro;

R$^3$ is hydrogen, C$_{1-8}$alkyl, C$_{2-8}$alkenyl, C$_{2-8}$alkynyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo, preferably selected from halo, hydroxy, C$_{1-4}$alkyl, C$_{1-4}$alkyloxy or oxo, more preferably selected from halo or C$_{1-4}$alkyloxy, even more preferably fluoro or methyloxy; preferably R$^3$ is hydrogen, C$_{1-8}$alkyl, C$_{2-8}$alkenyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$ alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy or $R^3$ is hydrogen, $C_{1-8}$alkyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; more preferably $R^3$ is hydrogen, $C_{1-8}$alkyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; further preferably $R^3$ is hydrogen, $C_{1-8}$alkyl, $C_{1-8}$alkyloxy, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, aryl, aryl$C_{1-6}$alkyl, aryloxy, aryl$C_{1-6}$alkyloxy, heterocyclyl, heterocyclyl$C_{1-6}$alkyl, heterocyclyloxy, heterocyclyl$C_{1-6}$alkyloxy, heteroaryl, heteroaryl$C_{1-6}$alkyl, heteroaryloxy or heteroaryl$C_{1-6}$alkyloxy, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; more preferably $R^3$ is hydrogen, $C_{1-8}$alkyl, $C_{3-8}$cycloalkyl, aryl, heterocyclyl or heteroaryl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; even more preferably $R^3$ is hydrogen, $C_{1-8}$alkyl, $C_{3-8}$cycloalkyl, aryl or heteroaryl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; yet more preferably $R^3$ is hydrogen, $C_{1-4}$alkyl, cyclopentyl, cyclohexyl, phenyl, pentalenyl, naphthalenyl, azulenyl, pyrrolidinyl, pyrrolinyl, piperidinyl, piperazinyl, morpholinyl, dioxanyl, pyrrolyl, pyrazolyl, imidazolyl, furanyl, pyridyl (pyridinyl), pyridazinyl, pyrimidinyl, pyrazinyl, pyranyl or oxazinyl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo, even more preferably fluoro or methyloxy; and most preferably $R^3$ is hydrogen, methyl, ethyl, n-butyl, cyclohexyl, phenyl or pyridyl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo, even more preferably fluoro or methyloxy;

$R^4$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; preferably $R^4$ is hydrogen, $C_{1-8}$alkyl, $C_{2-8}$alkenyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy or $R^4$ is hydrogen, $C_{1-8}$alkyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; more preferably $R^4$ is hydrogen, $C_{1-8}$alkyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; further preferably $R^4$ is hydrogen, $C_{1-8}$alkyl, $C_{1-8}$alkyloxy, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, aryl, aryl$C_{1-6}$alkyl, aryloxy, aryl$C_{1-6}$alkyloxy, heterocyclyl, heterocyclyl$C_{1-6}$alkyl, heterocyclyloxy, heterocyclyl$C_{1-6}$alkyloxy, heteroaryl, heteroaryl$C_{1-6}$alkyl, heteroaryloxy or heteroaryl$C_{1-6}$alkyloxy, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; more preferably $R^4$ is hydrogen, $C_{1-8}$alkyl, $C_{3-8}$cycloalkyl, aryl, heterocyclyl or heteroaryl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; even more preferably $R^4$ is hydrogen, $C_{1-8}$alkyl, $C_{3-8}$cycloalkyl, aryl or heteroaryl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo or $C_{1-4}$alkyloxy, even more preferably fluoro or methyloxy; yet more preferably $R^4$ is hydrogen, $C_{1-4}$alkyl, cyclopentyl, cyclohexyl, phenyl, pentalenyl, naphthalenyl, azulenyl, pyrrolidinyl, pyrrolinyl, piperidinyl, piperazinyl, morpholinyl, dioxanyl, pyrrolyl, pyrazolyl, imidazolyl, furanyl, pyridyl (pyridinyl), pyridazinyl, pyrimidinyl, pyrazinyl, pyranyl or oxazinyl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo, even more preferably fluoro or methyloxy; and most preferably $R^4$ is hydrogen, methyl, ethyl, n-butyl, cyclohexyl, phenyl or pyridyl, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo, preferably selected from halo, hydroxy, $C_{1-4}$alkyl, $C_{1-4}$alkyloxy or oxo, more preferably selected from halo, even more preferably fluoro or methyloxy;

with the proviso that in formula Ia at least one of $R^1$-$L^1$-, $R^2$-$L^2$-, $R^3$-$L^3$-$Z^1$— or $R^4$-$L^4$-$Z^2$— is not hydrogen and in formula Ib at least one of $R^2$-$L^2$-, $R^3$-$L^3$-$Z^1$— or $R^4$-$L^4$-$Z^2$— is not hydrogen; preferably in formula Ia at least two, more preferably at least three of $R^1$-$L^1$-, $R^2$-$L^2$-, $R^3$-$L^3$-$Z^1$— or $R^4$-$L^4$-$Z^2$— are not hydrogen; more preferably in formula Ia at least two and even more preferably all three of $R^1$-$L^1$-, $R^2$-$L^2$- and $R^3$-$L^3$-$Z^1$— are not hydrogen or at least two and even more preferably all three of $R^1$-$L^1$-, $R^2$-$L^2$- and $R^4$-$L^4$-$Z^2$— are not hydrogen; preferably in formula Ib at least two of $R^2$-$L^2$-, $R^3$-$L^3$-$Z^1$— or $R^4$-$L^4$-$Z^2$— are not hydrogen; more preferably in formula Ib $R^2$-$L^2$- and $R^3$-$L^3$-$Z^1$— are not hydrogen or $R^2$-$L^2$- and $R^4$-$L^4$-$Z^2$— are not hydrogen;

$R^7$ is hydrogen, $C_{1-6}$alkyl or $C_{1-6}$alkyloxy, optionally substituted with one or more substituents independently selected from halo, hydroxy, $C_{1-4}$alkyloxy, aryl or oxo, preferably selected from halo or $C_{1-4}$alkyloxy; preferably $R^7$ is $C_{1-6}$alkyl, more preferably $C_{1-4}$alkyl, even more preferably $C_{1-2}$alkyl, yet more preferably methyl, said $C_{1-6}$alkyl, $C_{1-4}$alkyl, $C_{1-2}$alkyl or methyl optionally substituted with one or more substituents independently selected from halo, hydroxy, $C_{1-4}$alkyloxy or oxo, preferably selected from halo or $C_{1-4}$alkyloxy;

$R^5$ is halo, $C_{1-6}$alkyl, $C_{1-6}$alkyloxy, halo$C_{1-6}$alkyl or halo$C_{1-6}$alkyloxy; preferably $R^5$ is halo or $C_{1-6}$alkyl;

$R^6$ is halo, $C_{1-6}$alkyl, $C_{1-6}$alkyloxy, halo$C_{1-6}$alkyl or halo$C_{1-6}$alkyloxy; preferably $R^6$ is halo or $C_{1-6}$alkyl;

$X^-$ is an organic or inorganic anion, preferably a pharmaceutically acceptable organic or inorganic anion; preferably $X^-$ is an organic or inorganic acid anion, preferably a pharmaceutically acceptable organic or inorganic acid anion; more preferably $X^-$ is halide (preferably chloride, bromide or iodide), sulphate, sulphite, nitrate, phosphate, phosphite, carbonate, acetate, propanoate, hydroxyacetate, lactate, pyruvate, malonate, succinate, maleate, fumarate, malate, tartarate, citrate, methanesulphonate, trifluoromethanesulfonate (triflate), ethanesulphonate, benzenesulphonate, p-toluenesulphonate, cyclamate, salicylate, p-aminosalicylate, pamoate, oxalate, isobutyrate, benzoate, suberate, mandelate, phthalate, glucuronate or galacturonate; even more preferably $X^-$ is halide (preferably chloride, bromide or iodide), sulphate, nitrate or phosphate; yet more preferably $X^-$ is halide; still more preferably $X^-$ is chloride or bromide; and most preferably $X^-$ is bromide;

or the pharmaceutically acceptable addition salts, hydrates or solvates thereof.

It was established that anti-proliferative properties of the beta-carboline derivatives described herein may at least in part depending on the number, size and the nature of substituents bound in position 2, 6 and/or 7 and 9 of the beta-carboline ring. The present disclosure thus sets forth preferred groups of the present compounds.

Preferred compounds of the general Formulas (Ia) or (Ib), any subgroups thereof, the stereoisomeric forms thereof or the pharmaceutically acceptable addition salts, hydrates or solvates thereof, may comprise a substituent or a combination of two or more substituents as set forth in any one or any combination of two or more of the following statements or restrictions (i) to (xxxviii).

(i) Preferably, $L^1$ is a direct bond, methylene or ethylene, more preferably $L^1$ is methylene, and $R^1$ is cyclohexyl, morpholinyl, phenyl, naphthalenyl or pyridyl, more preferably $R^1$ is phenyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo, preferably selected from halo, hydroxy, methyl, ethyl, methoxy, ethoxy or oxo, more preferably selected from halo, even more preferably fluoro.

(ii) Preferably, $L^1$ is a direct bond, methylene or ethylene, more preferably $L^1$ is methylene, and $R^1$ is phenyl optionally substituted with one or more substituents independently selected from halo, preferably fluoro, more preferably $R^1$ is phenyl, 2-halo-phen-1-yl, 3-halo-phen-1-yl or 4-halo-phen-1-yl, even more preferably $R^1$ is phenyl, 2-fluoro-phen-1-yl, 3-fluoro-phen-1-yl or 4-fluoro-phen-1-yl.

(iii) Particularly preferably, $R^1$-$L^1$- is benzyl, 2-halo-phen-1-ylmethyl, 3-halo-phen-1-ylmethyl, 4-halo-phen-1-ylmethyl or benzoylmethyl, even more preferably $R^1$-$L^1$- is benzyl, 2-fluoro-phen-1-ylmethyl, 3-fluoro-phen-1-ylmethyl, 4-fluoro-phen-1-ylmethyl or benzoylmethyl; or preferably, $R^1$-$L^1$- is benzyl, 2-halo-phen-1-ylmethyl, 3-halo-phen-1-ylmethyl or 4-halo-phen-1-ylmethyl, even more preferably $R^1$-$L^1$- is benzyl, 2-fluoro-phen-1-ylmethyl, 3-fluoro-phen-1-ylmethyl or 4-fluoro-phen-1-ylmethyl. (iv) Preferably, $L^2$ is a direct bond, methylene or ethylene, more preferably $L^2$ is methylene, and $R^2$ is cyclohexyl, morpholinyl, phenyl, naphthalenyl or pyridyl, more preferably $R^2$ is cyclohexyl or phenyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo, preferably selected from halo, hydroxy, methyl, ethyl, methoxy, ethoxy or oxo, more preferably selected from halo, even more preferably fluoro.

(v) Preferably, $L^2$ is a direct bond, methylene or ethylene, more preferably $L^2$ is methylene, and $R^2$ is cyclohexyl or phenyl, each of said cyclohexyl or phenyl being optionally substituted with one or more substituents independently selected from halo, preferably fluoro, more preferably $R^2$ is cyclohexyl, phenyl, 2-halo-phen-1-yl, 3-halo-phen-1-yl or 4-halo-phen-1-yl, even more preferably $R^2$ is cyclohexyl, phenyl, 2-fluoro-phen-1-yl, 3-fluoro-phen-1-yl or 4-fluoro-phen-1-yl.

(vi) Particularly preferably, $R^2$-$L^2$- is cyclohexylmethyl, benzyl, 2-halo-phen-1-ylmethyl, 3-halo-phen-1-ylmethyl or 4-halo-phen-1-ylmethyl, even more preferably $R^2$-$L^2$- is cyclohexylmethyl, benzyl, 2-fluoro-phen-1-ylmethyl, 3-fluoro-phen-1-ylmethyl or 4-fluoro-phen-1-ylmethyl.

(vii) Preferably, $L^2$ is a direct bond and $R^2$ is hydrogen, i.e., $R^2$-$L^2$- is —H.

(viii) Preferably, $Z^1$ is —O— or —S—, more preferably $Z^1$ is —O—, and $L^3$ is a direct bond, methylene or ethylene, more preferably $L^3$ is methylene, and $R^3$ is cyclohexyl, morpholinyl, phenyl, naphthalenyl or pyridyl, more preferably $R^3$ is cyclohexyl, phenyl or pyridyl, even more preferably $R^3$ is cyclohexyl or phenyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo, preferably selected from halo, hydroxy, methyl, ethyl, methoxy, ethoxy or oxo, more preferably selected from halo, even more preferably fluoro.

(ix) Preferably, $Z^1$ is —O— or —S—, more preferably $Z^1$ is —O—, and $L^3$ is a direct bond, methylene or ethylene, more preferably $L^3$ is methylene, and $R^3$ is cyclohexyl, phenyl or pyridyl, more preferably cyclohexyl or phenyl, each of said cyclohexyl, phenyl or pyridyl being optionally substituted with one or more substituents independently selected from halo, preferably fluoro, more preferably $R^3$ is cyclohexyl, phenyl, pyridyl, 2-halo-phen-1-yl, 3-halo-phen-1-yl or 4-halo-phen-1-yl, even more preferably $R^3$ is cyclohexyl, phenyl, pyrid-2-yl, pyrid-3-yl, pyrid-4-yl, 2-fluoro-phen-1-yl, 3-fluoro-phen-1-yl or 4-fluoro-phen-1-yl.

(x) Particularly preferably, $R^3$-$L^3$-$Z^1$ is cyclohexylmethoxy, benzyloxy, benzoyloxy, 2-phenyl-eth-1-yloxy, naphth-1-ylmethyloxy or naphth-2-ylmethyloxy, benzylthio, 2-halo-phen-1-ylmethoxy, 3-halo-phen-1-ylmethoxy, 4-halo-phen-1-ylmethoxy, pyrid-2-ylmethoxy, pyrid-3-ylmethoxy or pyrid-4-ylmethoxy, preferably $R^3$-$L^3$-$Z^1$ is cyclohexylmethoxy, benzyloxy, benzylthio, 2-halo-phen-1-ylmethoxy, 3-halo-phen-1-ylmethoxy, 4-halo-phen-1-ylmethoxy, pyrid-2-ylmethoxy, pyrid-3-ylmethoxy or pyrid-4-ylmethoxy, even more preferably $R^3$-$L^3$-$Z^1$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy or pyrid-4-ylmethoxy.

(xi) Also preferably, $Z^1$ is —O— or —S—, more preferably $Z^1$ is —O—, and $L^3$ is a direct bond, and $R^3$ is $C_{1-4}$alkyl, more preferably $R^3$ is methyl, ethyl, propyl or butyl, even more preferably $R^3$ is ethyl or n-butyl, each of said $C_{1-4}$alkyl, methyl, ethyl, propyl, butyl or n-butyl being optionally substituted with one or more substituents independently selected from halo, hydroxy, $C_{1-4}$alkyl, $C_{1-4}$alkyloxy, cyano, nitro or oxo, preferably selected from halo, hydroxy, methoxy, ethoxy or oxo, more preferably selected from fluoro or methoxy; even more preferably $R^3$-$L^3$-$Z^1$— is $CH_3OCH_2CH_2O$— or $CF_3(CH_2)_3O$—.

(xii) Also preferably, $Z^1$ is —O—, $L^3$ is a direct bond and $R^3$ is hydrogen, i.e., $R^3$-$L^3$-$Z^1$— is —OH.

(xiii) Also preferably, $Z^1$ and $L^3$ are each a direct bond, and $R^3$ is hydrogen, i.e., $R^3$-$L^3$-$Z^1$— is —H.

(xiv) Preferably, $Z^2$ is —O— or —S—, more preferably $Z^2$ is —O—, and $L^4$ is a direct bond, methylene or ethylene, more preferably $L^4$ is methylene, and $R^4$ is cyclohexyl, morpholinyl, phenyl, naphthalenyl or pyridyl, more preferably $R^4$ is cyclohexyl, phenyl or pyridyl, even more preferably $R^4$ is cyclohexyl or phenyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo, preferably selected from halo, hydroxy, methyl, ethyl, methoxy, ethoxy or oxo, more preferably selected from halo, even more preferably fluoro.

(xv) Preferably, $Z^2$ is —O— or —S—, more preferably $Z^2$ is —O—, and $L^4$ is a direct bond, methylene or ethylene, more preferably $L^4$ is methylene, and $R^4$ is cyclohexyl, phenyl or pyridyl, more preferably cyclohexyl or phenyl, each of said cyclohexyl, phenyl or pyridyl being optionally substituted with one or more substituents independently selected from halo, preferably fluoro, more preferably $R^4$ is cyclohexyl, phenyl, pyridyl, 2-halo-phen-1-yl, 3-halo-phen-1-yl or 4-halo-phen-1-yl, even more preferably $R^4$ is cyclohexyl, phenyl, pyrid-2-yl, pyrid-3-yl, pyrid-4-yl, 2-fluoro-phen-1-yl, 3-fluoro-phen-1-yl or 4-fluoro-phen-1-yl.

(xvi) Particularly preferably, $R^4$-$L^4$-$Z^2$ is cyclohexylmethoxy, benzyloxy, benzoylzoxy, 2-phenyl-eth-1-yloxy, naphth-1-ylmethyloxy or naphth-2-ylmethyloxy, benzylthio, 2-halo-phen-1-ylmethoxy, 3-halo-phen-1-ylmethoxy, 4-halo-phen-1-ylmethoxy, pyrid-2-ylmethoxy, pyrid-3-ylmethoxy or pyrid-4-ylmethoxy, preferably $R^4$-$L^4$-$Z^2$ is cyclohexylmethoxy, benzoylmethyl, benzylthio, 2-halo-phen-1-ylmethoxy, 3-halo-phen-1-ylmethoxy, 4-halo-phen-1-ylmethoxy, pyrid-2-ylmethoxy, pyrid-3-ylmethoxy or pyrid-4-ylmethoxy, even more preferably $R^4$-$L^4$-$Z^2$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy or pyrid-4-ylmethoxy.

(xvii) Also preferably, $Z^2$ is —O— or —S—, more preferably $Z^2$ is —O—, and $L^4$ is a direct bond, and $R^4$ is $C_{1-4}$alkyl, more preferably $R^4$ is methyl, ethyl, propyl or butyl, even more preferably $R^4$ is ethyl or n-butyl, each of said $C_{1-4}$alkyl, methyl, ethyl, propyl, butyl or n-butyl being optionally substituted with one or more substituents independently selected from halo, hydroxy, $C_{1-4}$alkyl, $C_{1-4}$alkyloxy, cyano, nitro or oxo, preferably selected from halo, hydroxy, methoxy, ethoxy or oxo, more preferably selected from fluoro or methoxy; even more preferably $R^4$-$L^4$-$Z^2$— is $CH_3OCH_2CH_2O$— or $CF_3(CH_2)_3O$—.

(xviii) Also preferably, $Z^2$ is —O—, $L^4$ is a direct bond and $R^4$ is hydrogen, i.e., $R^4$-$L^4$-$Z^2$— is —OH.

(xix) Also preferably, $Z^2$ and $L^4$ are each a direct bond, and $R^4$ is hydrogen, i.e., $R^4$-$L^4$-$Z^2$— is —H.

(xx) Preferably, $L^1$ (if present) and $R^1$ (if present) are as defined in (i) above and $L^2$ and $R^2$ are as defined in (iv) above and $Z^1$, $L^3$ and $R^3$ are as defined in (viii) above and $Z^2$, $L^4$ and $R^4$ are as defined in (xiv), (xviii) or (xix) above; or more preferably $L^1$ (if present) and $R^1$ (if present) are as defined in (ii) above and $L^2$ and $R^2$ are as defined in (v) above and $Z^1$, $L^3$ and $R^3$ are as defined in (ix) above and $Z^2$, $L^4$ and $R^4$ are as defined in (xv), (xviii) or (xix) above; or even more preferably $L^1$ (if present) and $R^1$ (if present) are as defined in (iii) above and $L^2$ and $R^2$ are as defined in (vi) above and $Z^1$, $L^3$ and $R^3$ are as defined in (x) above and $Z^2$, $L^4$ and $R^4$ are as defined in (xvi), (xviii) or (xix) above.

(xxi) Preferably, $L^1$ (if present) and $R^1$ (if present) are as defined in (i) above and $L^2$ and $R^2$ are as defined in (iv) above and $Z^1$, $L^3$ and $R^3$ are as defined in (viii), (xii) or (xiii) above and $Z^2$, $L^4$ and $R^4$ are as defined in (xiv) above; or more preferably $L^1$ (if present) and $R^1$ (if present) are as defined in (ii) above and $L^2$ and $R^2$ are as defined in (v) above and $Z^1$, $L^3$ and $R^3$ are as defined in (ix), (xii) or (xiii) above and $Z^2$, $L^4$ and $R^4$ are as defined in (xv) above; or even more preferably $L^1$ (if present) and $R^1$ (if present) are as defined in (iii) above and $L^2$ and $R^2$ are as defined in (vi) above and $Z^1$, $L^3$ and $R^3$ are as defined in (x), (xii) or (xiii) above and $Z^2$, $L^4$ and $R^4$ are as defined in (xvi) above.

(xxii) Preferably, in the general Formula (Ia), and particularly in the Formula (Ia) as set forth in any one or a combination of two or more of (i) to (xxi) above and (xxxi) to (xxxviii) below, at least $R^1$-$L^1$- and $R^2$-$L^2$- are not hydrogen or at least $R^1$-$L^1$- and $R^3$-$L^3$-$Z^1$— are not hydrogen, or at least $R^2$-$L^2$- and $R^3$-$L^3$-$Z^1$— are not hydrogen or $R^1$-$L^1$-, $R^2$-$L^2$- and $R^3$-$L^3$-$Z^1$— are not hydrogen, and preferably $R^4$-$L^4$-$Z^2$— is hydrogen or —OH, preferably hydrogen.

(xxiii) Preferably, in the general Formula (Ia), and particularly in the Formula (Ia) as set forth in any one or a combination of two or more of (i) to (xxi) above and (xxxi) to (xxxviii) below, at least $R^1$-$L^1$- and $R^2$-$L^2$- are not hydrogen or at least $R^1$-$L^1$- and $R^4$-$L^4$-$Z^2$— are not hydrogen, or at least $R^2$-$L^2$- and $R^4$-$L^4$-$Z^2$— are not hydrogen or $R^1$-$L^1$-, $R^2$-$L^2$- and $R^4$-$L^4$-$Z^4$— are not hydrogen, and preferably $R^3$-$L^3$-$Z^3$— is hydrogen or —OH, preferably hydrogen.

(xxiv) Preferably, in the general Formula (Ib), and particularly in the Formula (Ib) as set forth in any one or a combination of two or more of (i) to (xxi) above and (xxxi) to (xxxviii) below, at least $R^2$-$L^2$- is not hydrogen or at least $R^3$-$L^3$-$Z^1$— is not hydrogen, or $R^2$-$L^2$- and $R^3$-$L^3$-$Z^1$— are not hydrogen, and preferably $R^4$-$L^4$-$Z^2$— is hydrogen or —OH, preferably hydrogen.

(xxv) Preferably, in the general Formula (Ib), and particularly in the Formula (Ib) as set forth in any one or a combination of two or more of (i) to (xxi) above and (xxxi) to (xxxviii) below, at least $R^2$-$L^2$- is not hydrogen or at least $R^4$-$L^4$-$Z^2$— is not hydrogen, or $R^2$-$L^2$- and $R^4$-$L^4$-$Z^2$— are not hydrogen, and preferably $R^3$-$L^3$-$Z^1$— is hydrogen or —OH, preferably hydrogen.

(xxvi) Preferably, in the general Formulas (Ia) or (Ib), and particularly in the Formulas (Ia) or (Ib) as set forth in any one or a combination of two or more of (i) to (xxi) above and (xxxi) to (xxxviii) below, when $R^3$-$L^3$-$Z^1$— is not hydrogen then $R^4$-$L^4$-$Z^2$— is hydrogen or —OH, preferably hydrogen; or when $R^4$-$L^4$-$Z^2$— is not hydrogen then $R^3$-$L^3$-$Z^1$— is hydrogen or —OH, preferably hydrogen.

(xxvii) Preferably, in the general Formulas (Ia) or (Ib), and particularly in the Formulas (Ia) or (Ib) as set forth in any one or a combination of two or more of (i) to (xxi) above and (xxxi) to (xxxviii) below, when $R^3$-$L^3$-$Z^1$— comprises a $C_{3-8}$cycloalkyl, aryl, heterocyclyl or heteroaryl moiety then $R^4$-$L^4$-$Z^2$— does not comprise a $C_{3-8}$cycloalkyl, aryl, heterocyclyl or heteroaryl moiety; or when $R^4$-$L^4$-$Z^2$— comprises a $C_{3-8}$cycloalkyl, aryl, heterocyclyl or heteroaryl moiety then $R^3$-$L^3$-$Z^1$— does not comprise a $C_{3-8}$cycloalkyl, aryl, heterocyclyl or heteroaryl moiety.

(xxviii) Preferably, in the general Formulas (Ia) or (Ib), and particularly in the Formulas (Ia) or (Ib) as set forth in any one or a combination of two or more of (i) to (xxvii) above and (xxxi) to (xxxviii) below, $R^7$ is hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro.

(xxix) Preferably, in the general Formulas (Ia) or (Ib), and particularly in the Formulas (Ia) or (Ib) as set forth in any one or a combination of two or more of (i) to (xxviii) above and (xxxi) to (xxxviii) below, n and m are 0.

(xxx) Preferably, in the general Formulas (Ia) or (Ib), and particularly in the Formulas (Ia) or (Ib) as set forth in any one or a combination of two or more of (i) to (xxix) and (xxxi) to (xxxviii) $X^-$ is halide, more preferably $X^-$ is bromide.

(xxxi) Also preferably, $L^1$ is a direct bond and $R^1$ is $C_{1-6}$alkyl optionally substituted with one or more substituents independently selected from halo, hydroxy, $C_{1-4}$alkyl, $C_{1-4}$alkyloxy, cyano, nitro or oxo; more preferably $L^1$ is a direct bond and $R^1$ is methyl, ethyl, propyl (preferably n-propyl), butyl, pentyl or hexyl (preferably n-hexyl), each group being optionally substituted with one or more substituents independently selected from halo, hydroxy, $C_{1-4}$alkyl, $C_{1-4}$alkyloxy, cyano, nitro or oxo; even more preferably $L^1$ is a direct bond and $R^1$ is ethyl, propyl (preferably n-propyl), butyl, pentyl or hexyl (preferably n-hexyl), each group being optionally substituted with one or more substituents independently selected from halo, hydroxy, $C_{1-4}$alkyl, $C_{1-4}$alkyloxy, cyano, nitro or oxo; still more preferably $L^1$ is a direct bond and $R^1$ is propyl (preferably n-propyl), butyl, pentyl or hexyl (preferably n-hexyl), each group being optionally substituted with one or more substituents independently selected from halo, hydroxy, $C_{1-4}$alkyl, $C_{1-4}$alkyloxy, cyano, nitro or oxo; yet more preferably $L^1$ is a direct bond and $R^1$ is propyl (preferably n-propyl), butyl, pentyl or hexyl (preferably n-hexyl);

(xxxii) Particularly preferably, $R^1$-$L^1$- is 2-hydroxyethyl, propyl (preferably n-propyl), 3-methyl-butyl or hexyl (preferably n-hexyl); more preferably, $R^1$-$L^1$- is propyl (preferably n-propyl), 3-methyl-butyl or hexyl (preferably n-hexyl).

(xxxiii) Also preferably, $L^1$ is ethylene and $R^1$ is phenyl optionally substituted with one or more substituents independently selected from halo, preferably fluoro; more preferably $R^1$ is phenyl, 2-halo-phen-1-yl, 3-halo-phen-1-yl or 4-halo-phen-1-yl, even more preferably $R^1$ is phenyl, 2-fluoro-phen-1-yl, 3-fluoro-phen-1-yl or 4-fluoro-phen-1-yl.

(xxxiv) Particularly preferably, $R^1$-$L^1$- is phenylethyl.

(xxxv) Also preferably, $L^2$ is a direct bond and $R^2$ is $C_{1-6}$alkyl optionally substituted with one or more substituents independently selected from halo, hydroxy, $C_{1-4}$alkyl, $C_{1-4}$alkyloxy, cyano, nitro or oxo; more preferably $L^2$ is a direct bond and $R^2$ is methyl, ethyl, propyl, butyl, pentyl or hexyl, each group being optionally substituted with one or more substituents independently selected from halo, hydroxy, $C_{1-4}$alkyl, $C_{1-4}$alkyloxy, cyano, nitro or oxo; even more preferably $L^2$ is a direct bond and $R^2$ is propyl (preferably n-propyl) or butyl, each group being optionally substituted with one or more substituents independently selected from halo, hydroxy, $C_{1-4}$alkyl, $C_{1-4}$alkyloxy, cyano, nitro or oxo.

(xxxvi) Particularly preferably, $R^2$-$L^2$- is n-propyl or 3-methyl-butyl.

(xxxvii) Also preferably, $Z^1$ is —O— or —S—, more preferably $Z^1$ is —O—, and $L^3$ is a direct bond, and $R^3$ is $C_{1-6}$alkyl, $C_{2-6}$ alkenyl or $C_{2-6}$ alkynyl, more preferably $R^3$ is methyl, ethyl, propyl, allyl, butyl, pentyl or hexyl, even more preferably $R^3$ is ethyl, allyl, n-butyl, isobutyl or 3-methyl-butyl; each of said groups being optionally substituted with one or more substituents independently selected from halo, hydroxy, $C_{1-4}$alkyl, $C_{1-4}$alkyloxy, cyano, nitro or oxo, preferably selected from halo, hydroxy, methoxy, ethoxy or oxo, more preferably selected from fluoro or methoxy; even more preferably $R^3$-$L^3$-$Z^1$— is ethyl, allyl, n-butyl, isobutyl, 3-methyl-butyl or 2-hydroxyethyl.

(xxxviii) Also preferably, $Z^2$ is —O— or —S—, more preferably $Z^2$ is —O—, and $L^4$ is a direct bond, and $R^4$ is $C_{1-6}$alkyl, $C_{2-6}$ alkenyl or $C_{2-6}$ alkynyl, more preferably $R^4$ is methyl, ethyl, propyl, allyl, butyl, pentyl or hexyl, even more preferably $R^4$ is ethyl, allyl, n-butyl, isobutyl or 3-methyl-butyl; each of said groups being optionally substituted with one or more substituents independently selected from halo, hydroxy, $C_{1-4}$alkyl, $C_{1-4}$alkyloxy, cyano, nitro or oxo, preferably selected from halo, hydroxy, methoxy, ethoxy or oxo, more preferably selected from fluoro or methoxy; even more preferably $R^4$-$L^4$-$Z^1$— is ethyl, allyl, n-butyl, isobutyl, 3-methyl-butyl or 2-hydroxyethyl.

Preferred are compounds of the general Formulas (Ia) or (Ib), any subgroups thereof, the stereoisomeric forms thereof or the pharmaceutically acceptable addition salts, hydrates or solvates thereof, wherein $L^1$ is methylene; $R^1$ is cyclohexyl or phenyl, each of said cyclohexyl or phenyl being optionally substituted with one or more substituents independently selected from halo, preferably fluoro; $L^2$ is methylene; $R^2$ is cyclohexyl or phenyl, each of said cyclohexyl or phenyl being optionally substituted with one or more substituents independently selected from halo, preferably fluoro; $Z^1$ is —O—; $L^3$ is methylene; $R^3$ is cyclohexyl, phenyl or pyridyl, each of said cyclohexyl, phenyl or pyridyl being optionally substituted with one or more substituents independently selected from halo, preferably fluoro; or $R^3$ is ethyl or n-butyl, each of said ethyl or n-butyl being optionally substituted with one or more substituents independently selected from halo, preferably fluoro, or methoxy; $R^4$-$L^4$-$Z^2$— is hydrogen; $R^7$ is methyl; n is 0 and m is 0; $X^-$ is an organic or inorganic anion as defined above, preferably $X^-$ is halide, more preferably $X^-$ is bromide.

Preferred are compounds of the general Formulas (Ia) or (Ib), any subgroups thereof, the stereoisomeric forms thereof or the pharmaceutically acceptable addition salts, hydrates or solvates thereof, wherein $L^1$ is a direct bond and $R^1$ is methyl, ethyl, propyl, butyl, pentyl or hexyl, each group being optionally substituted with one or more hydroxy, preferably $L^1$ is a direct bond and $R^1$ is 2-hydroxy-eth-1-yl; or $L^1$ is a direct bond and $R^1$ is benzoylmethyl; $L^2$ is methylene; $R^2$ is cyclohexyl or phenyl, each of said cyclohexyl or phenyl being optionally substituted with one or more substituents independently selected from halo, preferably fluoro; $Z^1$ is —O—; $L^3$ is methylene; $R^3$ is cyclohexyl, phenyl or pyridyl, each of said cyclohexyl, phenyl or pyridyl being optionally substituted with one or more substituents independently selected from halo, preferably fluoro; or $R^3$ is ethyl or n-butyl, each of said ethyl or n-butyl being optionally substituted with one or more substituents independently selected from halo, preferably fluoro, or methoxy; $R^4$-$L^4$-$Z^2$— is hydrogen; $R^7$ is methyl; n is 0 and m is 0; $X^-$ is an organic or inorganic anion as defined above, preferably $X^-$ is halide, more preferably $X^-$ is bromide.

Preferred are also compounds of the general Formulas (Ia) or (Ib), any subgroups thereof, the stereoisomeric forms thereof or the pharmaceutically acceptable addition salts, hydrates or solvates thereof, wherein $L^1$ is methylene; $R^1$ is cyclohexyl or phenyl, each of said cyclohexyl or phenyl being optionally substituted with one or more substituents independently selected from halo, preferably fluoro; $L^2$ is methylene; $R^2$ is cyclohexyl or phenyl, each of said cyclohexyl or phenyl being optionally substituted with one or more substituents independently selected from halo, preferably fluoro; $R^3$-$L^3$-$Z^1$— is hydroxy; $R^4$-$L^4$-$Z^2$— is hydrogen; $R^7$ is methyl; n is 0 and m is 0; $X^-$ is an organic or inorganic anion as defined above, preferably $X^-$ is halide, more preferably $X^-$ is bromide.

Preferred are as well compounds of the general Formulas (Ia) or (Ib), any subgroups thereof, the stereoisomeric forms thereof or the pharmaceutically acceptable addition salts, hydrates or solvates thereof, wherein $L^1$ is methylene; $R^1$ is cyclohexyl or phenyl, each of said cyclohexyl or phenyl being optionally substituted with one or more substituents independently selected from halo, preferably fluoro; $R^2$-$L^2$- is hydrogen; $Z^1$ is —O—; $L^3$ is methylene; $R^3$ is cyclohexyl, phenyl or pyridyl, each of said cyclohexyl, phenyl or pyridyl being optionally substituted with one or more substituents independently selected from halo, preferably fluoro; or $R^3$ is ethyl or n-butyl, each of said ethyl or n-butyl being optionally substituted with one or more substituents independently selected from halo, preferably fluoro, or methoxy; $R^4$-$L^4$-$Z^2$— is hydrogen; $R^7$ is methyl; n is 0 and m is 0; $X^-$ is an organic or inorganic anion as defined above, preferably $X^-$ is halide, more preferably $X^-$ is bromide.

Also preferred are compounds of the general Formulas (Ia) or (Ib), any subgroups thereof, the stereoisomeric forms thereof or the pharmaceutically acceptable addition salts, hydrates or solvates thereof, wherein $L^1$ is methylene or ethylene, preferably ethylene; $R^1$ is phenyl; $L^2$ is methylene or ethylene, preferably methylene; $R^2$ is phenyl; $Z^1$ is —O—; $L^3$ is methylene; $R^3$ is phenyl; $R^4$-$L^4$-$Z^2$— is hydrogen; $R^7$ is methyl; each of said phenyl groups being optionally substituted with one or more substituents independently selected from halo, preferably fluoro; n is 0 and m is 0; $X^-$ is an organic or inorganic anion as defined above, preferably $X^-$ is halide, more preferably $X^-$ is bromide.

Preferred are also compounds of the general Formulas (Ia) or (Ib), any subgroups thereof, the stereoisomeric forms thereof or the pharmaceutically acceptable addition salts, hydrates or solvates thereof, wherein $L^1$ is a direct bond; $R^1$ is propyl (preferably n-propyl), butyl, pentyl or hexyl (preferably n-hexyl); $L^2$ is methylene or ethylene, preferably methylene; $R^2$ is phenyl; $Z^1$ is —O—; $L^3$ is methylene; $R^3$ is phenyl; $R^4$-$L^4$-$Z^2$— is hydrogen; $R^7$ is hydrogen or methyl, preferably methyl; each of said phenyl groups being optionally substituted with one or more substituents independently selected from halo, preferably fluoro; n is 0 and m is 0; $X^-$ is an organic or inorganic anion as defined above, preferably $X^-$ is halide, more preferably $X^-$ is bromide. Preferred are as well compounds of the general Formulas (Ia) or (Ib), any subgroups thereof, the stereoisomeric forms thereof or the pharmaceutically acceptable addition salts, hydrates or solvates thereof, wherein $L^1$ is methylene or ethylene, preferably methylene; $R^1$ is phenyl; $L^2$ is a direct bond; $R^2$ is methyl, ethyl, propyl or butyl, preferably propyl, more preferably n-propyl; $Z^1$ is —O—; $L^3$ is methylene; $R^3$ is phenyl; $R^4$-$L^4$-$Z^2$— is hydrogen; $R^7$ is hydrogen or methyl, preferably methyl; each of said phenyl groups being optionally substituted with one or more substituents independently selected from halo, preferably fluoro; n is 0 and m is 0; $X^-$ is an organic or inorganic anion as defined above, preferably $X^-$ is halide, more preferably $X^-$ is bromide. Preferred are as well compounds of the general Formulas (Ia) or (Ib), any subgroups thereof, the stereoisomeric forms thereof or the pharmaceutically acceptable addition salts, hydrates or solvates thereof, wherein $L^1$ is a direct bond and $R^1$ is methyl, ethyl, propyl, butyl, pentyl or hexyl, each group being optionally substituted with one or more hydroxy, preferably $L^1$ is a direct bond and $R^1$ is 2-hydroxy-eth-1-yl or 3-methyl-butyl; or $L^1$ is methylene or ethylene and preferably methylene and $R^1$ is phenyl optionally substituted with one or more substituents independently selected from halo, preferably fluoro; $L^2$ is a direct bond; $R^2$ is methyl, ethyl, propyl, butyl, pentyl or hexyl, preferably 3-methyl-butyl; $Z^1$ is —O—; $L^3$ is a direct bond; $R^3$ is methyl, ethyl, propyl, butyl, pentyl or hexyl, preferably 3-methyl-butyl; $R^4$-$L^4$-$Z^2$— is hydrogen; $R^7$ is hydrogen or methyl, preferably methyl; n is 0 and m is 0; $X^-$ is an organic or inorganic anion as defined above, preferably $X^-$ is halide, more preferably $X^-$ is bromide.

Preferred are as well compounds of the general Formula (Ib), any subgroups thereof, the stereoisomeric forms thereof or the pharmaceutically acceptable addition salts, hydrates or solvates thereof, wherein $L^2$ is a direct bond and $R^2$ is H (i.e., $R^2$-$L^2$- is —H); $Z^1$ is —O—; $L^3$ and $R^3$ are as defined above, preferably $L^3$ and $R^3$ are as defined in any one of the above embodiments (viii) to (xi) or (xxvii), more preferably wherein $R^3$-$L^3$ is benzyl, pyridinylmethyl (e.g., pyridin-2-yl, pyridin-3-yl, pyridin-4-yl), methoxyethyl, trifluorobutyl (e.g., $CF_3(CH_2)_3$—), benzoyl, hydroxyethyl, cyclohexylmethyl, phenylethyl, naphthyl (e.g., naphth-1-yl or naphth-2-yl), methyl, ethyl, propyl, butyl (preferably isobutyl) or allyl; $R^4$-$L^4$-$Z^2$— is hydrogen; $R^7$ is hydrogen or methyl, preferably methyl; n is 0 and m is 0.

Preferred are as well compounds of the general Formulas (Ia) or (Ib), any subgroups thereof, the stereoisomeric forms thereof or the pharmaceutically acceptable addition salts, hydrates or solvates thereof, wherein $L^1$ is methylene or ethylene; $R^1$ is cyclohexyl or phenyl, each of said cyclohexyl or phenyl being optionally substituted with one or more substituents independently selected from halo, preferably fluoro; or $R^1$-$L^1$- is propyl, 3-methyl-butyl, hexyl, 2-hydroxyethyl, benzoylmethyl; $L^2$ is methylene; $R^2$ is cyclohexyl or phenyl, each of said cyclohexyl or phenyl being optionally substituted with one or more substituents independently selected from halo, preferably fluoro; or $R^2$-$L^2$- is n-propyl, 3-methyl-butyl or hydrogen; $Z^1$ is —O—; $L^3$ is methylene; $R^3$ is cyclohexyl, phenyl or pyridyl, each of said cyclohexyl, phenyl or pyridyl being optionally substituted with one or more substituents independently selected from halo, preferably fluoro; or $R^3$ is ethyl or n-butyl, each of said ethyl or n-butyl being optionally substituted with one or more substituents independently selected from halo, preferably fluoro, or methoxy; or $R^3$-$L^3$- is 3-methyl-butyl; $R^4$-$L^4$-$Z^2$— is hydrogen; $R^7$ is methyl; n is 0 and m is 0; $X^-$ is an organic or inorganic anion, preferably $X^-$ is halide, more preferably $X^-$ is bromide.

Preferred are compounds of the general Formula (Ia) comprising the cation of the general Formula (IIa), or compounds of the general Formula (IIb),

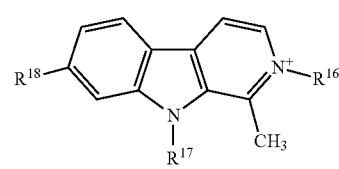

(IIa)

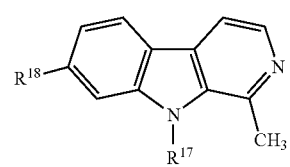

(IIb)

any subgroups thereof, the stereoisomeric forms thereof or the pharmaceutically acceptable addition salts, hydrates or solvates thereof, wherein $R^{16}$ (if present) is benzyl; $R^{17}$ is cyclohexylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is benzyl; $R^{17}$ is benzyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is benzyl; $R^{17}$ is 2-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is benzyl; $R^{17}$ is 3-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is benzyl; $R^{17}$ is 4-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is benzyl; $R^{17}$ is hydrogen and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is cyclohexylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is benzyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is 2-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is 3-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is 4-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is hydrogen and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 3-fluoro-phen-1-ylmethyl; $R^{17}$ is cyclohexylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 3-fluoro-phen-1-ylmethyl; $R^{17}$ is benzyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 3-fluoro-phen-1-ylmethyl; $R^{17}$ is 2-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 3-fluoro-phen-1-ylmethyl; $R^{17}$ is 3-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 3-fluoro-phen-1-ylmethyl; $R^{17}$ is 4-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 3-fluoro-phen-1-ylmethyl; $R^{17}$ is hydrogen and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 4-fluoro-phen-1-ylmethyl; $R^{17}$ is cyclohexylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 4-fluoro-phen-1-ylmethyl; $R^{17}$ is benzyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 4-fluoro-phen-1-ylmethyl; $R^{17}$ is 2-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 4-fluoro-phen-1-ylmethyl; $R^{17}$ is 3-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 4-fluoro-phen-1-ylmethyl; $R^{17}$ is 4-fluoro-phen-1-ylmethyl and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 4-fluoro-phen-1-ylmethyl; $R^{17}$ is hydrogen and $R^{18}$ is cyclohexylmethoxy, benzyloxy, benzylthio, 2-fluoro-phen-1-ylmethoxy, 3-fluoro-phen-1-ylmethoxy, 4-fluoro-phen-1-ylmethoxy, pyrid-2-ylmethoxy, pyrid-3-ylmethoxy, pyrid-4-ylmethoxy, $CH_3OCH_2CH_2O$—, $CF_3(CH_2)_3O$— or —OH.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is phenylmethyl; $R^{17}$ is propyl preferably n-propyl and $R^{18}$ is benzyloxy.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein $R^{16}$ (if present) is 2-fluoro-phen-1-ylmethyl; $R^{17}$ is propyl preferably n-propyl and $R^{18}$ is benzyloxy.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein R$^{16}$ (if present) is 4-fluoro-phen-1-ylmethyl; R$^{17}$ is propyl preferably n-propyl and R$^{18}$ is benzyloxy.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein R$^{16}$ (if present) is hexyl preferably n-hexyl; R$^{17}$ is benzyl and R$^{18}$ is benzyloxy.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein R$^{16}$ (if present) is propyl preferably n-propyl; R$^{17}$ is benzyl and R$^{18}$ is benzyloxy.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein R$^{16}$ (if present) is 3-methyl-butyl; R$^{17}$ is benzyl and R$^{18}$ is benzyloxy.

Preferred are also compounds of the general Formula (Ia) comprising the cation of the general Formula (IIa), and compounds of the general Formula (IIb), any subgroups thereof, the stereoisomeric forms thereof or the pharmaceutically acceptable addition salts, hydrates or solvates thereof, wherein R$^{16}$ (if present) is phenylethyl; R$^{17}$ is benzyl and R$^{18}$ is benzyloxy.

Preferred are also compounds of the general Formula (IIIa) or (IIIb), or stereoisomeric forms thereof,

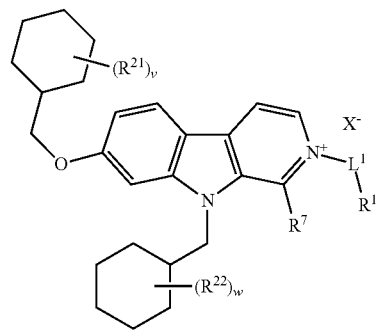

(IIIa)

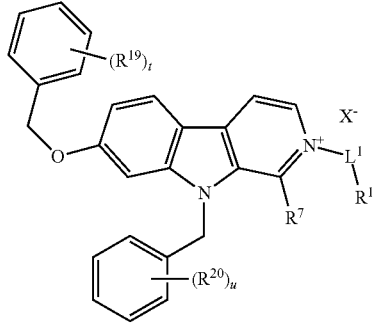

(IIIb)

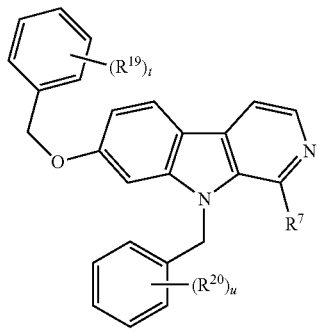

wherein
t is an integer selected from 0, 1 or 2, preferably t is 0 or 1;
u is an integer selected from 0, 1 or 2, preferably u is 0 or 1;
R$^{19}$ is each independently halo, preferably fluoro;
R$^{20}$ is each independently halo, preferably fluoro;
R$^7$, R$^1$, L$^1$ and X$^-$ have their respective meanings as set forth elsewhere in this specification and R$^1$-L$^1$- is preferably benzyl, 2-fluoro-phen-1-ylmethyl, 3-fluoro-phen-1-ylmethyl, 4-fluoro-phen-1-ylmethyl, phenylethyl, propyl (more preferably n-propyl), 3-methyl-butyl, hexyl (preferably n-hexyl), benzoylmethyl or 2-hydroxyethyl, or preferably R$^1$-L$^1$- is benzyl, 2-fluoro-phen-1-ylmethyl, 3-fluoro-phen-1-ylmethyl or 4-fluoro-phen-1-ylmethyl;
R$^7$ is preferably hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro;
X$^-$ is preferably halide, more preferably X$^-$ is bromide;
or the pharmaceutically acceptable addition salts, hydrates or solvates thereof.

Preferred are also compounds of the general Formula (IVa) or (IVb), or stereoisomeric forms thereof, (IVa)

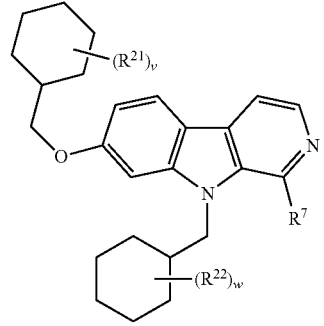

(IVb)

wherein
v is an integer selected from 0, 1 or 2, preferably v is 0 or 1;
w is an integer selected from 0, 1 or 2, preferably w is 0 or 1;
R$^{21}$ is each independently halo, preferably fluoro;
R$^{22}$ is each independently halo, preferably fluoro;
R$^7$, R$^1$, L$^1$ and X$^-$ have their respective meanings as set forth elsewhere in this specification and R$^1$-L$^1$- is preferably benzyl, 2-fluoro-phen-1-ylmethyl, 3-fluoro-phen-1-ylmethyl, 4-fluoro-phen-1-ylmethyl, phenylethyl, propyl (more preferably n-propyl), 3-methyl-butyl, hexyl (preferably n-hexyl), benzoylmethyl or 2-hydroxyethyl, or preferably R$^1$-L$^1$- is benzyl, 2-fluoro-phen-1-ylmethyl, 3-fluoro-phen-1-ylmethyl or 4-fluoro-phen-1-ylmethyl;
R$^7$ is preferably hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro;
X$^-$ is preferably halide, more preferably X$^-$ is bromide;

or the pharmaceutically acceptable addition salts, hydrates or solvates thereof.

Preferred are also compounds of the general Formula (VIIa) or (VIIb), or stereoisomeric forms thereof,

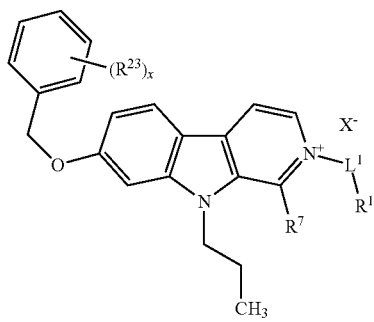

(VIIa)

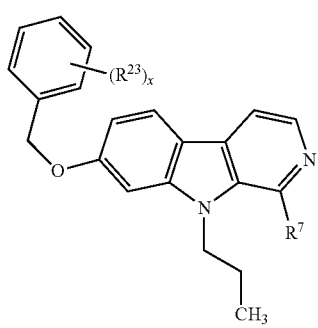

(VIIb)

wherein
x is an integer selected from 0, 1 or 2, preferably x is 0;
$R^{23}$ is each independently halo, preferably fluoro;
$R^7$, $R^1$, $L^1$ and $X^-$ have their respective meanings as set forth elsewhere in this specification and $R^1$-$L^1$- is preferably benzyl, 2-fluoro-phen-1-ylmethyl or 4-fluoro-phen-1-ylmethyl; $R^7$ is preferably methyl;
$X^-$ is preferably halide, more preferably $X^-$ is bromide;
or the pharmaceutically acceptable addition salts, hydrates or solvates thereof.

Preferred albeit non-limiting examples of compounds of the general Formulas (Ia) or (Ib), the stereoisomeric forms thereof or the pharmaceutically acceptable addition salts, hydrates or solvates thereof, as prepared and disclosed herein include those listed in Table 1.

TABLE 1

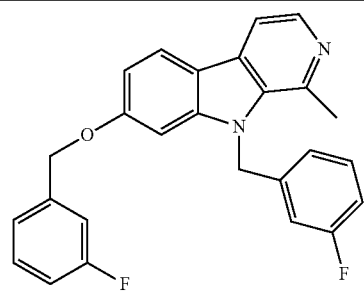

CV5
1-methyl-7-(3-fluorobenzyloxy)-9-(3-fluorobenzyl)-β-carboline

TABLE 1-continued

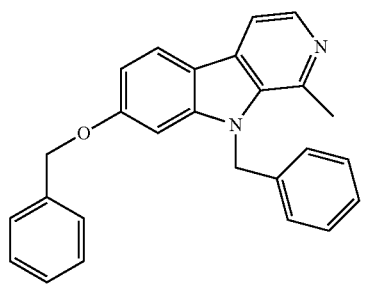

CV9 (JR84)
1-methyl-7-benzyloxy-9-benzyl-β-carboline

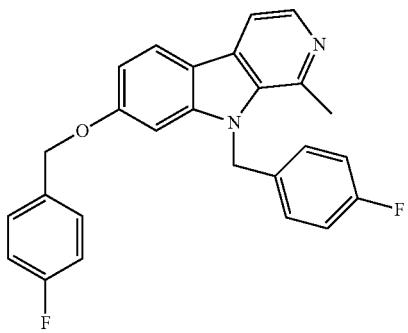

CV11
1-methyl-7-(4-fluorobenzyloxy)-9-(4-fluorobenzyl)-β-carboline

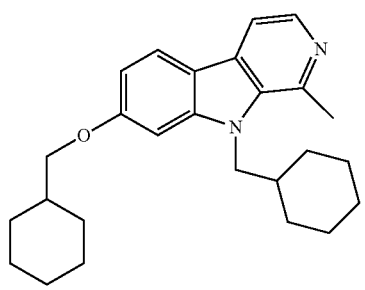

CV12
1-methyl-7-cyclohexylmethyloxy-9-cyclohexylmethyl-β-carboline

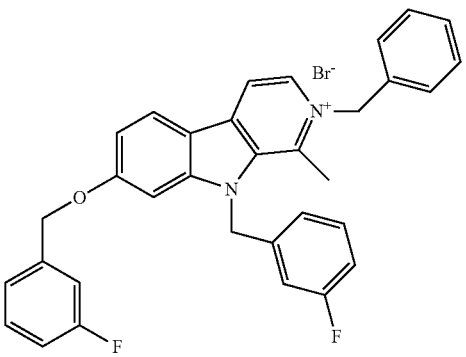

CV16
1-methyl-2-benzyl-7-(3-fluorobenzyl)oxy-9-(3-fluorobenzyl)-β-carbolin-2-ium bromide TABLE 1-continued

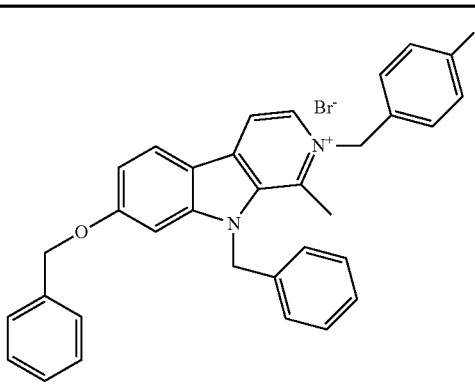

CV17
1-methyl-2-(4-fluorobenzyl)-7-benzyloxy-9-
benzyl-β-carbolin-2-ium bromide

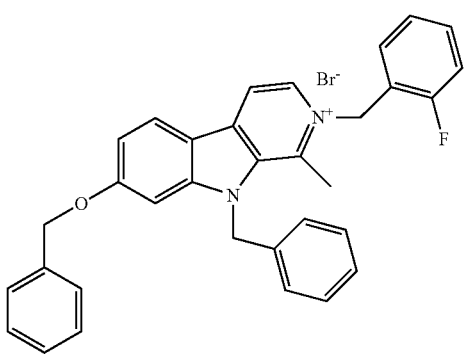

CV18
1-methyl-2-(2-fluorobenzyl)-7-benzyloxy-9-
benzyl-β-carbolin-2-ium bromide

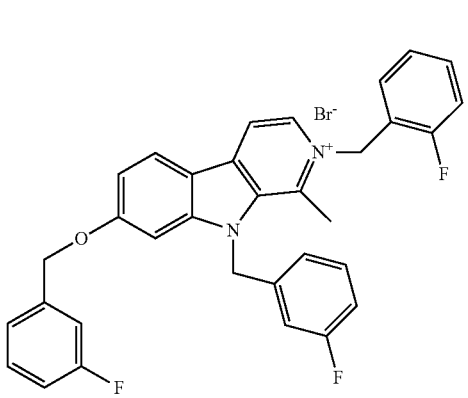

CV19
1-methyl-2-(2-fluorobenzyl)-7-(3-
fluorobenzyl)oxy-9-(3-fluorobenzyl)-β-carbolin-
2-ium bromide TABLE 1-continued

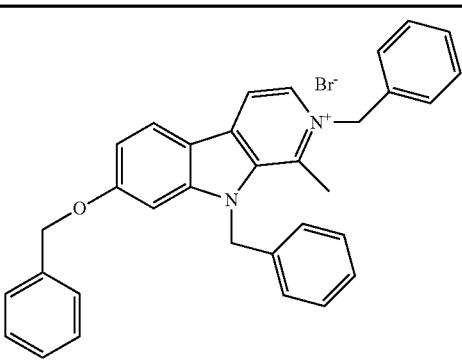

CV21 (JR95)
1-methyl-2-benzyl-7-benzyloxy-9-benzyl-β-
carbolin-2-ium bromide

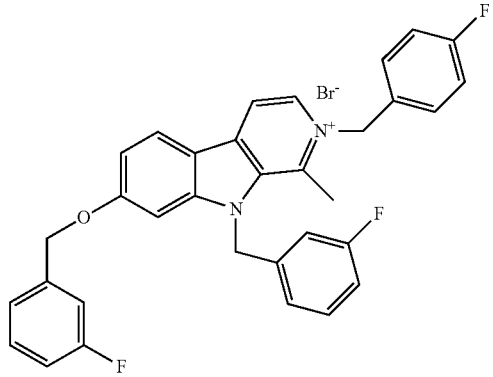

CV22
1-methyl-2-(4-fluorobenzyl)-7-(3-
fluorobenzyl)oxy-9-(3-fluorobenzyl)-β-carbolin-
2-ium bromide

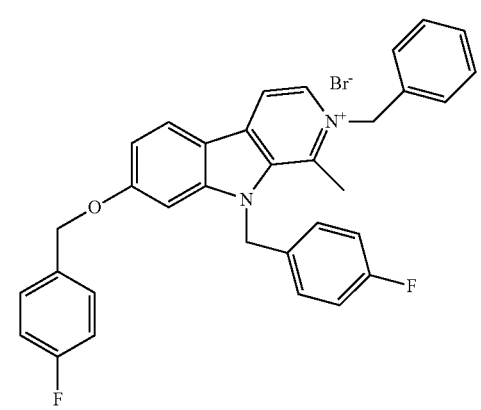

CV23
1-methyl-2-benzyl-7-(4-fluorobenzyl)oxy-9-(4-
fluorobenzyl)-β-carbolin-2-ium bromide TABLE 1-continued

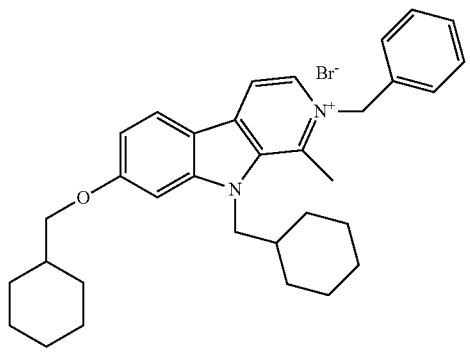

CV24
1-methyl-2-benzyl-7-cyclohexylmethyloxy-9-
cyclohexylmethyl-β-carbolin-2-ium bromide

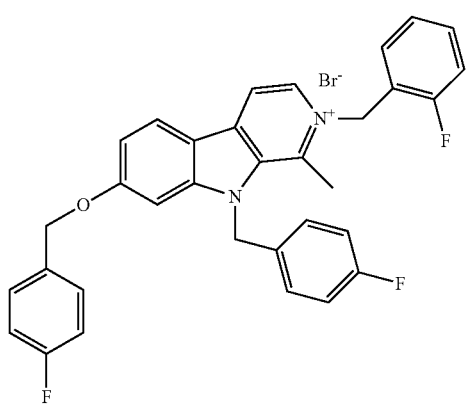

CV25
1-methyl-2-(2-fluorobenzyl)-7-(4-
fluorobenzyl)oxy-9-(4-fluorobenzyl)-β-carbolin-
2-ium bromide

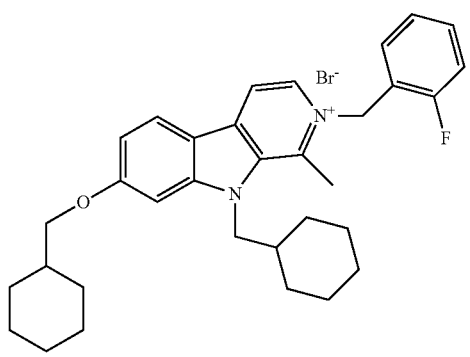

CV26
1-methyl-2-(2-fluorobenzyl)-7-
cyclohexylmethyloxy-9-cyclohexylmethyl-β-
carbolin-2-ium bromide

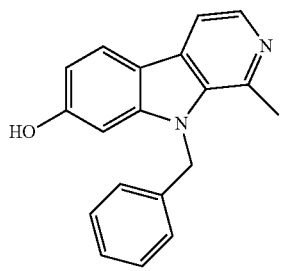

CV27
1-methyl-7-hydroxy-9-benzyl-β-carboline

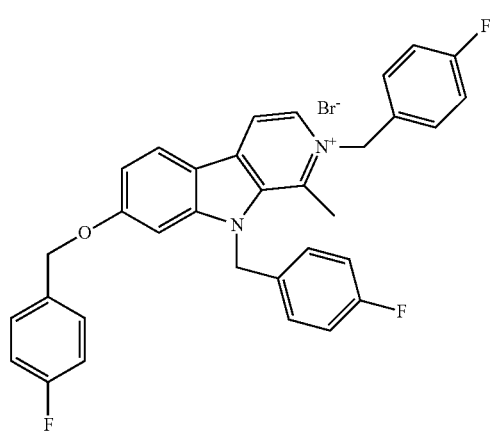

CV29
1-methyl-2-(4-fluorobenzyl)-7-(4-
fluorobenzyl)oxy-9-(4-fluorobenzyl)-β-carbolin-
2-ium bromide

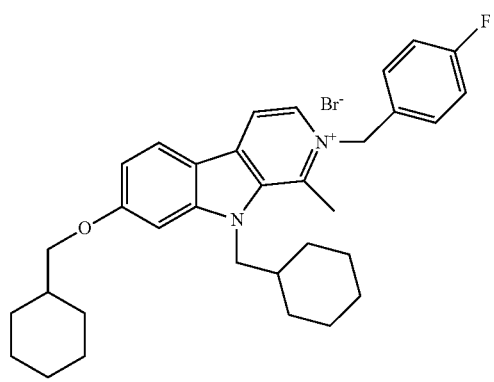

CV30
1-methyl-2-(4-fluorobenzyl)-7-
cyclohexylmethyloxy-9-cyclohexylmethyl-β-
carbolin-2-ium bromide

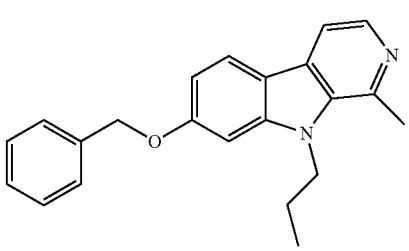

CV33
1-methyl-7-benzyloxy-9-propyl-β-carboline

TABLE 1-continued

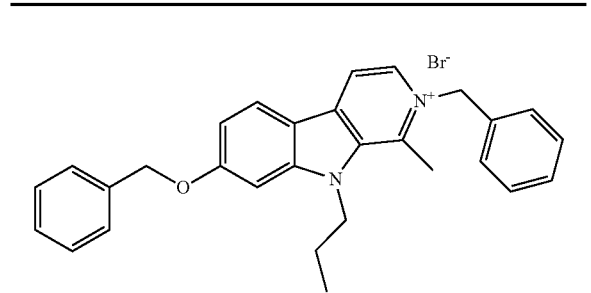

CV34
1-methyl-2-benzyl-7-benzyloxy-9-propyl-β-carbolin-2-ium bromide

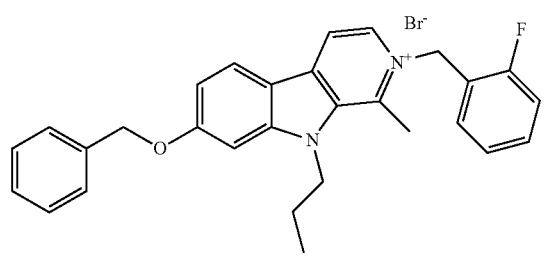

CV35
1-methyl-2-(2-fluorobenzyl)-7-benzyloxy-9-propyl-β-carbolin-2-ium bromide

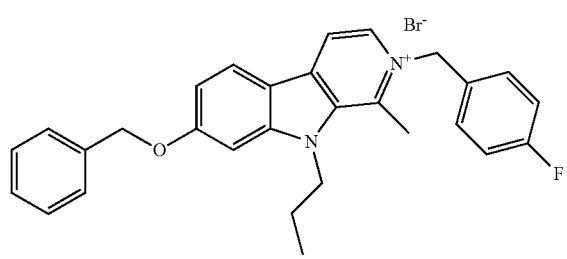

CV36
1-methyl-2-(4-fluorobenzyl)-7-benzyloxy-9-propyl-β-carbolin-2-ium bromide

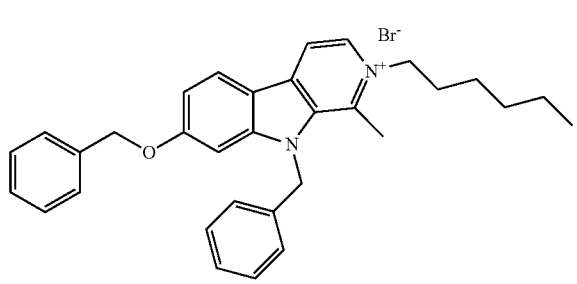

CV53
1-methyl-2-hexyl-7-benzyloxy-9-benzyl-β-carbolin-2-ium bromide

TABLE 1-continued

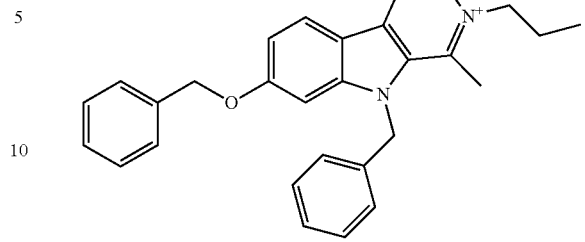

CV56
1-methyl-2-propyl-7-benzyloxy-9-benzyl-β-carbolin-2-ium bromide

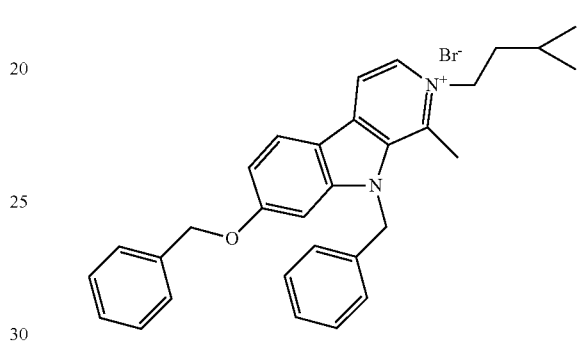

PL2
1-methyl-2-(3-methylbutyl)-7-benzyloxy-9-benzyl-β-carbolin-2-ium bromide

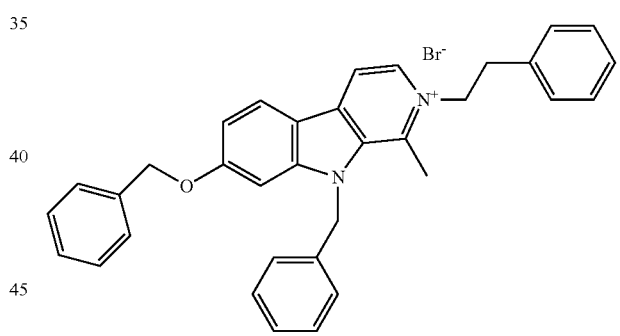

PL4
1-methyl-2-phenethyl-7-benzyloxy-9-benzyl-β-carbolin-2-ium bromide

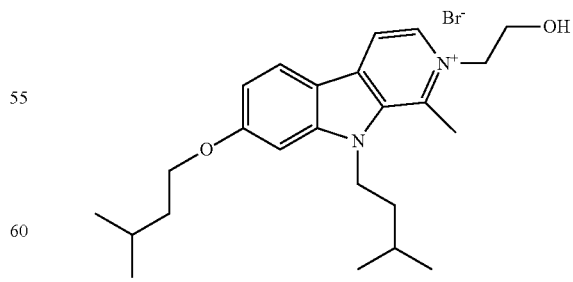

PL11
1-methyl-2-hydroxyethyl-7-(3-methylbutyloxy)-9-(3-methylbutyl)-β-carbolin-2-ium bromide TABLE 1-continued

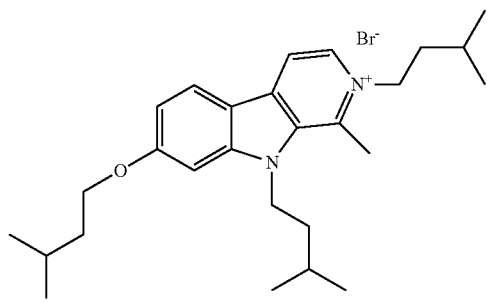

PL12
1-methyl-2-(3-methylbutyl)-7-(3-methylbutyloxy)-9-(3-methylbutyl)-β-carbolin-2-ium bromide

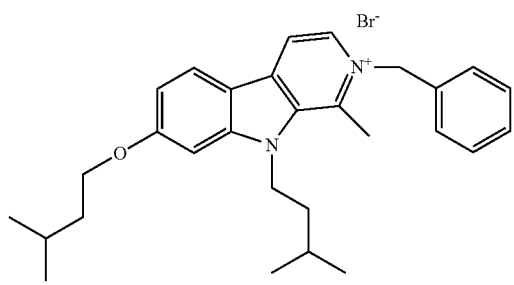

PL13
1-methyl-2-benzyl-7-(3-methylbutyloxy)-9-(3-methylbutyl)-β-carbolin-2-ium bromide

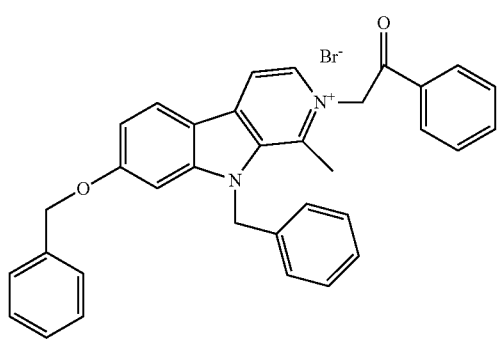

CV52
1-methyl-2-benzoylmethyl-7-benzyl-9-benzyl-β-carbolin-2-ium bromide

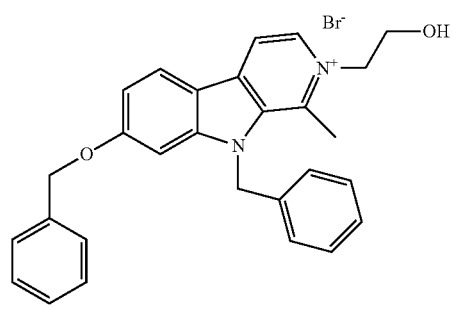

PL1
1-methyl-2-hydroxyethyl-7-benzyl-9-benzyl-β-carbolin-2-ium bromide

Further preferred albeit non-limiting examples of compounds of the general Formulas (Ia) or (Ib), the stereoisomeric forms thereof or the pharmaceutically acceptable addition salts, hydrates or solvates thereof, as prepared and disclosed herein include those listed in Table 2.

TABLE 2

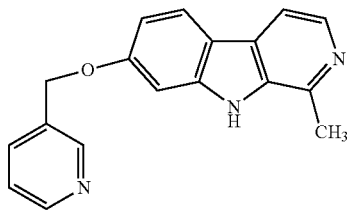

JR212
7-(pyridin-3-ylmethoxy)-1-methyl-β-carboline

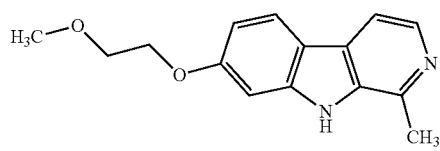

JR220
7-(2-methoxyethoxy)-1-methyl-β-carboline

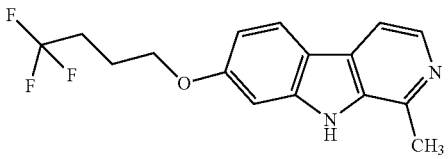

JR110
7-(4,4,4-trifluorobutoxy)-1-methyl-β-carboline

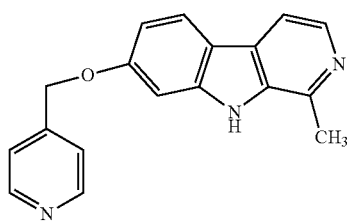

JR222
7-(pyridine-4-ylmethoxy)-1-methyl-β-carboline

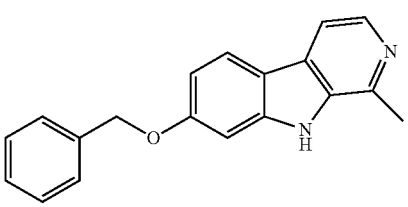

JR79
1-methyl-7-benzyloxy-β-carboline

TABLE 2-continued
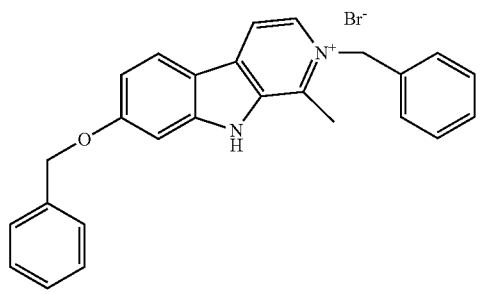
JR88
1-methyl-2-benzyl-7-benzyl-9H-β-carboline
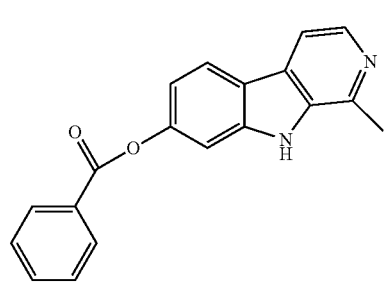
JR140
1-methyl-7-benzoyloxy-9H-β-carboline
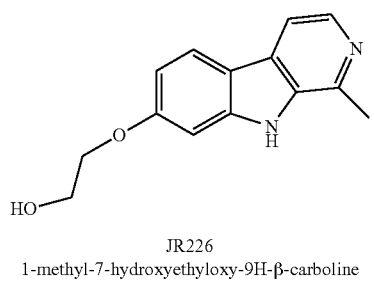 [SMILES: Cc1nccc2c1[nH]c1cc(OCCO)ccc12]
JR226
1-methyl-7-hydroxyethyloxy-9H-β-carboline
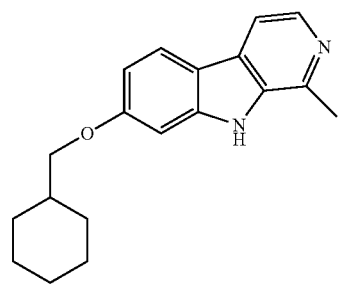
JR167
1-methyl-7-cyclohexylmethyloxy-9H-β-carboline
TABLE 2-continued
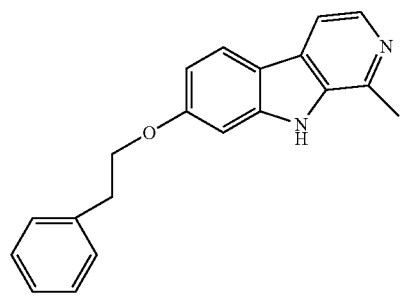
JR155
1-methyl-7-phenethyloxy-9H-β-carboline
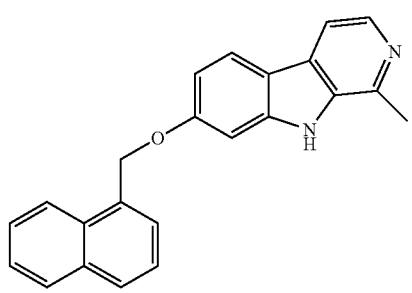
JR147
1-methyl-7-(napht-1-yl)methyloxy-9H-β-carboline
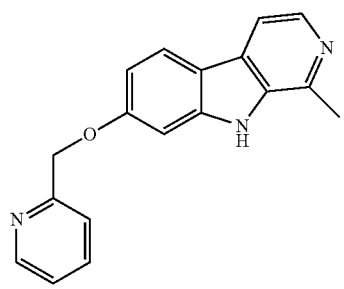
JR169
1-methyl-7-(pyrid-2-yloxy)-9H-β-carboline
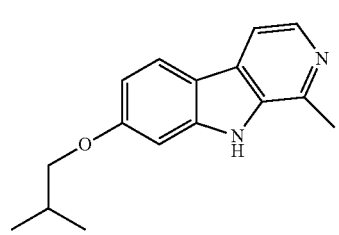
JR221
1-methyl-7-(2-methylpropyloxy)-9H-β-carboline TABLE 2-continued

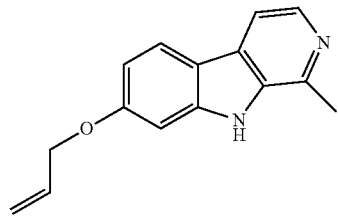

JR211
1-methyl-7-allyloxy-9H-β-carboline

In a further aspect, the present invention also encompasses subject-matter as set forth in any one and all of (A) to (S) below:

(A). A compound of any one of Formulas (Ia) or (Ib), or stereoisomeric forms thereof,

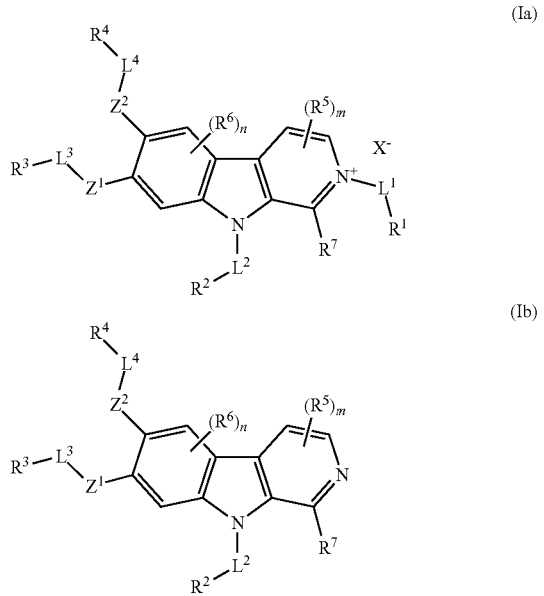

wherein
m is an integer selected from 0, 1 or 2;
n is an integer selected from 0, 1 or 2;
$L^1$ is a direct bond, —O—, —S—, —NR$^8$— or —(CR$^{9a}$R$^{9b}$)$_p$—; and R$^8$ is hydrogen or C$_{1-6}$alkyl; and p is an integer selected from 1, 2, 3, 4, 5 or 6; and each R$^{9a}$ and R$^{9b}$ is independently hydrogen, C$_{1-6}$alkyl, C$_{1-6}$alkyloxy, C$_{1-6}$alkylthio, C$_{1-6}$alkylamino, hydroxy or halo, each group being optionally substituted with one or more substituents independently selected from halo, hydroxy, C$_{1-4}$alkyloxy or oxo;
$L^2$ is a direct bond —O—, —S—, —NR$^{10}$— or —(CR$^{11a}$R$^{11b}$)$_q$—; and R$^{10}$ is hydrogen or C$_{1-6}$alkyl; and q is an integer selected from 1, 2, 3, 4, 5 or 6; and each R$^{11a}$ and R$^{11b}$ is independently hydrogen, C$_{1-6}$alkyl, C$_{1-6}$alkyloxy, C$_{1-6}$alkylthio, C$_{1-6}$alkylamino, hydroxy or halo, each group being optionally substituted with one or more substituents independently selected from halo, hydroxy, C$_{1-4}$alkyloxy or oxo;
$Z^1$ is a direct bond, —O—, —S— or —NR$^{12}$; and R$^{12}$ is hydrogen or C$_{1-6}$alkyl;
$L^3$ is a direct bond or —(CR$^{13a}$R$^{13b}$)$_r$—; and r is an integer selected from 1, 2, 3, 4, 5 or 6; and each R$^{13a}$ and R$^{13b}$ is independently hydrogen, C$_{1-6}$alkyl, C$_{1-6}$alkyloxy, C$_{1-6}$alkylthio, C$_{1-6}$alkylamino, hydroxy or halo, each group being optionally substituted with one or more substituents independently selected from halo, hydroxy, C$_{1-4}$alkyloxy or oxo;
$Z^2$ is a direct bond, —O—, —S— or —NR$^{14}$; and R$^{14}$ is hydrogen or C$_{1-6}$alkyl;
$L^4$ is a direct bond or —(CR$^{15a}$R$^{15b}$)$_s$—; and s is an integer selected from 1, 2, 3, 4, 5 or 6; and each R$^{15a}$ and R$^{15b}$ is independently hydrogen, C$_{1-6}$alkyl, C$_{1-6}$alkyloxy, C$_{1-6}$alkylthio, C$_{1-6}$alkylamino, hydroxy or halo, each group being optionally substituted with one or more substituents independently selected from halo, hydroxy, C$_{1-4}$alkyloxy or oxo;
$R^1$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl; heteroaryloxy, heteroarylC$_{1-6}$ alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo;
$R^2$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$ alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo;
$R^3$ is hydrogen, C$_{1-8}$alkyl, C$_{1-8}$alkyloxy, C$_{1-8}$alkylthio, C$_{1-8}$alkylamino, C$_{3-8}$cycloalkyl, C$_{3-8}$cycloalkylC$_{1-6}$alkyl, C$_{3-8}$cycloalkyloxy, C$_{3-8}$cycloalkylC$_{1-6}$alkyloxy, C$_{3-8}$cycloalkylthio, C$_{3-8}$cycloalkylC$_{1-6}$alkylthio, C$_{3-8}$cycloalkylamino, C$_{3-8}$cycloalkylC$_{1-6}$alkylamino, aryl, arylC$_{1-6}$alkyl, aryloxy, arylC$_{1-6}$alkyloxy, arylthio, arylC$_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$alkyl, heteroaryloxy, heteroarylC$_{1-6}$ alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo;

$R^4$ is hydrogen, $C_{1-8}$alkyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo;

with the proviso that in formula Ia at least one of $R^1$-$L^1$-, $R^2$-$L^2$-, $R^3$-$L^3$-$Z^1$— or $R^4$-$L^4$-$Z^2$— is not hydrogen and in formula Ib at least one of $R^2$-$L^2$-, $R^3$-$L^3$-$Z^1$— or $R^4$-$L^4$-$Z^2$— is not hydrogen;

$R^7$ is hydrogen, $C_{1-6}$alkyl or $C_{1-6}$alkyloxy, optionally substituted with one or more substituents independently selected from halo, hydroxy, $C_{1-4}$alkyloxy, aryl or oxo;

$R^5$ is halo, $C_{1-6}$alkyl, $C_{1-6}$alkyloxy, halo$C_{1-6}$alkyl or halo$C_{1-6}$alkyloxy;

$R^6$ is halo, $C_{1-6}$alkyl, $C_{1-6}$alkyloxy, halo$C_{1-6}$alkyl or halo$C_{1-6}$alkyloxy;

$X^-$ is an organic or inorganic anion;

or pharmaceutically acceptable addition salts, hydrates or solvates thereof.

(B). The compound as set forth in (A) above, wherein $L^1$ is a direct bond, methylene or ethylene, and $R^1$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo; preferably wherein $L^1$ is methylene, and $R^1$ is phenyl optionally substituted with one or more substituents independently selected from halo.

(C). The compound as set forth in (A) or (B) above, wherein $L^2$ is a direct bond, methylene or ethylene, and $R^2$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo; preferably wherein $L^2$ is methylene, and $R^2$ is cyclohexyl or phenyl, each of said cyclohexyl or phenyl being optionally substituted with one or more substituents independently selected from halo.

(D). The compound as set forth in any one of (A) to (C) above, wherein $Z^1$ is —O— or —S—, $L^3$ is a direct bond, methylene or ethylene, and $R^3$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo; preferably wherein $Z^1$ is —O—, $L^3$ is methylene and $R^3$ is cyclohexyl, phenyl or pyridyl, each of said cyclohexyl, phenyl or pyridyl being optionally substituted with one or more substituents independently selected from halo.

(E). The compound as set forth in any one of (A) to (D) above, wherein $Z^1$ is —O— or —S—, $L^3$ is a direct bond, and $R^3$ is $C_{1-4}$alkyl optionally substituted with one or more substituents independently selected from halo, hydroxy, $C_{1-4}$alkyl, $C_{1-4}$alkyloxy, cyano, nitro or oxo.

(F). The compound as set forth in any one of (A) to (E) above, wherein $Z^2$ is —O— or —S—, and $L^4$ is a direct bond, methylene or ethylene, and $R^4$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, $C_{1-4}$alkyl, $C_{1-4}$alkyloxy, cyano, nitro or oxo; preferably wherein $Z^2$ is —O—, and $L^4$ is methylene, and $R^4$ is cyclohexyl, phenyl or pyridyl, each of said cyclohexyl, phenyl or pyridyl being optionally substituted with one or more substituents independently selected from halo.

(G). The compound as set forth in any one of (A) to (E) above, wherein $Z^2$ is —O— or —S—, $L^4$ is a direct bond, and $R^4$ is $C_{1-4}$alkyl optionally substituted with one or more substituents independently selected from halo, hydroxy, $C_{1-4}$alkyl, $C_{1-4}$alkyloxy, cyano, nitro or oxo.

(H). The compound as set forth in any one of (A) to (G) above, wherein in the general Formula (Ia) at least $R^1$-$L^1$- and $R^2$-$L^2$- are not hydrogen or at least $R^1$-$L^1$- and $R^3$-$L^3$-$Z^1$— are not hydrogen, or at least $R^2$-$L^2$- and $R^3$-$L^3$-$Z^1$— are not hydrogen or $R^1$-$L^1$-, $R^2$-$L^2$- and $R^3$-$L^3$-$Z^1$— are not hydrogen, and preferably $R^4$-$L^4$-$Z^2$— is hydrogen or —OH, preferably hydrogen; or in the general Formula (Ib) at least $R^2$-$L^2$- is not hydrogen or at least $R^3$-$L^3$-$Z^1$— is not hydrogen, or $R^2$-$L^2$- and $R^3$-$L^3$-$Z^1$— are not hydrogen, and preferably $R^4$-$L^4$-$Z^2$— is hydrogen or —OH, preferably hydrogen.

(I). The compound as set forth in any one of (A) to (G) above, wherein in the general Formula (Ia) at least $R^1$-$L^1$- and $R^2$-$L^2$- are not hydrogen or at least $R^1$-$L^1$- and $R^4$-$L^4$-$Z^2$— are not hydrogen, or at least $R^2$-$L^2$- and $R^4$-$L^4$-$Z^2$— are not hydrogen or $R^1$-$L^1$-, $R^2$-$L^2$- and $R^4$-$L^4$-$Z^4$— are not hydrogen, and preferably $R^3$-$L^3$-$Z^3$— is hydrogen or —OH, preferably hydrogen; or in the general Formula (Ib) at least $R^2$-$L^2$- is not hydrogen or at least $R^4$-$L^4$-$Z^2$— is not hydrogen, or $R^2$-$L^2$- and $R^4$-$L^4$-$Z^2$— are not hydrogen, and preferably $R^3$-$L^3$-$Z^1$— is hydrogen or —OH, preferably hydrogen.

(J). The compound as set forth in any one of (A) to (I) above, wherein when $R^3$-$L^3$-$Z^1$— is not hydrogen then $R^4$-$L^4$-$Z^2$— is hydrogen or —OH, preferably hydrogen; or when $R^4$-$L^4$-$Z^2$— is not hydrogen then $R^3$-$L^3$-$Z^1$— is hydrogen or —OH, preferably hydrogen.

(K). The compound as set forth in any one of (A) to (J) above, wherein $R^7$ is hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro.

(L). The compound as set forth in (A) above, wherein $L^1$ is methylene; $R^1$ is cyclohexyl or phenyl, each of said cyclohexyl or phenyl being optionally substituted with one or more substituents independently selected from halo, preferably fluoro; $L^2$ is methylene; $R^2$ is cyclohexyl or phenyl, each of said cyclohexyl or phenyl being optionally substituted with one or more substituents independently selected from halo, preferably fluoro; $Z^1$ is —O—; $L^3$ is methylene; $R^3$ is cyclohexyl, phenyl or pyridyl, each of said cyclohexyl, phenyl or pyridyl being optionally substituted with one or more substituents independently selected from halo, preferably fluoro; or $R^3$ is ethyl or n-butyl, each of said ethyl or n-butyl being optionally substituted with one or more substituents independently selected from halo, preferably fluoro, or methoxy; $R^4$-$L^4$-$Z^2$— is hydrogen; $R^7$ is methyl; n is 0 and m is 0; X⁻ is an organic or inorganic anion, preferably X⁻ is halide, more preferably X⁻ is bromide.

(M). A compound of the general Formula (IIIa) or (IIIb), or stereoisomeric forms thereof,

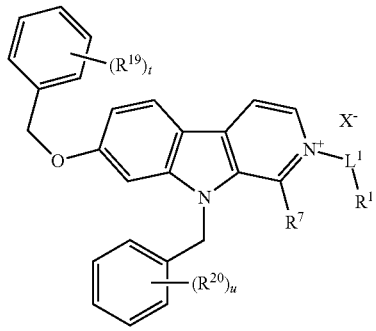

(IIIa)

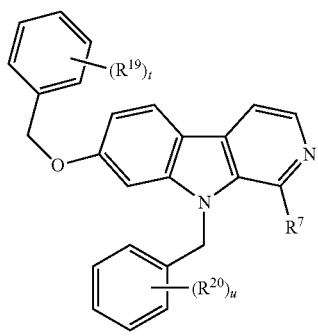

(IIIb)

wherein t is an integer selected from 0, 1 or 2, preferably t is 0 or 1;

u is an integer selected from 0, 1 or 2, preferably u is 0 or 1;

$R^{19}$ is each independently halo, preferably fluoro;

$R^{20}$ is each independently halo, preferably fluoro;

$R^7, R^1, L^1$ and $X^-$ have their respective meanings as set forth in any one of claims 1 to 12, and $R^1$-$L^1$- is preferably benzyl, 2-fluoro-phen-1-ylmethyl, 3-fluoro-phen-1-ylmethyl or 4-fluoro-phen-1-ylmethyl;

$R^7$ is preferably hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro;

X⁻ is preferably halide, more preferably X⁻ is bromide;

or the pharmaceutically acceptable addition salts, hydrates or solvates thereof.

(N). A compound of the general Formula (IVa) or (IVb), or stereoisomeric forms thereof,

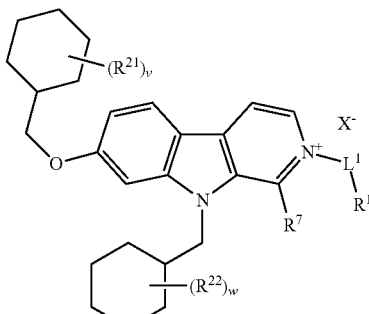

(IVa)

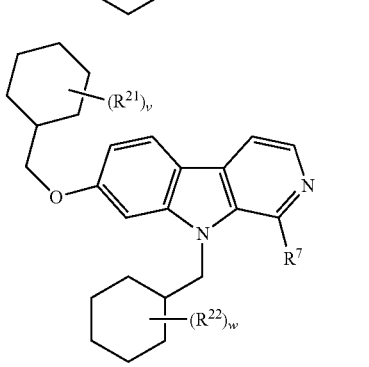

(IVb)

wherein v is an integer selected from 0, 1 or 2, preferably v is 0 or 1;

w is an integer selected from 0, 1 or 2, preferably w is 0 or 1;

$R^{21}$ is each independently halo, preferably fluoro;

$R^{22}$ is each independently halo, preferably fluoro;

$R^7, R^1, L^1$ and $X^-$ have their respective meanings as set forth in any one of claims 1 to 12, and $R^1$-$L^1$- is preferably benzyl, 2-fluoro-phen-1-ylmethyl, 3-fluoro-phen-1-ylmethyl or 4-fluoro-phen-1-ylmethyl;

$R^7$ is preferably hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro;

X⁻ is preferably halide, more preferably X⁻ is bromide;

or the pharmaceutically acceptable addition salts, hydrates or solvates thereof.

(O). A pharmaceutical composition comprising the compound as defined in any one of (A) to (N), the stereoisomeric forms thereof or the pharmaceutically acceptable addition salts, hydrates or solvates thereof, and one or more pharmaceutically acceptable excipients.

(P). The compound as set forth in any one of (A) to (N) above, the stereoisomeric forms thereof or the pharmaceutically acceptable addition salts, hydrates or solvates thereof, or the pharmaceutical composition as set forth in (P), for use as a medicament, preferably for use in the treatment of a proliferative disorder.

(Q). A method for treating a proliferative disorder in a subject in need of such treatment, comprising administering to said subject a therapeutically effective amount of the compound as set forth in any one (A) to (N) above, the stereoisomeric forms thereof or the pharmaceutically acceptable addition salts, hydrates or solvates thereof, or the pharmaceutical composition as set forth in (O) above.

(R). The subject matter as set forth in (P) or (Q) above, wherein the proliferative disorder is a cancer selected from the group of: non-small cell lung cancer, prostate cancer (more preferably refractory prostate cancer), breast cancer (preferably triple-negative breast cancer, i.e., breast cancer not expressing oestrogen receptor (ER), progesterone receptor (PR) and Her2/neu), glioma preferably glioblastoma, colon cancer and melanoma.

(S). The subject matter as set forth in (P) or (Q) above, wherein the proliferative disorder is an apoptosis-resistant tumour or cancer.

In a further aspect, the present invention also encompasses subject-matter as set forth in any one and all of (A') to (S') below:

(A'). A compound of any one of Formulas (Ia) or (Ib), or stereoisomeric forms thereof,

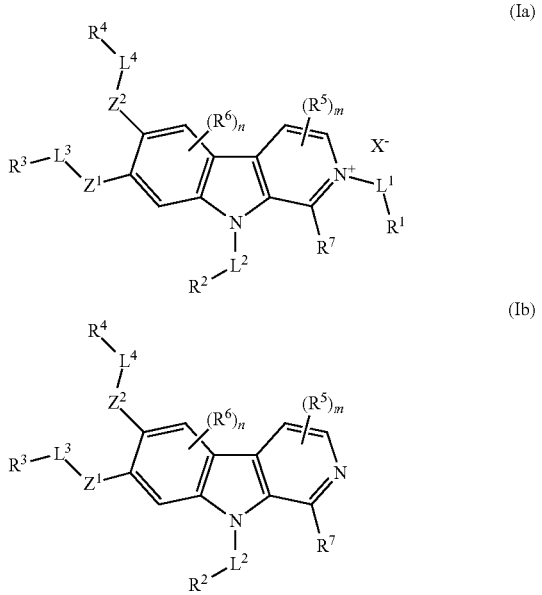

wherein
m is an integer selected from 0, 1 or 2;
n is an integer selected from 0, 1 or 2;
$L^1$ is a direct bond, —O—, —S—, —$NR^8$— or —$(CR^{9a}R^{9b})_p$—; and $R^8$ is hydrogen or $C_{1-6}$alkyl; and p is an integer selected from 1, 2, 3, 4, 5 or 6; and each $R^{9a}$ and $R^{9b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;
$L^2$ is a direct bond, —O—, —S—, —$NR^{10}$— or —$(CR^{11a}R^{11b})_q$—; and $R^{10}$ is hydrogen or $C_{1-6}$alkyl; and q is an integer selected from 1, 2, 3, 4, 5 or 6; and each $R^{11a}$ and $R^{11b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;
$Z^1$ is a direct bond, —O—, —S— or —$NR^{12}$; and $R^{12}$ is hydrogen or $C_{1-6}$alkyl;
$L^3$ is a direct bond or —$(CR^{13a}R^{13b})_r$—; and r is an integer selected from 1, 2, 3, 4, 5 or 6; and each $R^{13a}$ and $R^{13b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;
$Z^2$ is a direct bond, —O—, —S— or —$NR^{14}$; and $R^{14}$ is hydrogen or $C_{1-6}$alkyl;
$L^4$ is a direct bond or —$(CR^{15a}R^{15b})_s$—; and s is an integer selected from 1, 2, 3, 4, 5 or 6; and each $R^{15a}$ and $R^{15b}$ is independently hydrogen, $C_{1-6}$alkyl, $C_{1-6}$alkyloxy, $C_{1-6}$alkylthio, $C_{1-6}$alkylamino, hydroxy or halo, each group being optionally substituted with one or more substituents independently selected from halo, hydroxy, $C_{1-4}$alkyloxy or oxo;
$R^1$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl; heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo;
$R^2$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo;
$R^3$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, aryl$C_{1-6}$alkylamino, heterocyclyl, heterocyclyl$C_{1-6}$alkyl, heterocyclyloxy, heterocyclyl$C_{1-6}$alkyloxy, heterocyclylthio, heterocyclyl$C_{1-6}$alkylthio, heterocyclylamino, heterocyclyl$C_{1-6}$alkylamino, heteroaryl, heteroaryl$C_{1-6}$alkyl, heteroaryloxy, heteroaryl$C_{1-6}$alkyloxy, heteroarylthio, heteroaryl$C_{1-6}$alkylthio, heteroarylamino or heteroaryl$C_{1-6}$alkylamino, each group being optionally substituted with one or more substituents independently selected from halo, hydroxy, $C_{1-4}$alkyl, $C_{1-4}$alkyloxy, $C_{1-4}$alkylthio, $C_{1-4}$alkylamino, cyano, nitro or oxo;
$R^4$ is hydrogen, $C_{1-8}$alkyl, $C_{2-8}$alkenyl, $C_{2-8}$alkynyl, $C_{1-8}$alkyloxy, $C_{1-8}$alkylthio, $C_{1-8}$alkylamino, $C_{3-8}$cycloalkyl, $C_{3-8}$cycloalkyl$C_{1-6}$alkyl, $C_{3-8}$cycloalkyloxy, $C_{3-8}$cycloalkyl$C_{1-6}$alkyloxy, $C_{3-8}$cycloalkylthio, $C_{3-8}$cycloalkyl$C_{1-6}$alkylthio, $C_{3-8}$cycloalkylamino, $C_{3-8}$cycloalkyl$C_{1-6}$alkylamino, aryl, aryl$C_{1-6}$alkyl, aryloxy, aryl$C_{1-6}$alkyloxy, arylthio, aryl$C_{1-6}$alkylthio, arylamino, arylC$_{1-6}$alkylamino, heterocyclyl, heterocyclylC$_{1-6}$alkyl, heterocyclyloxy, heterocyclylC$_{1-6}$alkyloxy, heterocyclylthio, heterocyclylC$_{1-6}$alkylthio, heterocyclylamino, heterocyclylC$_{1-6}$alkylamino, heteroaryl, heteroarylC$_{1-6}$ alkyl, heteroaryloxy, heteroarylC$_{1-6}$alkyloxy, heteroarylthio, heteroarylC$_{1-6}$alkylthio, heteroarylamino or heteroarylC$_{1-6}$alkylamino, each group being optionally substituted with one or more substituents independently selected from halo, hydroxy, C$_{1-4}$alkyl, C$_{1-4}$alkyloxy, C$_{1-4}$alkylthio, C$_{1-4}$alkylamino, cyano, nitro or oxo;

with the proviso that in formula Ia at least one of R$^1$-L$^1$-, R$^2$-L$^2$-, R$^3$-L$^3$-Z$^1$— or R$^4$-L$^4$-Z$^2$— is not hydrogen and in formula Ib at least one of R$^2$-L$^2$-, R$^3$-L$^3$-Z$^1$— or R$^4$-L$^4$-Z$^2$— is not hydrogen;

R$^7$ is hydrogen, C$_{1-6}$alkyl or C$_{1-6}$alkyloxy, optionally substituted with one or more substituents independently selected from halo, hydroxy, C$_{1-4}$alkyloxy, aryl or oxo;

R$^5$ is halo, C$_{1-6}$alkyl, C$_{1-6}$alkyloxy, haloC$_{1-6}$alkyl or haloC$_{1-6}$alkyloxy;

R$^6$ is halo, C$_{1-6}$alkyl, C$_{1-6}$alkyloxy, haloC$_{1-6}$alkyl or haloC$_{1-6}$alkyloxy;

X$^-$ is an organic or inorganic anion;

or pharmaceutically acceptable addition salts, hydrates or solvates thereof.

(B') The compound according to (A') above, wherein L$^1$ is a direct bond, methylene or ethylene, and R$^1$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, C$_{1-4}$alkyl, C$_{1-4}$alkyloxy, cyano, nitro or oxo or R$^1$ is C$_{1-6}$alkyl optionally substituted with one or more substituents independently selected from halo, hydroxy, C$_{1-4}$alkyl, C$_{1-4}$alkyloxy, cyano, nitro or oxo; preferably wherein L$^1$ is methylene or ethylene and R$^1$ is phenyl optionally substituted with one or more substituents independently selected from halo or R$^1$ is benzoyl; or also preferably wherein L$^1$ is a direct bond and R$^1$ is C$_{1-6}$alkyl preferably methyl, ethyl, propyl, butyl, pentyl or hexyl, each group being optionally substituted with one or more substituents independently selected from halo, hydroxy, C$_{1-4}$alkyl, C$_{1-4}$alkyloxy, cyano, nitro or oxo.

(C') The compound according to any one of (A') or (B') above, wherein L$^2$ is a direct bond, methylene or ethylene, and R$^2$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, C$_{1-4}$alkyl, C$_{1-4}$alkyloxy, cyano, nitro or oxo; preferably wherein L$^2$ is methylene, and R$^2$ is cyclohexyl or phenyl, each of said cyclohexyl or phenyl being optionally substituted with one or more substituents independently selected from halo; or wherein L$^2$ is a direct bond and R$^2$ is C$_{1-6}$alkyl, preferably methyl, ethyl, propyl, butyl, pentyl or hexyl, each group being optionally substituted with one or more substituents independently selected from halo, hydroxy, C$_{1-4}$alkyl, C$_{1-4}$alkyloxy, cyano, nitro or oxo.

(D') The compound according to any one of (A') to (C') above, wherein Z$^1$ is —O— or —S—, L$^3$ is a direct bond, methylene or ethylene, and R$^3$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, C$_{1-4}$alkyl, C$_{1-4}$alkyloxy, cyano, nitro or oxo; preferably wherein Z$^1$ is —O—, L$^3$ is methylene and R$^3$ is cyclohexyl, phenyl or pyridyl, each of said cyclohexyl, phenyl or pyridyl being optionally substituted with one or more substituents independently selected from halo.

(E') The compound according to any one of (A') to (D') above, wherein Z$^1$ is —O— or —S—, L$^3$ is a direct bond, and R$^3$ is C$_{1-4}$alkyl optionally substituted with one or more substituents independently selected from halo, hydroxy, C$_{1-4}$alkyl, C$_{1-4}$alkyloxy, cyano, nitro or oxo, or R$^3$ is C$_{1-6}$alkyl, C$_{2-6}$ alkenyl or C$_{2-6}$ alkynyl, each of said groups being optionally substituted with one or more substituents independently selected from halo, hydroxy, C$_{1-4}$alkyl, C$_{1-4}$alkyloxy, cyano, nitro or oxo.

(F') The compound according to any one of (A') to (E') above, wherein Z$^2$ is —O— or —S—, and L$^4$ is a direct bond, methylene or ethylene, and R$^4$ is cyclohexyl, morpholinyl, phenyl, naphthalenyl or pyridyl, each of said cyclohexyl, morpholinyl, phenyl, naphthalenyl or pyridyl being optionally substituted with one or more substituents independently selected from halo, hydroxy, C$_{1-4}$alkyl, C$_{1-4}$alkyloxy, cyano, nitro or oxo; preferably wherein Z$^2$ is —O—, and L$^4$ is methylene, and R$^4$ is cyclohexyl, phenyl or pyridyl, each of said cyclohexyl, phenyl or pyridyl being optionally substituted with one or more substituents independently selected from halo.

(G') The compound according to any one of (A') to (E') above, wherein Z$^2$ is —O— or —S—, L$^4$ is a direct bond, and R$^4$ is C$_{1-4}$alkyl optionally substituted with one or more substituents independently selected from halo, hydroxy, C$_{1-4}$alkyl, C$_{1-4}$alkyloxy, cyano, nitro or oxo, or R$^4$ is C$_{1-6}$alkyl, C$_{2-6}$ alkenyl or C$_{2-6}$ alkynyl, each of said groups being optionally substituted with one or more substituents independently selected from halo, hydroxy, C$_{1-4}$alkyl, C$_{1-4}$alkyloxy, cyano, nitro or oxo.

(H') The compound according to any one of (A') to (G') above, wherein in the general Formula (Ia) at least R$^1$-L$^1$- and R$^2$-L$^2$- are not hydrogen or at least R$^1$-L$^1$- and R$^3$-L$^3$-Z$^1$— are not hydrogen, or at least R$^2$-L$^2$- and R$^3$-L$^3$-Z$^1$— are not hydrogen or R$^1$-L$^1$-, R$^2$-L$^2$- and R$^3$-L$^3$-Z$^1$— are not hydrogen, and preferably R$^4$-L$^4$-Z$^2$— is hydrogen or —OH, preferably hydrogen; or in the general Formula (Ib) at least R$^2$-L$^2$- is not hydrogen or at least R$^3$-L$^3$-Z$^1$— is not hydrogen, or R$^2$-L$^2$- and R$^3$-L$^3$-Z$^1$— are not hydrogen, and preferably R$^4$-L$^4$-Z$^2$— is hydrogen or —OH, preferably hydrogen.

(I') The compound according to any one of (A') to (G') above, wherein in the general Formula (Ia) at least R$^1$-L$^1$- and R$^2$-L$^2$- are not hydrogen or at least R$^1$-L$^1$- and R$^4$-L$^4$-Z$^2$— are not hydrogen, or at least R$^2$-L$^2$- and R$^4$-L$^4$-Z$^2$— are not hydrogen or R$^1$-L$^1$-, R$^2$-L$^2$- and R$^4$-L$^4$-Z$^4$— are not hydrogen, and preferably R$^3$-L$^3$-Z$^3$— is hydrogen or —OH, preferably hydrogen; or in the general Formula (Ib) at least R$^2$-L$^2$- is not hydrogen or at least R$^4$-L$^4$-Z$^2$— is not hydrogen, or R$^2$-L$^2$- and R$^4$-L$^4$-Z$^2$— are not hydrogen, and preferably R$^3$-L$^3$-Z$^1$— is hydrogen or —OH, preferably hydrogen.

(J') The compound according to any one of (A') to (I') above, wherein when R$^3$-L$^3$-Z$^1$— is not hydrogen then R$^4$-L$^4$-Z$^2$— is hydrogen or —OH, preferably hydrogen; or when R$^4$-L$^4$-Z$^2$— is not hydrogen then R$^3$-L$^3$-Z$^1$— is hydrogen or —OH, preferably hydrogen.

(K') The compound according to any one of (A') to (J') above, wherein R$^7$ is hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro.

(L') The compound according to (A') above, wherein $L^1$ is methylene or ethylene; $R^1$ is cyclohexyl or phenyl, each of said cyclohexyl or phenyl being optionally substituted with one or more substituents independently selected from halo, preferably fluoro; or $R^1$-$L^1$- is propyl, 3-methyl-butyl, hexyl, 2-hydroxyethyl, benzoylmethyl; $L^2$ is methylene; $R^2$ is cyclohexyl or phenyl, each of said cyclohexyl or phenyl being optionally substituted with one or more substituents independently selected from halo, preferably fluoro; or $R^2$-$L^2$- is n-propyl, 3-methyl-butyl or hydrogen; $Z^1$ is —O—; $L^3$ is methylene; $R^3$ is cyclohexyl, phenyl or pyridyl, each of said cyclohexyl, phenyl or pyridyl being optionally substituted with one or more substituents independently selected from halo, preferably fluoro; or $R^3$ is ethyl or n-butyl, each of said ethyl or n-butyl being optionally substituted with one or more substituents independently selected from halo, preferably fluoro, or methoxy; or $R^3$-$L^3$- is 3-methyl-butyl; $R^4$-$L^4$-$Z^2$— is hydrogen; $R^7$ is methyl; n is 0 and m is 0; $X^-$ is an organic or inorganic anion, preferably $X^-$ is halide, more preferably $X^-$ is bromide.

(M') A compound of the general Formula (IIIa) or (IIIb), or stereoisomeric forms thereof,

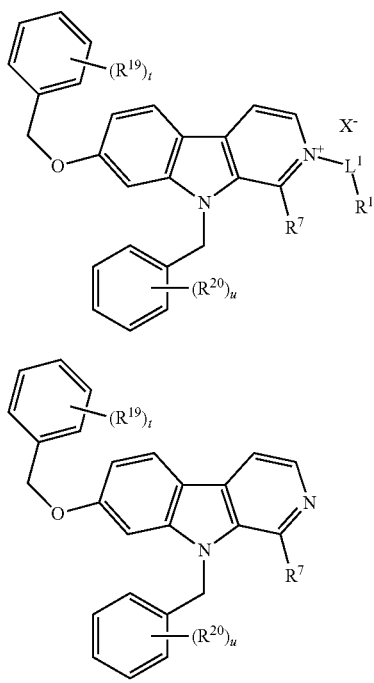

(IIIa)

(IIIb)

wherein t is an integer selected from 0, 1 or 2, preferably t is 0 or 1;
u is an integer selected from 0, 1 or 2, preferably u is 0 or 1;
$R^{19}$ is each independently halo, preferably fluoro;
$R^{20}$ is each independently halo, preferably fluoro;
$R^7$, $R^1$, $L^1$ and $X^-$ have their respective meanings as set forth in any one of claims 1 to 12, and $R^1$-$L^1$- is preferably benzyl, 2-fluoro-phen-1-ylmethyl, 3-fluoro-phen-1-ylmethyl, 4-fluoro-phen-1-ylmethyl phenylethyl, propyl (more preferably n-propyl), 3-methyl-butyl, hexyl (preferably n-hexyl), benzoylmethyl or 2-hydroxyethyl; $R^7$ is preferably hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro; $X^-$ is preferably halide, more preferably $X^-$ is bromide;

or the pharmaceutically acceptable addition salts, hydrates or solvates thereof.

(N') A compound of the general Formula (IVa) or (IVb), or stereoisomeric forms thereof,

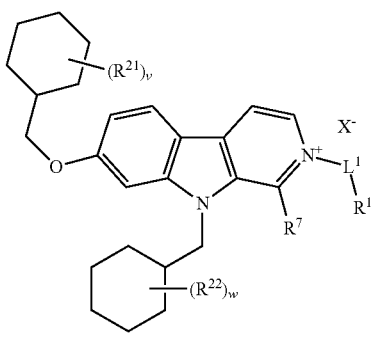

(IVa)

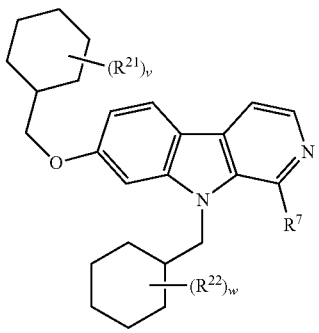

(IVb)

wherein v is an integer selected from 0, 1 or 2, preferably v is 0 or 1;
w is an integer selected from 0, 1 or 2, preferably w is 0 or 1;
$R^{21}$ is each independently halo, preferably fluoro;
$R^{22}$ is each independently halo, preferably fluoro;
$R^7$, $R^1$, $L^1$ and $X^-$ have their respective meanings as set forth in any one of claims 1 to 12, and $R^1$-$L^1$- is preferably benzyl, 2-fluoro-phen-1-ylmethyl, 3-fluoro-phen-1-ylmethyl, 4-fluoro-phen-1-ylmethyl, phenylethyl, propyl (more preferably n-propyl), 3-methyl-butyl, hexyl (preferably n-hexyl), benzoylmethyl or 2-hydroxyethyl; $R^7$ is preferably hydrogen, methyl, ethyl, methoxy, ethoxy, methoxymethyl, methoxyethyl, ethoxymethyl or ethoxyethyl, each group being optionally substituted with one or more substituents independently selected from halo, hydroxy or oxo, preferably halo, more preferably fluoro; $X^-$ is preferably halide, more preferably $X^-$ is bromide;

or the pharmaceutically acceptable addition salts, hydrates or solvates thereof.

(O') A compound of the general formula (VIIa) or (VIIb), or stereoisomeric forms thereof,

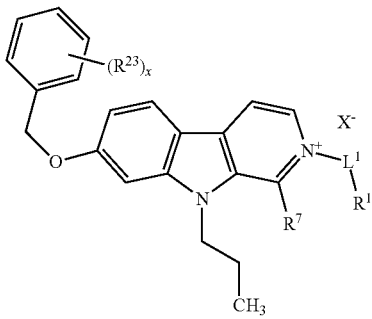

(VIIa)

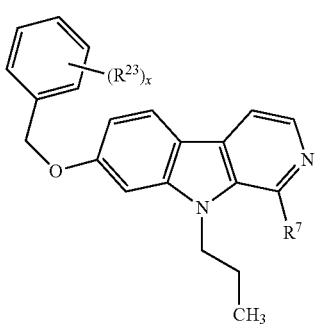

(VIIb)

wherein
x is an integer selected from 0, 1 or 2, preferably x is 0;
$R^{23}$ is each independently halo, preferably fluoro;
$R^7, R^1, L^1$ and $X^-$ have their respective meanings as set forth elsewhere in this specification and $R^1$-$L^1$- is preferably benzyl, 2-fluoro-phen-1-ylmethyl or 4-fluoro-phen-1-ylmethyl; $R^7$ is preferably methyl;
$X^-$ is preferably halide, more preferably $X^-$ is bromide;
or the pharmaceutically acceptable addition salts, hydrates or solvates thereof.
(P') A pharmaceutical composition comprising the compound according to any one of (A') to (O') above, the stereoisomeric forms thereof or the pharmaceutically acceptable addition salts, hydrates or solvates thereof, and one or more pharmaceutically acceptable excipients.
(Q') The compound according to any one of (A') to (O') above, the stereoisomeric forms thereof or the pharmaceutically acceptable addition salts, hydrates or solvates thereof, or the pharmaceutical composition according to claim 16, for use as a medicament, preferably for use in the treatment of a proliferative disorder.
(R') A method for treating a proliferative disorder in a subject in need of such treatment, comprising administering to said subject a therapeutically effective amount of the compound according to any one of (A') to (O') above, the stereoisomeric forms thereof or the pharmaceutically acceptable addition salts, hydrates or solvates thereof, or the pharmaceutical composition according to (P') above.
(S') The subject matter as defined in any one (Q') or (R') above, wherein the proliferative disorder is a cancer selected from the group of: non-small cell lung cancer, prostate cancer (more preferably refractory prostate cancer), breast cancer (preferably triple-negative breast cancer, i.e., breast cancer not expressing oestrogen receptor (ER), progesterone receptor (PR) and Her2/neu), glioma preferably glioblastoma, colon cancer and melanoma.
(T') The subject matter as defined in any one of claims (Q') or (R') above, wherein the proliferative disorder is an apoptosis-resistant tumour or cancer.

The present invention also encompasses processes for the preparation of compounds of Formulas (Ia) or (Ib) and subgroups thereof.

In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

Functional groups, which are desirable to protect, include hydroxy, amino, carboxylic acid, ketones and aldehydes. Suitable protecting groups for hydroxy include trialkylsilyl groups (such as for example tert-butyldimethylsilyl, tert-butyldiphenylsilyl or trimethylsilyl), benzyl and tetrahydropyranyl. Suitable protecting groups for amino include tert-butyloxycarbonyl, benzyloxycarbonyl, ethoxycarbonyl, benzyl. Suitable protecting groups for ketones and aldehydes include methoxy, ethoxy, or one bivalent protecting group such as, for example, 2,2-dimethylpropane-1,3-diolate. Suitable protecting groups for carboxylic acid include $C_{1-6}$alkyl or benzyl esters.

The compounds of Formulas (Ia) or (Ib) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below:

Compounds of Formula (Ib1) wherein $R^2$-$L^2$- and $R^3$-$L^3$- are the same (further, $Z^1$ is —O— and $R^4$-$L^4$-$Z^2$ is hydrogen and the remaining substituents have the same meaning as that defined above) may be prepared as shown in Scheme 2 by reacting a compound of Formula (VIb) with the compound $R^2$-$L^2$-$G^1$ (which is identical to $R^3$-$L^3$-$G^1$) (wherein $R^2$, $L^2$, $R^3$ and $L^3$ have meanings as defined above), wherein $G^1$ is an appropriate leaving group, such as preferably halo, more preferably bromo or iodo, under basic conditions, to yield said compound of Formula (Ib1).

Scheme 2

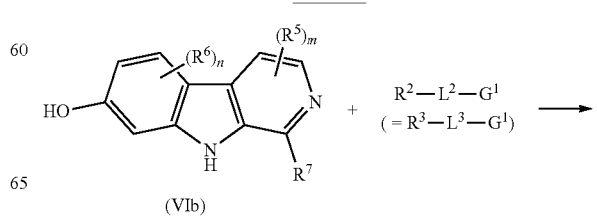

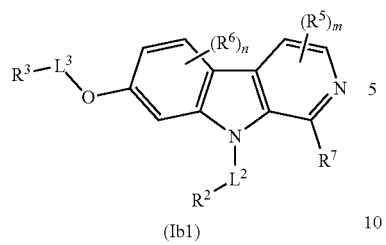

(Ib1)

Said compounds of Formula (VIb) may be prepared as shown in Scheme 3 by reacting a compound of Formula (VIa) with HBr under acidic conditions (e.g., acetic acid).

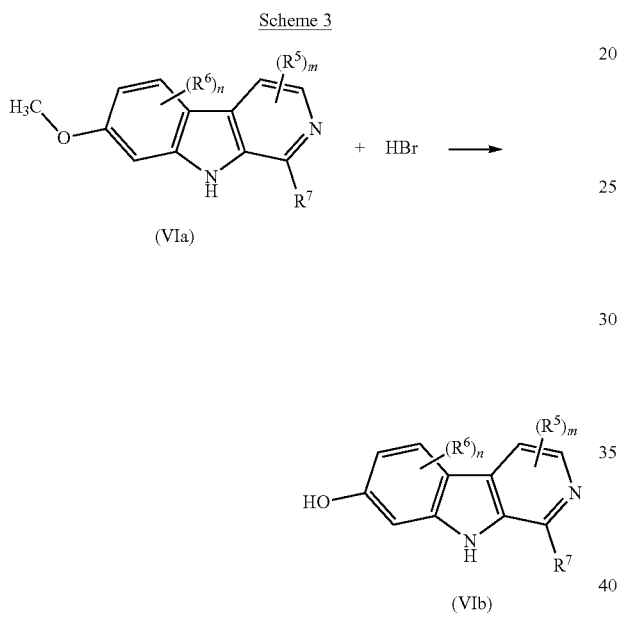

Compounds of Formula (Ia1) wherein $R^2$-$L^2$- and $R^3$-$L^3$- are the same (further, $Z^1$ is —O— and $R^4$-$L^4$-$Z^2$ is hydrogen and the remaining substituents have the same meaning as that defined above) may be prepared as shown in Scheme 4 by reacting the compound of Formula (Ib1) as defined above with the compound $R^1$-$L^1$-$G^a$ (wherein $R^1$ and $L^1$ have meanings as defined above), wherein $G^a$ is an appropriate leaving group, such as preferably halo, more preferably bromo or iodo, in a polar aprotic solvent such as THF, to yield said compound of Formula (Ia1).

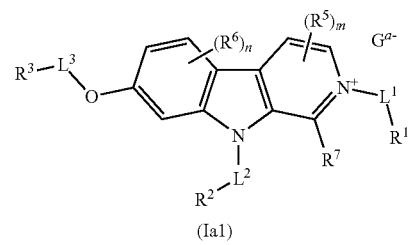

(Ia1)

Compounds of Formula (Ib2) wherein $R^3$-$L^3$-$Z^1$— is —OH (further, $R^4$-$L^4$-$Z^2$ is hydrogen and the remaining substituents have the same meaning as that defined above) may be prepared as shown in Scheme 5 by hydrogenating the compound of Formula (Ia1) as defined above in a suitable protic solvent, such as alcohol preferably methanol, to yield said compound of Formula (Ib2).

Compounds of Formula (Ib3) wherein $R^2$-$L^2$- and $R^3$-$L^3$- may be the same or different (further, $Z^1$ is —O— and $R^4$-$L^4$-$Z^2$ is hydrogen and the remaining substituents have the same meaning as that defined above) may be prepared as shown in Scheme 6 by reacting a compound of Formula (Ib2) as defined above with the compound $R^3$-$L^3$-$G^1$ (wherein $R^3$ and $L^3$ have meanings as defined above), wherein $G^1$ is an appropriate leaving group, such as preferably halo, more preferably bromo or iodo, under basic conditions, to yield said compound of Formula (Ib3).

-continued

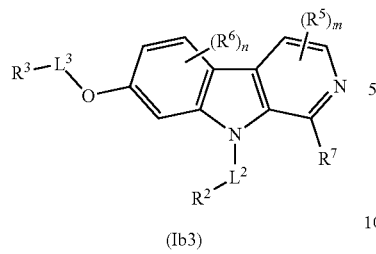
(Ib3)

Compounds of Formula (Ia2) wherein $R^2$-$L^2$- and $R^3$-$L^3$- may be the same or different (further, $Z^1$ is —O— and $R^4$-$L^4$-$Z^2$ is hydrogen and the remaining substituents have the same meaning as that defined above) may be prepared as shown in Scheme 7 by reacting the compound of Formula (Ib3) as defined above with the compound $R^1$-$L^1$-$G^a$ (wherein $R^1$ and $L^1$ have meanings as defined above), wherein $G^a$ is an appropriate leaving group, such as preferably halo, more preferably bromo or iodo, in a polar aprotic solvent such as THF, to yield said compound of Formula (Ia2).

Scheme 7

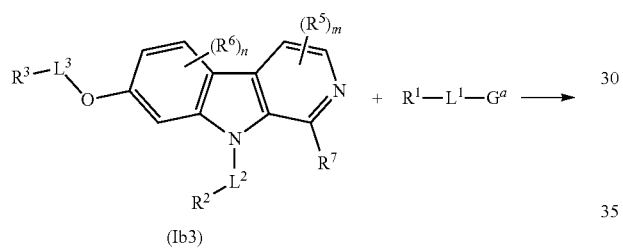

Compounds of Formula (Ib4) wherein m is 0 and the remaining substituents have the same meaning as that defined above may be prepared as shown in Scheme 8 by Pictet-Spengler cyclisation and dehydrogenation reaction of the compound of Formula (VIc) with the aldehyde $R^7$—CHO, in a suitable polar aprotic solvent such as DCM, using a suitable imine formation catalyst such as K-10 and a hydrogenation catalyst such as Pd/C, to yield said compound of Formula (Ib4), e.g., as described in Tetrahedron Letters 2009, 50(16), 1791-1794.

Scheme 8

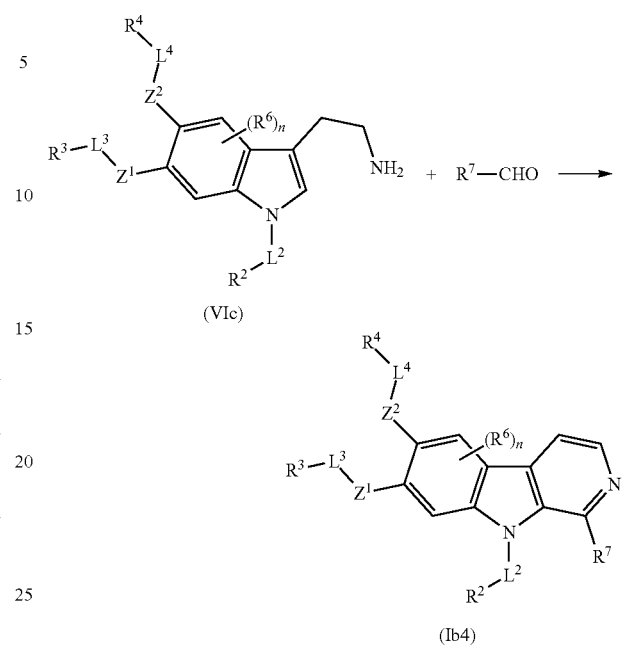

Compounds of Formula (Ib4) wherein m is 0 and the remaining substituents have the same meaning as that defined above may be prepared as shown in Scheme 9 by cyclisation and dehydrogenation reaction of the compound of Formula (VIc).HCl with the compound $R^7$—C(=O)COOH, in a suitable polar protic solvent such as methanol, using cumene hydroperoxide and a suitable catalyst such as Pd, to yield said compound of Formula (Ib4), e.g., as described in Bioorganic & Medicinal Chemistry Letters, 16(22), 5840-5843, 2006.

Scheme 9

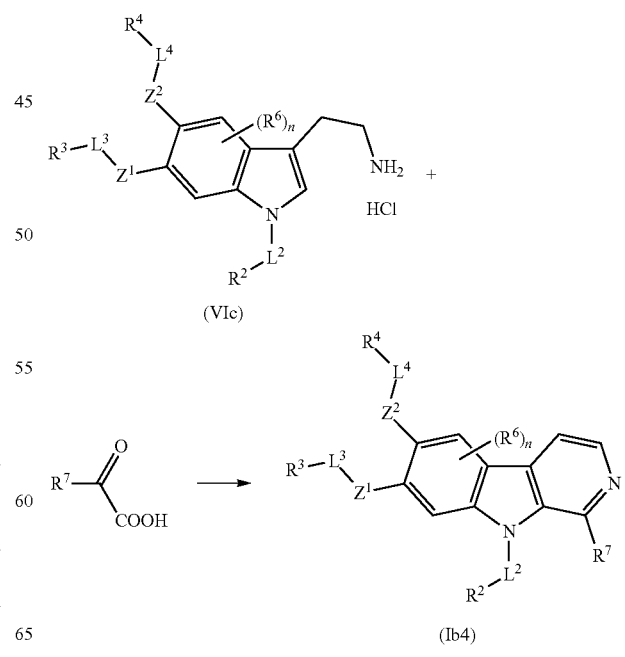

Compounds of Formula (Ib5) wherein m and n is 0, $R^2$-$L^2$- and $R^3$-$L^3$-$Z^1$ are hydrogen and the remaining substituents have the same meaning as that defined above and preferably $Z^2$ is —S— may be prepared as shown in Scheme 10 by bromination of the compound of Formula (VId) using a bromination reagent such as N-bromosuccinimide, thereby yielding the compound of formula (VIe), and subsequently reacting the latter with the reagent $R^4L^4Z^2H$ in a basic environment, to yield said compound of Formula (Ib5), e.g., as described for introduction of benzylthio group in Journal of Heterocyclic Chemistry, 38(5), 1087-1095; 2001.

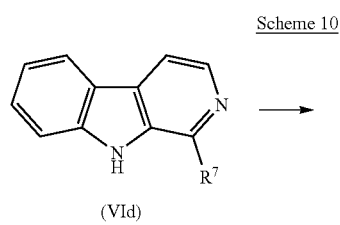

Compound of Formula (Ib5) wherein m and n is 0, $R^2$-$L^2$- and $R^3$-$L^3$-$Z^1$ are hydrogen and the remaining substituents have the same meaning as that defined above and preferably $Z^2$ is —S—, and compound of Formula (Ib6) wherein m and n is 0, $R^2$-$L^2$- and $R^4$-$L^4$-$Z^2$ are hydrogen and the remaining substituents have the same meaning as that defined above and preferably $Z^1$ is —S—, may be prepared as shown in Scheme 11 by introducing the $F_3C$—$S(=O)_2O$ group on the ring system of the compounds of Formula (VIf) or (VIh) using a suitable reagent such as $(CF_3SO_2)_2O$, thereby yielding the compounds of formula (VIg) or (VIj), and subsequently reacting the latter with the reagent $R^4L^4Z^2H$ or $R^3L^3Z^1H$, to yield said compounds of Formula (Ib5) or (Ib6), respectively, e.g., as described for introduction of benzylthio group in Organic Letters, 10(13), 2617-2620; 2008.

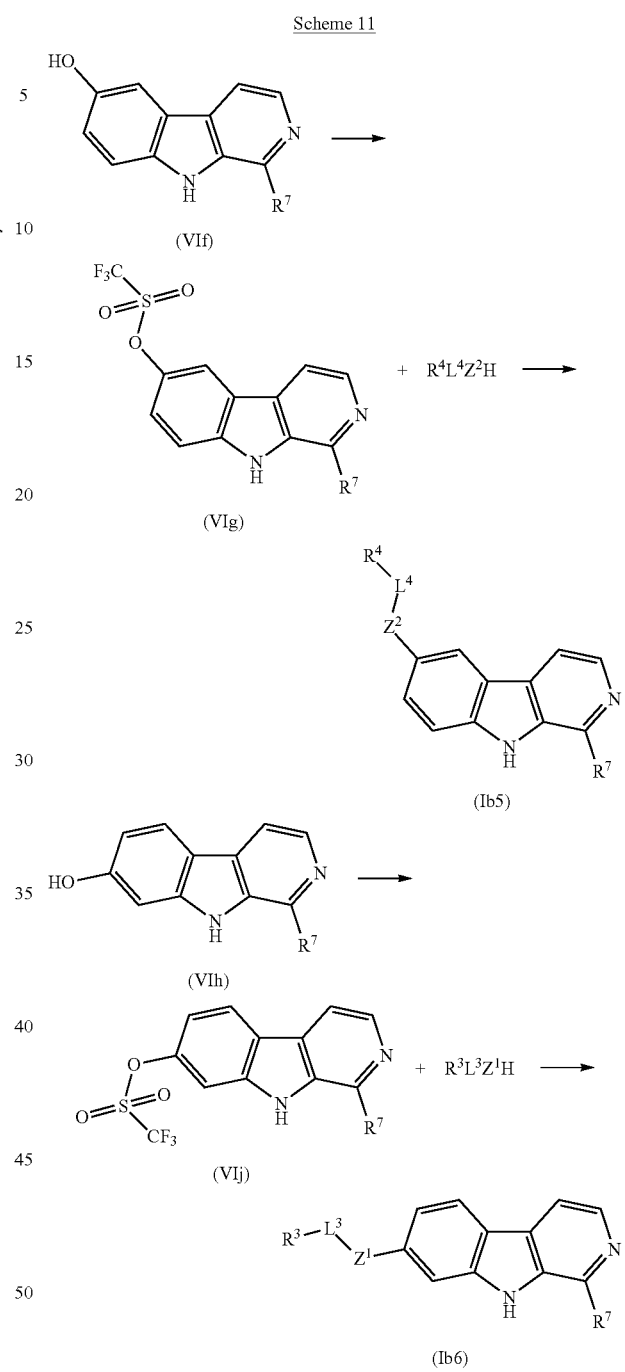

Compounds of Formula (Ib9) wherein m and n is 0, $R^2$-$L^2$- is hydrogen and the remaining substituents have the same meaning as that defined above, and $R^7$ is $C_{1-6}$alkyoxymethyl, and preferably $Z^1$ and $Z^2$ are —O— may be prepared as shown in Scheme 12 by bromination of the methyl group at position 1 of the compound of Formula (Ib9) using a bromination reagent such as N-bromosuccinimide, thereby yielding the compound of formula (Ib8), and subsequently reacting the latter with alcohol reagent $C_{1-6}$alkyl-OH in a basic environment, to yield said compound of Formula (Ib9), e.g., as described in Bioorganic & Medicinal Chemistry Letters, 19(20), 5931-5935; 2009.

Scheme 12

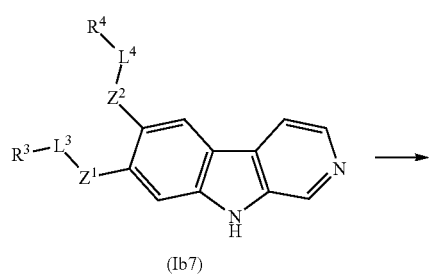
(Ib7)

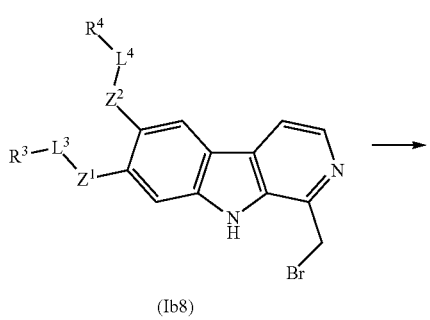
(Ib8)

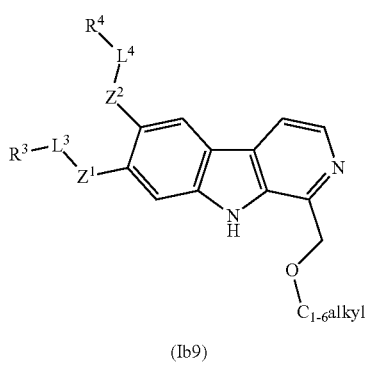
(Ib9)

Compounds of Formula (Ib2) wherein $R^3$-$L^3$-$Z^1$— is —OH (further, $R^4$-$L^4$-$Z^2$ is hydrogen and the remaining substituents have the same meaning as that defined above) may also be prepared as shown in Scheme 13 by hydrogenating the compound of Formula (Ib1) as defined above in a suitable protic solvent, such as alcohol preferably methanol, to yield said compound of Formula (Ib2).

Scheme 13

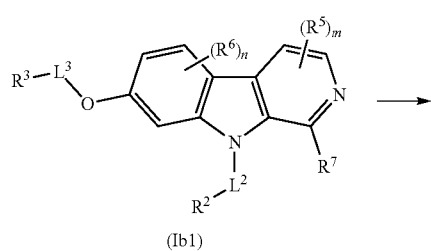
(Ib1)

-continued

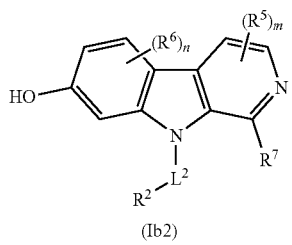
(Ib2)

Compounds of Formula (Ib4) wherein $R^2$-$L^2$- is —H (further, $Z^1$ is —O— and $R^4$-$L^4$-$Z^2$ is hydrogen and the remaining substituents have the same meaning as that defined above) may be prepared as shown in Scheme 14 by reacting a compound of Formula (VIb) with the compound $R^3$-$L^3$-$G^1$ (wherein $R^3$ and $L^3$ have meanings as defined above), wherein $G^1$ is an appropriate leaving group, such as preferably halo, more preferably bromo or iodo, under basic conditions, to yield said compound of Formula (Ib4).

Scheme 14

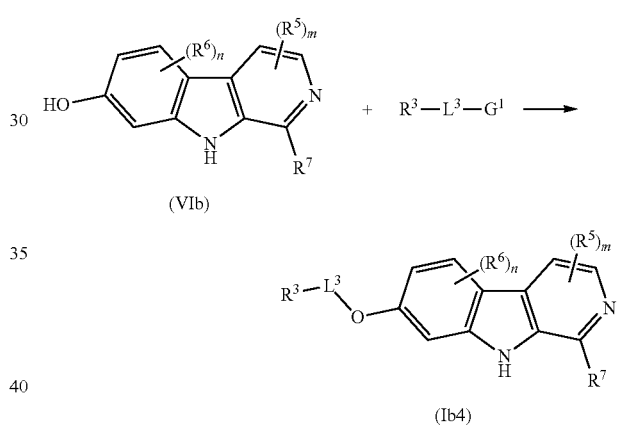

Compounds of Formula (Ib3) wherein $R^2$-$L^2$- and $R^3$-$L^3$- may be the same or different (further, $Z^1$ is —O— and $R^4$-$L^4$-$Z^2$ is hydrogen and the remaining substituents have the same meaning as that defined above) may also be prepared as shown in Scheme 15 by reacting a compound of Formula (Ib4) as defined above with the compound $R^2$-$L^2$-$G^1$ (wherein $R^2$ and $L^2$ have meanings as defined above), wherein $G^1$ is an appropriate leaving group, such as preferably halo, more preferably bromo or iodo, under basic conditions, to yield said compound of Formula (Ib3).

Scheme 15

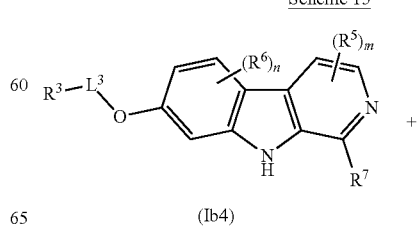
(Ib4)

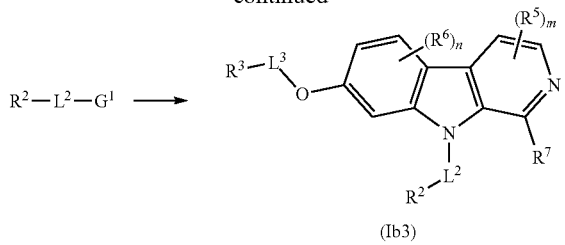

(Ib3)

Any of the intermediates, such as those of formulas (VIa) or (VIb) can be commercially available, or can be prepared as described hereunder in the example section.

More specific examples for the synthesis of compounds of Formulas (Ia) or (Ib) and subgroups thereof are provided in the examples hereinafter.

Compounds of Formulas (Ia) or (Ib), any subgroup thereof, addition salts, solvates, and stereochemical isomeric forms thereof can be converted into further compounds according to the invention using procedures known in the art.

It has been found that the beta carboline derivative compounds described herein have anti-tumour and anti-cancer activity and are useful in the treatment of proliferative disorders in subjects.

Except when noted, "subject" or "patient" are used interchangeably and refer to animals, preferably warm-blooded animals, more preferably vertebrates, even more preferably mammals, still more preferably primates, and specifically include human patients and non-human mammals and primates. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients are human subjects.

As used herein, a phrase such as "a subject in need of treatment" includes subjects that would benefit from treatment of a recited disease or condition. Such subjects may include, without limitation, those that have been diagnosed with said disease or condition, those prone to contract or develop said disease or condition and/or those in whom said disease or condition is to be prevented. Particularly intended are patients diagnosed with a proliferative disease such as tumour or cancer.

As used herein, the terms "treat" or "treatment" refer to both therapeutic treatment and prophylactic or preventative measures, wherein the object is to prevent or slow down (lessen) an undesired physiological change or disorder, such as the development or spread of proliferative disease, e.g., cancer. Beneficial or desired clinical results include, but are not limited to, alleviation of symptoms, diminishment of extent of disease, stabilised (i.e., not worsening) state of disease, delay or slowing of disease progression, reduction or prevention of neoplastic cell migration and colonisation of new tissues (i.e., anti-migratory effect), amelioration or palliation of the disease state, remission (whether partial or total), whether detectable or undetectable. "Treatment" can also mean prolonging survival as compared to expected survival if not receiving treatment. Particularly intended herein are therapeutic or curative treatments of proliferative disorders such as tumours or cancer.

The term "therapeutically effective amount" refers to an amount of a compound or pharmaceutical composition as described herein effective to treat a disease or disorder in a subject, i.e., to obtain a desired local or systemic effect and performance. By means of example and not limitation, in the case of proliferative disease, e.g., cancer, therapeutically effective amount of a drug may reduce the number of cancer cells; reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; enhance efficacy of another cancer therapy; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). The term thus refers to the quantity of compound or pharmaceutical composition that elicits the biological or medicinal response in a tissue, system, animal, or human that is being sought by a researcher, veterinarian, medical doctor or other clinician, which includes alleviation of the symptoms of the cancer being treated. In particular, these terms refer to the quantity of compound or pharmaceutical composition according to the invention which is necessary to prevent, cure, ameliorate, or at least minimize the clinical impairment, symptoms, or complications associated with cancer in either a single or multiple doses.

By "proliferative disease or disorder" is meant all neoplastic cell growth and proliferation, whether malignant or benign, including all transformed cells and tissues and all cancerous cells and tissues. Proliferative diseases or disorders include, but are not limited to, premalignant or precancerous lesions, abnormal cell growths, benign tumours, malignant tumours, and cancer.

Additional examples of proliferative diseases and/or disorders include, but are not limited to neoplasms, whether benign or malignant, located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract. In a preferred embodiment, the proliferative disorder involves tumour.

As used herein, the terms "tumour" or "tumour tissue" refer to an abnormal mass of tissue that results from excessive cell division. A tumour or tumour tissue comprises "tumour cells" which are neoplastic cells with abnormal growth properties and no useful bodily function. Tumours, tumour tissue and tumour cells may be benign or malignant. A tumour or tumour tissue may also comprise "tumour-associated non-tumour cells", e.g., vascular cells which form blood vessels to supply the tumour or tumour tissue. Non-tumour cells may be induced to replicate and develop by tumour cells, for example, the induction of angiogenesis in a tumour or tumour tissue. In another preferred embodiment, the proliferative disorder involves malignancy or cancer.

As used herein, the term "malignancy" refers to a non-benign tumour or a cancer. As used herein, the term "cancer" connotes a type of proliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, hematological cancer. The term "cancer" includes primary malignant cells or tumours (e.g., those whose cells have not migrated to sites in the subject's body other than the site of the original malignancy or tumour) and secondary malignant cells or tumours (e.g., those arising from metastasis, the migration of malignant cells or tumour cells to secondary sites that are different from the site of the original tumour).

Preferably, said cancer is selected from non-small cell lung cancer, CNS cancer, melanoma, ovarian cancer, kidney cancer, prostate cancer, breast cancer, colon cancer, bladder cancer, sarcoma, pancreatic cancer, colorectal cancer, head and neck cancer, liver cancer, stomach cancer, oesophageal cancer, or lymphoma.

Most preferably, said cancer is selected from colon cancer; prostate cancer; breast cancer; head and neck cancer; glioma, preferably glioblastoma or non-small-cell lung cancer (NSCLC) and apoptosis resistant cancer cells in the general meaning of the term.

Apoptosis resistant cancer cells means cancer cells that are resistant to apoptosis and that cannot be killed by pro-apoptotic drugs.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumour, and any other proliferative disease, besides neoplasia, located in an organ system listed above.

In a further embodiment, the proliferative disorder is premalignant condition. Premalignant conditions are known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell 1976 (Basic Pathology, 2d Ed., W. B. Saunders Co., Philadelphia, pp. 68-79).

"Hyperplasia" is a form of controlled cell proliferation, involving an increase in cell number in a tissue or organ, without significant alteration in structure or function. Hyperplastic disorders which can be treated by the method of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

"Metaplasia" is a form of controlled cell growth in which one type of adult or fully differentiated cell substitutes for another type of adult cell. Metaplastic disorders which can be treated by the method of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

"Dysplasia" is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be treated by the method of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders include, but are not limited to, benign dysproliferative disorders (e.g., benign tumours, fibrocystic conditions, tissue hypertrophy, intestinal polyps, colon polyps, and oesophageal dysplasia), leukoplakia, keratoses, Bowen's disease, Farmer's Skin, solar cheilitis, and solar keratosis.

In preferred embodiments, the proliferative disorder is chosen from glioma, preferably glioblastoma; prostate cancer; non-small-cell lung cancer (NSCLC); melanoma, head and neck cancer, pancreas cancer or colon cancer. By showing the anti-proliferative effect of the compounds of the invention on cell-lines derived from each of these cancer-types, the inventors realised that the above cancer types can particularly benefit from the methods and agents of the invention.

As used herein, the term "glioma" refers to its art-recognised connotation. By virtue of further illustration and not limitation, the term "glioma" refers to a tumour originating in the neuroglia of the brain or spinal cord. Gliomas can be derived from glial cell types, such as, e.g., astrocytes and oligodendrocytes, thus gliomas include astrocytomas and oligodendrogliomas, as well as anaplastic gliomas, glioblastomas, and ependymonas. Astrocytomas and ependymomas can occur in all areas of the brain and spinal cord in both children and adults. Oligodendrogliomas typically occur in the cerebral hemispheres of adults. Malignant astrocytic gliomas are associated with the worst prognoses because of their ability to infiltrate diffusely into the normal brain parenchyma and include World Health Organization (WHO) grades II, III and grade IV tumors.

As used herein, the term "glioblastoma" refers to its art-recognised connotation. By virtue of further illustration and not limitation, glioblastoma may also be known as "glioblastoma multiforme" (GBM) or as "grade 4 astrocytoma" and represents perhaps the most common and aggressive type of malignant primary brain tumour.

As used herein, the term "prostate cancer" (CaP) refers to its art-recognised connotation. By virtue of illustration and not limitation, the term "prostate cancer" refers to both the appearance of a palpable tumour of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. Cancer cells are generally found in the prostates of men who live into their seventies or eighties, however not all of these men develop prostate cancer. In the event that prostate cancer metastasises to additional sites distal to the prostate, the condition is described as metastatic cancer (MC), to distinguish this condition from organ-confined prostate cancer. CaP fatality typically results from metastatic dissemination of prostatic adenocarcinoma cells to distant sites, usually in the axial skeleton.

The term "non-small-cell lung cancer" (NSCLC) refers to its art-recognised connotation. By means of exemplification and not limitation, the term encompasses any of subtypes thereof, i.e., adenocarcinoma of the lung, squamous cell carcinoma of the lung and large cell carcinoma of the lung.

The term "colon cancer" refers to its art-recognised connotation. By means of illustration and not limitation, the term "colon cancer" refers to cancers arising in the large intestine (including both the colon and rectum) of any histologic type, including but not limited to malignant epithelial tumours. As used herein the term colon cancer thus encompasses colorectal cancer. Malignant epithelial tumours of the large intestine may be divided into five major histologic types: adenocarcinoma, mucinous adenocarcinoma (also termed colloid adenocarcinoma), signet ring adenocarcinoma, scirrhous tumours and carcinoma simplex. Colon cancer is staged using any of several classification systems known in the art. The Dukes system is one of the most often employed staging systems. See Dukes and Bussey 1958 (Br J Cancer 12: 309).

The present active substances may be used alone or in combination with any anti-proliferative (e.g., anti-tumour or anti-cancer) therapies known in the art ("combination therapy"). The term "active substance" encompasses the compounds disclosed herein, or the stereoisomeric forms thereof or the pharmaceutically acceptable addition salts, hydrates or solvates thereof.

Combination therapies as contemplated herein may comprise the administration of at least one active substance as taught herein and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The at least one "other pharmaceutically or biologically active ingredient" particularly refers to a substance other than the compounds described herein which is effective to treat a proliferative disorder such as a tumour or cancer. Said at least one other pharmaceutically or biologically active ingredient may be particularly suited for the treatment of a preferred proliferative disorder as defined herein, such as for example, non-small cell lung cancer, prostate cancer (more preferably refractory prostate cancer), breast cancer (preferably triple-negative breast cancer, i.e., breast cancer not expressing oestrogen receptor (ER), progesterone receptor (PR) and Her2/neu), glioma preferably glioblastoma, colon cancer and melanoma.

Said at least one other pharmaceutically or biologically active ingredient may be, without limitation, selected from radiation therapeutics or chemotherapeutics, including but not limited to temozolomide, vincristine, vinorelbine, procarbazine, carmustine, lomustine, taxol, taxotere, tamoxifen, retinoic acid, 5-fluorouracil, cyclophosphamide and thalidomide.

For example, the administration of at least one active substance as taught herein may be performed in combination with an anti-tumour or anti-cancer therapy selected from chemotherapy, radiation therapy, immunotherapy, gene therapy, surgery, and combinations thereof.

The primary modes of treatment of solid tumor cancers may comprise surgery, radiation therapy, and chemotherapy, separately and in combination. The active substances described herein are suitable for use in combination with these medicinal techniques. For example, the active substances described herein may be useful in increasing the sensitivity of tumor cells to radiation in radiotherapy and also in potentiating or enhancing damage to tumors by chemotherapeutic agents. The active substances may also be useful for sensitizing multidrug-resistant tumor cells. The active substances according to the invention are useful therapeutic compounds for administration in conjunction with DNA-damaging cytotoxic drugs or radiation used in radiotherapy to potentiate their effect.

The various active substances of the present disclosure, or the stereoisomeric forms thereof or the pharmaceutically acceptable addition salts, hydrates or solvates thereof, may be formulated into pharmaceutical compositions or formulations with one or more pharmaceutically acceptable carriers/excipients. The pharmaceutical compositions may comprise one or more active substances as disclosed herein. The pharmaceutical compositions may also further comprise one or more other pharmaceutically or biologically active ingredients as defined above.

As used herein, "carrier" or "excipient" includes any and all solvents, diluents, buffers (such as, e.g., neutral buffered saline, phosphate buffered saline, or optionally Tris-HCl, acetate or phosphate buffers), solubilisers (such as, e.g., Tween 80, Polysorbate 80), colloids, dispersion media, vehicles, fillers, chelating agents (such as, e.g., EDTA or glutathione), amino acids (such as, e.g., glycine), proteins, disintegrants, binders, lubricants, wetting agents, stabilisers, emulsifiers, sweeteners, colorants, flavourings, aromatisers, thickeners, agents for achieving a depot effect, coatings, antifungal agents, preservatives (such as, e.g., Thimerosal™, benzyl alcohol), antioxidants (such as, e.g., ascorbic acid, sodium metabisulfite), tonicity controlling agents, absorption delaying agents, adjuvants, bulking agents (such as, e.g., lactose, mannitol) and the like. The use of such media and agents for pharmaceutical active substances is well known in the art. Except insofar as any conventional media or agent is incompatible with the active substance(s), its use in the therapeutic compositions may be contemplated. Suitable pharmaceutical carriers are described inter alia in Remington's Pharmaceutical Sciences, 18th ed., Mack Publishing Co., Easton, Pa. (1990).

In a preferred embodiment, the pharmaceutical composition or preparation according to the invention is administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories, parenterally, for example subcutaneously, intramuscularly, intravenously or intrasternally in the form of solutions for injection or infusion, percutaneous or topical administration, for example in the form of ointments, tinctures, sprays or transdermal therapeutic systems, or the inhalative administration in the form of nasal sprays or aerosol mixtures, or, for example, microcapsules, implants or rods.

The pharmaceutical composition can be prepared in a manner known per se to one of skill in the art. For this purpose, at least one active substance as disclosed herein, one or more solid or liquid pharmaceutical excipients and, if desired, in combination with one or more other pharmaceutically or biologically active ingredients as defined above, are brought into a suitable administration form or dosage form which can then be used as a pharmaceutical in human medicine or veterinary medicine.

By means of non-limiting examples, such a formulation may be in a form suitable for oral administration, for parenteral administration (such as by intravenous, intramuscular, or subcutaneous injection, or intravenous infusion), for topical administration (including ocular), for administration by inhalation, by a skin patch, by an implant, by a suppository, etc. Such suitable administration forms—which may be solid, semi-solid, or liquid, depending on the manner of administration—as well as methods and carriers, diluents and excipients for use in the preparation thereof, will be clear to the skilled person; reference is made to for instance U.S. Pat. Nos. 6,372,778, 6,369,086, 6,369,087, and 6,372,733, as well as to the standard handbooks, such as the latest edition of Remington's Pharmaceutical Sciences.

As non-limiting examples, the active substance(s), together with one or more solid or liquid pharmaceutical carrier substances and/or additives (or auxiliary substances) and, if desired, in combination with one or more other pharmaceutically or biologically active ingredients as defined above, are brought into a suitable administration form or dosage form which can then be used as a pharmaceutical in human medicine. For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the active substance(s) and to use the resulting lyophilisates, for example, for preparing preparations for injection or infusion. Suitable carriers for microcapsules, implants or rods are, for example, copolymers of glycolic acid and lactic acid.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate, and lactose and/or other excipients, binders, extenders, disintegrants, diluents, and lubricants known in the art.

The oral administration of a pharmaceutical composition comprising at least one active substance as disclosed herein, is suitably accomplished by uniformly and intimately blending together a suitable amount of said compound in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Compressed tablets containing the pharmaceutical composition described herein can be prepared by uniformly and intimately mixing the active substance(s) with a solid carrier such as described above to provide a mixture having the necessary compression properties, and then compacting the mixture in a suitable machine to the shape and size desired. Molded tablets maybe made by molding in a suitable machine, a mixture of powdered active substance(s) moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions, or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the active substance(s) described herein, if desired with the substances customary therefore such as solubilizers, emulsifiers, or further auxiliaries, are brought into solution, suspension, or emulsion. The active substance(s) can also be lyophilized and the lyophilizates obtained used, for example, for the production of injection or infusion preparations. Suitable solvents are, for example, water, physiological saline solution, or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents, or solvents, such as mannitol, 1,3-butanediol, water, Ringer's solution, or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the active substance(s) described herein with a suitable non-irritating excipient, such as cocoa butter, synthetic glyceride esters, or polyethylene glycols, which are solid at ordinary temperatures, but liquefy and/or dissolve in the rectal cavity to release the drug.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying, and suspending agents, dispersing agents, desintegrants, bulking agents, fillers, preserving agents, sweetening agents, flavoring agents, flow regulators, release agents, etc. The compositions may also be formulated so as to provide rapid, sustained, or delayed release of the active compound(s) contained therein, for example using liposomes or hydrophilic polymeric matrices based on natural gels or synthetic polymers.

Preferably, the present composition is administered in a GLP/GMP solvent.

The dosage or amount of active substances as disclosed herein used, optionally in combination with one or more other pharmaceutically or biologically active ingredients as defined above, depends on the individual case and is, as is customary, to be adapted to the individual circumstances to achieve an optimum effect. Thus, it depends on the nature and the severity of the disorder to be treated, and also on the sex, age, body weight, diet, general health, individual responsiveness of the human or animal to be treated, on the efficacy, metabolic stability and duration of action of the compounds used, on mode and time of administration, rate of excretion, on whether the therapy is acute or chronic or prophylactic, or on whether other pharmaceutically or biologically active ingredients as defined above are administered, or other therapies applied, in addition to the active substance(s) of the invention.

Without limitation, depending on the type and severity of the disease, a typical daily dosage might range from about 1 µg/kg to about 250 mg/kg body weight or more, preferably from about 1 µg/kg to about 100 mg/kg body weight, more preferably from about 0.01 mg/kg to about 50 mg/kg body weight, even more preferably from about 0.01 mg/kg to about 10 mg/kg body weight, and still more preferably from about 0.05 mg/kg to about 10 mg/kg body weight or from about 0.05 mg/kg to about 1 mg/kg body weight, depending on the factors mentioned above.

For repeated administrations over several days or longer, depending on the condition, the treatment is sustained until a desired suppression of disease symptoms occurs. A preferred dosage of the agent may be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered as a single daily dose, divided over one or more daily doses, or essentially continuously, e.g., using a drip infusion, or intermittently, e.g., every week or every three weeks.

The pharmaceutical preparations disclosed herein are preferably in a unit dosage form, and may be suitably packaged, for example in a box, blister, vial, bottle, sachet, ampoule, or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one active substance of the invention, e.g., about 10, 25, 50, 100, 200, 300, or 400 mg per unit dosage.

Depending on the mode of administration, the pharmaceutical composition will preferably comprise from 0.05 to 99% by weight, more preferably from 0.1 to 70% by weight, even more preferably from 0.1 to 50% by weight of the active substance(s) as described herein, and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical compositions can be administered separately at different times during the course of therapy or concurrently in divided or single combination forms. The present disclosure embraces all such regimes of simultaneous or alternating treatment and the term "administering" is to be interpreted accordingly.

The administration may be performed with food, e.g., a high-fat meal. The term "with food" means the consumption of a meal either during or no more than about one hour before or after administration of a pharmaceutical composition as described herein.

The following non-limiting examples illustrate the present invention.

EXAMPLES

Example 1

Synthesis of the Compounds According to the Invention

General Techniques

Melting points were measured by DSC with a Perkin Elmer DSC 7.0 Pro apparatus, and recorded with Pyris software. NMR spectra were recorded on a Jeol spectrometer (JNM ECX 400). The $^1$H-NMR, $^{13}$C-NMR and $^{19}$F-NMR spectra were recorded at 400, 100 and 376 MHz, respectively. The chemical shifts were reported in parts per million (ppm) relative to the singlet at 7.26 ppm for chloroform in CDCl$_3$, relative to the singlet at 2.50 ppm for dimethyl sulfoxide in (CD$_3$)$_2$SO, relative to the singlet at 3.31 ppm for methanol in CD$_3$OD, and the coupling constants are in Hz. The following abbreviations are used for spin multiplicity: s, singlet; d, doublet; t, triplet; q, quadruplet; qt, quintuplet; m, multiplet; b, broad. Routine thin layer chromatography (TLC) was performed on silica gel plates (Silicagel GF254® from VWR). Column chromatography was performed on BiotageSP1 25+M column (flow=25 mL/min) (spherical particle size 60-200 µm from MP Biomedicals) equipped with a UV-spectrophotometer as detector (wavelengths=254 and 320 nm). Solvents from Aldrich and VWR were used without further purification.

Scheme 1

Exemplary compounds of the invention having general Formulas (Vc), (Vd), (Ve), (Vf) and (Vg) as shown in Scheme 1, wherein $R^1$-$L^1$-, $R^2$-$L^2$-, $R^3$-$L^3$- are as defined elsewhere in this specification, whereas $Z^1$ is —O—, $R^4$-$L^4$-$Z^2$ is hydrogen, n and m are 0, $R^7$ is methyl, and $X^-$ is $Br^-$, were prepared using reactions a. to h. as generally shown in Scheme 1. Reaction b. leads to compounds (Vc) and (Vd) in which $R^2$-$L^2$- and $R^3$-$L^3$- are the same. However, reaction d. allows to remove the $R^3$-$L^3$- group from the compounds (Vc) yielding compounds (Vg), whereby another group $R^3$-$L^3$- different from the $R^2$-$L^2$- group can then be added to said compounds (Vg) using reaction g. to obtain compounds (Vf). Another pathway is to use reaction e. to add a group $R^3$-$L^3$ yielding compounds (Ve), on which another group $R^2$-$L^2$ can be added by using reaction f. to obtain compounds (Vf). Finally, compounds (Vf) allow to obtain compounds (Vd) by reaction h. whereby $R^1$-$L^1$, $R^2$-$L^2$ and $R^3$-$L^3$ can be different from each other. The individual steps of Scheme 1 are set out below in additional detail.

Scheme 1 harmine;
1-Methyl-7-methoxy-β-carboline;
7-Methoxy-1-methyl-9H-pyrido[3,4-b]indole

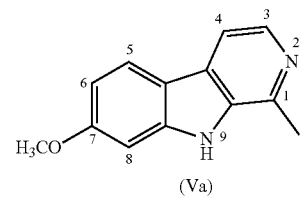

(Va)

harmol
1-Methyl-7-hydroxy-β-carboline;
7-Hydroxy-1-methyl-9H-pyrido[3,4-b]indole HBr
HAc
a.

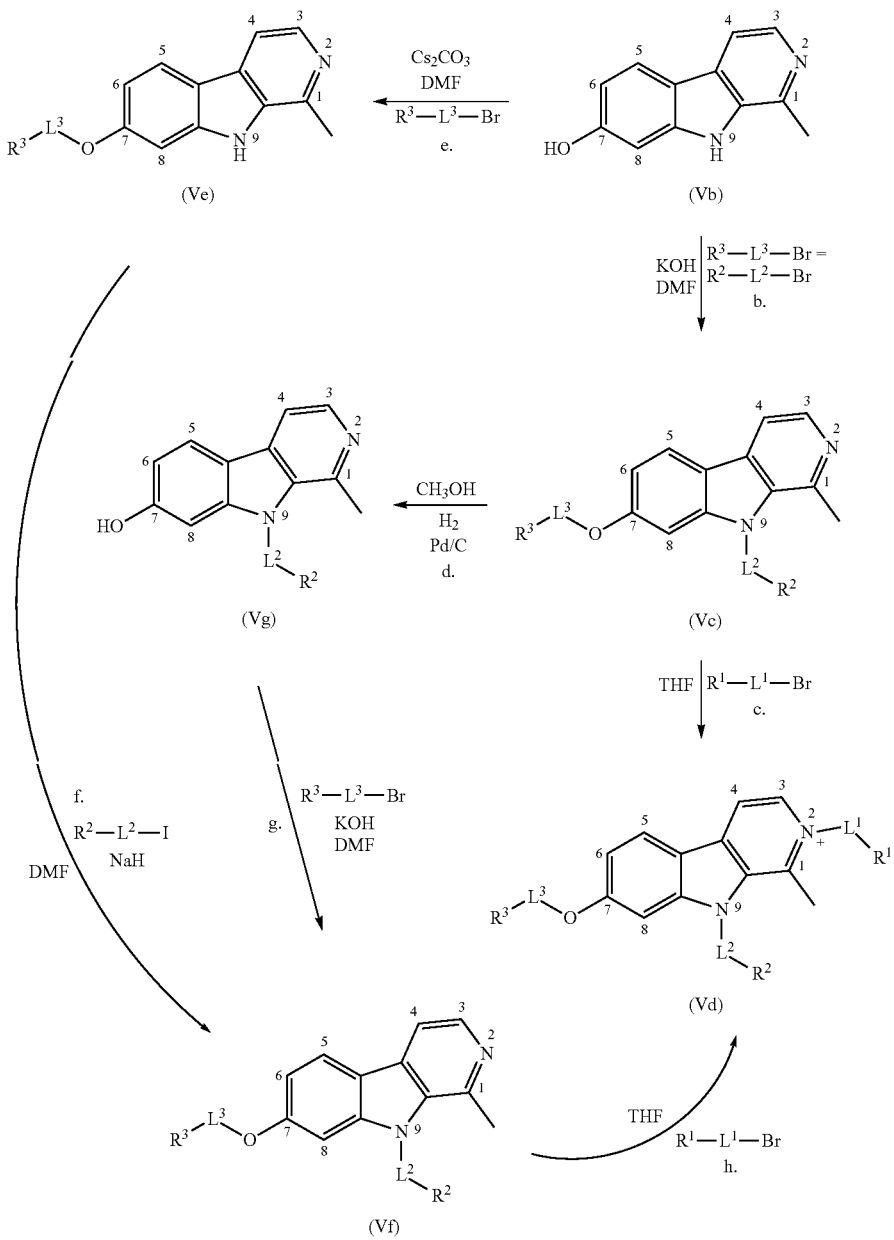

Synthesis of 1-methyl-7-hydroxy-β-carboline
(Reaction a. of Scheme 1)

According to reaction a. of Scheme 1, 1-methyl-7-methoxy-β-carboline (5 g, 23.56 mmol) is mixed with acetic acid (100 mL) and bromhydric acid 47% w/v (100 mL) and refluxed for 15 h under argon atmosphere. The reaction mixture is then diluted with distilled water (1 L). The solvents are eliminated under reduced pressure to give 1-methyl-7-hydroxy-β-carboline.

White solid; Yield=100%; Rf=0.35 (CH$_2$Cl$_2$/ethanol 8/2); Melting point=248° C.

NMR $^1$H (400 MHz, DMSO-d$_6$) δ (ppm): 2.92 (s, 3H, CH$_3$), 6.88 (dd, J$_{6-5}$=8.7 Hz, J$_{6-8}$=2.1 Hz, 1H, H-6), 6.99 (d, J$_{8-6}$=2.1 Hz, 1H, H-8), 8.23 (d, J$_{5-6}$=8.7 Hz, 1H, H-5), 8.33 (d, J$_{3-4}$=6.4 Hz, 1H, H-3), 8.37 (d, J$_{4-3}$=6.2 Hz, 1H, H-4), 10.43 (s, 1H, O—H), 12.45 (s, 1H, N—H).

NMR $^{13}$C (100 MHz, DMSO-d$_6$) δ (ppm): 16.30 (CH$_3$), 96.95 (C-8), 113.18 (C$_q$), 113.31 (C-6), 114.04 (C-4), 125.10 (C-5), 128.96 (C-3), 132.79 (C$_q$), 133.93 (C$_q$), 136.78 (C$_q$), 146.13 (C$_q$), 161.75 (C$_q$).

General Procedure for Simultaneous O$_7$- and N$_9$-alkylation of 1-methyl-7-hydroxy-β-carboline
(Reaction b. of Scheme 1)

According to reaction b. of Scheme 1, 1-methyl-7-hydroxy-β-carboline (500 mg, 1.587 mmol) is dissolved in N,N-dimethylformamide (20 mL), five equivalents of potassium hydroxide are added, and the mixture is stirred for 30 minutes under argon atmosphere. Then, two equivalents of R$^2$-L$^2$-Br and R$^3$-L$^3$-Br which are identical (in particular, arylmethyl bromide, substituted or not, cycloalkylmethyl bromide or alkyl bromide) are added, and the mixture is stirred at room temperature for 24 h under argon atmosphere. The reaction is followed by TLC (CH$_2$Cl$_2$/ethanol 85/15). At the end of the reaction, the reaction mixture is extracted by dichloromethane (30 mL). The organic layer is washed twice with brine (2×30 mL), dried with MgSO$_4$ which is collected by filtration. The organic layer was finally evaporated under reduced pressure to give the crude product which is purified by column chromatography as described in the general section with a mobile phase of cyclohexane/ethyl acetate (from 80/20 to 50/50) as eluant.

Synthesis of Compound CV9/JR84 (See Table 1): 1-methyl-7-benzyloxy-9-benzyl-β-carboline The title compound was synthesized from 1-methyl-7-hydroxy-β-carboline (1 g, 3.173 mmol) in presence of 1-bromomethylbenzene (1.085 g, 6.346 mmol) as described here above.

White powder; Yield=66%; Rf=0.88 (CH$_2$Cl$_2$/ethanol 85/15); Molecular formula=C$_{26}$H$_{22}$N$_2$O; Melting point=156° C.; Mass spectra: [M+1]=379.2 m/z NMR $^1$H (400 MHz, DMSO-d$_6$) δ (ppm): 2.70 (s, 3H, CH$_3$), 5.14 (s, 2H, O—CH$_2$), 5.84 (s, 2H, N—CH$_2$), 6.88 (d, 2H, 2ArH), 6.94 (dd, J$_{6-5}$=8.7 Hz, J$_{6-8}$=2.1 Hz, 1H, H-6), 7.17-7.43 (m, 9H, H-8+8ArH), 7.89 (d, J$_{4-3}$=5.0 Hz, 1H, H-4), 8.11 (d, J$_{5-6}$=8.7 Hz, 1H, H-5), 8.14 (d, J$_{3-4}$=5.0 Hz, 1H, H-3).

NMR $^{13}$C (100 MHz, DMSO-d$_6$) δ (ppm): 23.21 (CH$_3$), 47.78 (N—CH$_2$), 70.24 (O—CH$_2$), 95.46 (C-8), 110.44 (C-6), 112.93 (C-4), 114.96 (Cq), 123.11 (C-5), 125.86 (2C—ArH), 127.63 (C—ArH), 128.41 (C—ArH), 128.48 (C—ArH), 128.93 (C—ArH), 129.08 (C$_q$), 129.34 (C—ArH), 135.52 (C$_q$), 137.38 (C$_q$), 138.68 (C-3), 139.51 (C$_q$), 141.35 (C$_q$), 143.78 (C$_q$), 160.25 (C$_q$).

Synthesis of Compound CV5 (See Table 1): 1-methyl-7-(3-fluorobenzyloxy)-9-(3-fluorobenzyl)-β-carboline The title compound was synthesized from 1-methyl-7-hydroxy-β-carboline (0.5 g, 1.587 mmol) in presence of 1-bromomethyl-3-fluorobenzene (0.6 g, 3.173 mmol) as described here above.

Yellow powder; Yield=85%; Rf=0.78 (CH$_2$Cl$_2$/ethanol 85/15); Molecular formula=C$_{26}$H$_{20}$F$_2$N$_2$O; Melting point=148° C.; Mass spectra: [M+1]=415.1 m/z NMR $^1$H (400 MHz, DMSO-d$_6$) δ (ppm): 2.70 (s, 3H, CH$_3$), 5.18 (s, 2H, O—CH$_2$), 5.87 (s, 2H, N—CH$_2$), 6.64 (d, 1H, J=7.8 Hz, ArH), 6.72 (d, 1H, J=10.1 Hz, ArH), 6.97 (dd, 1H, J$_{6-5}$=8.7 Hz, J$_{6-8}$=1.4 Hz, H-6), 7.01-7.13 (m, 2H, 2ArH), 7.26-7.40 (m, 5H, H-8+4ArH), 7.91 (d, 1H, J$_{4-3}$=5.0 Hz, 1H, H-4), 8.15 (d, 1H, J$_{5-6}$=8.9 Hz, H-5), 8.16 (d, 1H, J$_{3-4}$=5.5 Hz, H-3).

NMR $^{13}$C (100 MHz, DMSO-d$_6$) δ (ppm): 23.18 (CH$_3$), 47.36 (N—CH$_2$), 69.36 (O—CH$_2$), 95.45 (C-8), 110.57 (C-6), 112.76 (d, J=22.0 Hz, C—ArH), 113.01 (C-4), 114.52 (d, J=20.1 Hz, C—ArH), 114.96 (d, J=22.0 Hz, C$_q$), 115.07 (C$_q$), 115.16 (d, J=18.2 Hz, C—ArH), 121.78 (d, J=1.9 Hz, C—ArH), 123.25 (C-5), 124.26 (d, J=2.9 Hz, C—ArH), 129.13 (C$_q$), 130.94 (d, J=8.6 Hz, C—ArH), 131.48 (d, J=8.6 Hz, C—ArH), 135.41 (C$_q$), 138.87 (C-3), 140.33 (d, J=7.7 Hz, C$_q$), 141.34 (C$_q$), 142.59 (d, J=6.7 Hz, C$_q$), 143.64 (C$_q$), 160.06 (C$_q$), 162.69 (d, J=244.4 Hz, C$_q$), 162.94 (d, J=244.4 Hz, C$_q$).

NMR $^{19}$F (376 MHz, DMSO-d$_6$) δ (ppm): −112.58 (s), −113.04 (s).

Synthesis of Compound CV11 (See Table 1): 1-methyl-7-(4-fluorobenzyloxy)-9-(4-fluorobenzyl)-β-carboline The title compound was synthesized from 1-methyl-7-hydroxy-β-carboline (0.5 g, 1.587 mmol) in presence of 1-bromomethyl-4-fluorobenzene (0.6 g, 3.173 mmol) as described here above.

Brown powder; Yield=62%; Rf=0.67 (CH$_2$Cl$_2$/ethanol 85/15); Molecular formula=C$_{26}$H$_{20}$F$_2$N$_2$O; Melting point=175° C.; Mass spectra: [M+1]=415.0 m/z NMR $^1$H (400 MHz, DMSO-d$_6$) δ (ppm): 2.71 (s, 3H, CH$_3$), 5.13 (s, 2H, O—CH$_2$), 5.83 (s, 2H, N—CH$_2$), 6.89-6.95 (m, 3H, H-6+2ArH), 7.05-7.20 (m, 4H, 4ArH), 7.27 (d, 1H, J$_{8-6}$=1.8 Hz, H-8), 7.46-7.49 (m, 2H, 2ArH), 7.90 (d, 1H, J$_{4-3}$=5.0 Hz, H-4), 8.13 (d, 1H, J$_{5-6}$=8.7 Hz, H-5), 8.16 (d, 1H, J$_{3-4}$=5.3 Hz, H-3).

NMR $^{13}$C (100 MHz, DMSO-d$_6$) δ (ppm): 23.22 (CH$_3$), 47.12 (N—CH$_2$), 69.48 (O—CH$_2$), 95.49 (C-8), 110.54 (C-6), 112.97 (C-4), 115.03 (C$_q$), 115.74 (d, J=22.0 Hz, 2C—ArH), 116.15 (d, J=21.1 Hz, 2C—ArH), 123.17 (C-5), 127.85 (d, J=8.6 Hz, 2C—ArH), 129.12 (C$_q$), 130.69 (d, J=8.6 Hz, 2C—ArH), 133.62 (d, J=2.9 Hz, C$_q$), 135.41 (C$_q$), 135.59 (d, J=2.9 Hz, C$_q$), 138.77 (C-3), 141.30 (C$_q$), 143.60 (C$_q$), 160.13 (C$_q$), 161.77 (d, J=242.5 Hz, C$_q$), 162.30 (d, J=243.5 Hz, C$_q$).

NMR $^{19}$F (376 MHz, DMSO-d$_6$) δ (ppm): −114.28 (s), −115.68 (s).

Synthesis of Compound CV12 (See Table 1): 1-methyl-7-cyclohexylmethyloxy-9-cyclohexylmethyl-β-carboline The title compound was synthesized from 1-methyl-7-hydroxy-β-carboline (0.5 g, 1.587 mmol) in presence of 1-bromomethylcyclohexane (1.240 g, 3.173 mmol) as described here above.

White powder; Yield=75%; Rf=0.71 (CH$_2$Cl$_2$/ethanol 85/15); Molecular formula=C$_{26}$H$_{34}$N$_2$O; Melting point=152° C.; Mass spectra: [M+1]=391.2 m/z NMR $^1$H (400 MHz, DMSO-d$_6$) δ (ppm): 1.04-1.34 (m, 12H, 12ArH), 1.56-1.82 (m, 10H, 10ArH), 2.88 (s, 3H, CH$_3$), 3.90 (d, 2H, J=6.18 Hz, O—CH$_2$), 4.36 (d, 2H, 7.10 Hz, N—CH$_2$), 6.81 (dd, 1H, J$_{6-5}$=8.7 Hz, J$_{6-8}$=1.8 Hz, H-6), 7.15 (d, 1H, J$_{8-6}$=1.8 Hz, H-8), 7.83 (d, 1H, J$_{4-3}$=5.0 Hz, H-4), 8.02 (d, 1H, J$_{5-6}$=8.7 Hz, H-5), 8.12 (d, 1H, J$_{3-4}$=5.0 Hz, H-3).

NMR $^{13}$C (100 MHz, DMSO-d$_6$) δ (ppm): 23,74 (CH$_3$), 25,91 (2CH(cyclohexyl)), 26.36 (CH(cyclohexyl)), 26.61 (CH(cyclohexyl)), 29.92 (CH(cyclohexyl)), 30.58 (CH(cyclohexyl)), 37.75 (CH(cyclohexyl)), 50.10 (N—CH$_2$), 73.62 (O—CH$_2$), 95.60 (C-8), 109.93 (C-6), 112.73 (C-4), 114.35 (C$_q$), 122.75 (C-5), 129.11 (C$_q$), 135.32 (C$_q$), 138.19 (C-3), 141.06 (C$_q$), 144.11 (C$_q$), 160.33 (C$_q$).

Synthesis of Compound PL3: 1-methyl-7-(3-methylbutyloxy)-9-(3-methylbutyl)-β-carboline The title compound was synthesized from 1-methyl-7-hydroxy-β-carboline (1.504 g, 4.770 mmol) in presence of 1-bromo-3-methylbutane (1.440 g, 9.520 mmol) as described here above.

White powder; Yield=69%; Rf=0.82 (CH$_2$Cl$_2$/ethanol 85/15); Molecular formula=C$_{22}$H$_{30}$N$_2$O; Melting point=106.4° C.; Mass spectra: [M+1]=339.3 m/z NMR $^1$H (400 MHz, CD$_3$OD) δ (ppm): 0.98-1.00 (m, 12H, CH—(CH$_3$)$_2$, overlapped), 1.55-1.93 (m, 6H, O—CH$_2$—CH$_2$—CH(CH$_3$)$_2$ et N—CH$_2$—CH$_2$—CH(CH$_3$)$_2$), 2.90 (s, 3H, CH$_3$), 4.10 (t, 2H, J=6.5 Hz, N—CH$_2$), 4.39 (m, 2H, O—CH$_2$), 6.34 (dd, 1H, J=8.7 Hz, 8.5 Hz, H-6), 6.87 (d, 1H, J=1.8 Hz, H-8), 7.76 (d, 1H, J$_{4-3}$=5.3 Hz, H-4), 7.94 (d, 1H, J$_{5-6}$=8.7 Hz, H-5), 8.05 (d, 1H, J$_{3-4}$=5.5 Hz, H-3).

NMR $^{13}$C (100 MHz, CD$_3$OD) δ (ppm): 21.21 (CH$_3$), 21.63 (N—CH$_2$—CH$_2$—CH(CH$_3$)$_2$), 21.67 (O—CH$_2$—CH$_2$—CH(CH$_3$)$_2$), 25.01 (N—CH$_2$—CH$_2$—CH(CH$_3$)$_2$), 26.11 (O—CH$_2$—CH$_2$—CH(CH$_3$)$_2$), 37.87 (N—CH$_2$—CH$_2$—CH(CH$_3$)$_2$), 38.98 (O—CH$_2$—CH$_2$—CH(CH$_3$)$_2$), 42.91 (N—CH$_2$—CH$_2$—CH(CH$_3$)$_2$), 66.50 (O—CH$_2$—CH$_2$—CH(CH$_3$)$_2$), 93.38 (C-8), 109.73 (C$_q$), 112.19 (C-6), 114.56 (C-4), 122.14 (C-5) 130.01 (C-3), 134.95 (C$_q$), 136.70 (C$_q$), 140.11 (C$_q$), 143.45 (C$_q$), 160.89 (C$_q$).

General Procedure for N$_2$-alkylation of 1-methyl-O$_7$-substituted-N$_9$-substituted-7-hydroxy-β-carboline (Reaction c. of Scheme 1)

According to reaction c. of Scheme 1,1-methyl-O$_7$-substituted-N$_9$-substituted-7-hydroxy-β-carboline (100 mg) is dissolved in tetrahydrofurane (15 mL), ten equivalents of R$^1$-L$^1$-Br (in particular, 1-bromomethylbenzene, substituted or not, 1-bromomethylcycloalkane, or 1-bromomethylalkane) are added, and the mixture is refluxed for 48 h under argon atmosphere. The reaction is followed by TLC (CH$_2$Cl$_2$/ethanol 85/15). At the end of the reaction, the solvents are evaporated under reduced pressure to give the crude product which is purified by column chromatography as described in the general section with a mobile phase of dichloromethane/ethanol (95/5) as eluant.

Synthesis of Compound CV21/JR95 (See Table 1): 1-methyl-2-benzyl-7-benzyloxy-9-benzyl-β-carbolin-2-ium bromide The title compound was synthesized from CV9 (0.07 g, 0.185 mmol) in presence of 1-bromomethylbenzene (0.316 g, 1.850 mmol) as described here above.

Yellow powder; Yield=36%; Rf=0.30 (CH$_2$Cl$_2$/ethanol 85/15); Molecular formula=C$_{33}$H$_{29}$BrN$_2$O; Melting point=262° C.; Mass spectra: [M+1]=469.3 m/z NMR $^1$H (400 MHz, DMSO-d$_6$) δ (ppm): 2.81 (s, 3H, CH$_3$), 5.23 (s, 2H, O—CH$_2$), 5.96 (s, 2H, N—CH$_2$), 5.98 (s, 2H, N—CH$_2$), 6.94 (d, 2H, J=7.1 Hz, ArH), 7.07 (d, 2H, J=7.1 Hz, ArH), 7.18-7.45 (m, 12H, 11ArH+H-6), 7.53 (s, 1H, H-8), 8.45 (d, 1H, J$_{5-6}$=8.7 Hz, H-5), 8.69 (d, 1H, J$_{4-3}$=6.4 Hz, H-4), 8.82 (d, 1H, J$_{3-4}$=6.2 Hz, H-3).

NMR $^{13}$C (100 MHz, DMSO-d$_6$) δ (ppm): 16.57 (CH$_3$), 48.84 (N—CH$_2$), 60.33 (N—CH$_2$), 70.67 (O—CH$_2$), 95.55 (C-8), 113.39 (C$_q$), 114.28 (C-6), 115.23 (C-4), 125.44 (C-5), 125.98 (C—ArH), 127.13 (C—ArH), 128.05 (C—ArH), 128.65 (C—ArH), 128.86 (C—ArH), 129.01 (C—ArH), 129.56 (C—ArH), 129.63 (C—ArH), 133.99 (C$_q$), 135.28 (C$_q$), 135.89 (C$_q$), 136.75 (C-3), 136.77 (C$_q$), 138.10 (C$_q$), 140.14 (C$_q$), 148.51 (C$_q$), 163.38 (C$_q$).

Synthesis of Compound CV18 (See Table 1): 1-methyl-2-(2-fluorobenzyl)-7-benzyloxy-9-benzyl-β-carbolin-2-ium bromide The title compound was synthesized from CV9 (0.07 g, 0.185 mmol) in presence of 1-bromomethyl-2-fluorobenzene (0.35 g, 1.850 mmol) as described here above.

Yellow powder; Yield=55%; Rf=0.58 (CH$_2$Cl$_2$/ethanol 85/15); Molecular formula=C$_{33}$H$_{28}$BrFN$_2$O; Melting point=>200° C.; Mass spectra: [M+1]=487.2 m/z RMN $^1$H (400 MHz, CD$_3$OD) δ (ppm): 2.94 (s, 3H, CH$_3$), 5.21 (s, 2H, O—CH$_2$), 5.93 (s, 2H, N—CH$_2$), 5.97 (s, 2H, N—CH$_2$), 6.98-7.01 (m, 3H, 3ArH), 7.15-7.34 (m, 10H, 8ArH+H-6+H-8), 7.40-7.45 (m, 3H, 3ArH), 8.34 (d, 1H, J$_{5-6}$=8.7 Hz, H-5), 8.48 (d, 1H, J$_{4-3}$=6.6 Hz, H-4), 8.61 (d, 1H, J$_{3-4}$=6.6 Hz, H-3).

RMN $^{13}$C (100 MHz, CD$_3$OD) δ (ppm): 15.40 (CH$_3$), 48.78 (N—CH$_2$), 54.91 (d, J=3.8 Hz, N—CH$_2$), 70.40 (O—CH$_2$), 94.35 (C-8), 113.30 (C$_q$), 114.18 (C-4), 114.47 (C-6), 115.79 (d, J=21.1 Hz, C—ArH), 121.30 (d, J=14.4 Hz, C$_q$), 124.35 (C-5), 125.09 (d, J=3.8 Hz, C—ArH), 125.20 (2C—ArH), 127.51 (2C—ArH), 127.72 (C—ArH), 127.88 (C—ArH), 128.29 (2C—ArH), 128.68 (d, J=2.9 Hz, C—ArH), 129.05 (2C—ArH), 131.13 (d, J=8.6 Hz, C—ArH), 134.53 (C$_q$), 135.71 (C-3), 136.03 (C$_q$), 136.32 (C$_q$), 136.80 (C$_q$), 139.43 (C$_q$), 148.84 (C$_q$), 160.34 (d, J=245.4 Hz, C$_q$), 163.93 (C$_q$).

RMN $^{19}$F (376 MHz, CD$_3$OD) δ (ppm): −118.46 (s).

Synthesis of Compound CV17 (See Table 1): 1-methyl-2-(4-fluorobenzyl)-7-benzyloxy-9-benzyl-β-carbolin-2-ium bromide The title compound was synthesized from CV9 (0.07 g, 0.185 mmol) in presence of 1-bromomethyl-4-fluorobenzene (0.35 g, 1.850 mmol) as described here above.

Yellow powder; Yield=50%; Rf=0.35 (CH$_2$Cl$_2$/ethanol 85/15); Molecular formula=C$_{33}$H$_{28}$BrFN$_2$O; Melting point=>200° C.; Mass spectra: [M+1]=487.2 m/z NMR $^1$H (400 MHz, CD$_3$OD) δ(ppm): 2.90 (s, 3H, CH$_3$), 5.21 (s, 2H, O—CH$_2$), 5.90 (s, 2H, N—CH$_2$), 5.93 (s, 2H, N—CH$_2$), 6.97-7.41 (m, 16H, H-6, H-8, 14ArH), 8.34 (d, 1H, J$_{5-6}$=8.9 Hz, H-5), 8.50 (d, 1H, J$_{4-3}$=6.4 Hz, H-4), 8.62 (d, 1H, J$_{3-4}$=6.4 Hz, H-3).

NMR $^{13}$C (100 MHz, CD$_3$OD) δ (ppm): 15.36 (CH$_3$), 48.80 (N—CH$_2$), 59.67 (N—CH$_2$), 70.40 (O—CH$_2$), 94.36 (C-8), 113.29 (Cq), 114.27 (C-4), 114.44 (C-6), 115.98 (d, J=22 Hz, 2C—ArH), 124.33 (C-5), 125.21 (2C—ArH), 127.50 (2C—ArH), 127.70 (C—ArH), 127.87 (Cq-ArH), 128.28 (2C—ArH), 128.78 (d, J=7.7 Hz, 2C—ArH), 129.05 (2C—ArH), 130.22 (d, J=2.9 Hz, Cq), 134.52 (Cq), 135.64 (C-3), 136.11 (Cq), 136.33 (Cq), 136.86 (Cq), 148.79 (Cq), 162.86 (247.3 Hz, Cq), 163.88 (Cq).

NMR $^{19}$F (376 MHz, CD$_3$OD) δ (ppm): −114.79 (s).

Synthesis of Compound CV23 (See Table 1): 1-methyl-2-benzyl-7-(4-fluorobenzyl)oxy-9-(4-fluorobenzyl)-β-carbolin-2-ium bromide The title compound was synthesized from CV11 (0.100 g, 0.241 mmol) in presence of 1-bromomethylbenzene (412 g, 2.410 mmol) as described here above.

Yellow powder; Yield=72%; Rf=0.40 (CH$_2$Cl$_2$/ethanol 85/15); Molecular formula=C$_{33}$H$_{27}$BrF$_2$N$_2$O; Melting point=>200° C.; Mass spectra: [M+1]=585.48 m/z NMR $^1$H (400 MHz, CD$_3$OD) δ (ppm): 2.90 (s, 3H, CH$_3$), 5.21 (s, 2H, O—CH$_2$), 5.92 (s, 2H, N—CH$_2$), 5.93 (s, 2H, N—CH$_2$), 6.97-7.45 (m, 15H, H-6, H-8, 13ArH), 8.35 (d, 1H, J$_{5-6}$=8.9 Hz, H-5), 8.51 (d, 1H, J$_{4-3}$=6.4 Hz, H-4), 8.64 (d, 1H, J$_{3-4}$=6.6 Hz, H-3).

NMR $^{13}$C (100 MHz, CD$_3$OD) δ (ppm): 15.38 (CH$_3$), 48.22 (N—CH$_2$), 60.44 (N—CH$_2$), 69.65 (O—CH$_2$), 94.39 (C-8), 113.40 (Cq), 114.27 (C-4), 114.42 (C-6), 114.98 (d, J=22.0 Hz, 2C—ArH), 115.76 (d, J=22.0 Hz, 2C—ArH), 124.40 (C-5), 126.41 (2C—ArH), 127.23 (d, J=7.7 Hz, 2C—ArH), 128.58 (C—ArH), 129.20 (2C—ArH), 129.59 (d, J=8.6 Hz, 2C—ArH), 132.42 (d, J=2.9 Hz, Cq), 132.76 (d, J=3.8 Hz, Cq), 134.19 (Cq), 134.59 (Cq), 135.86 (C-3), 136.03 (Cq), 139.49 (Cq), 148.59 (Cq), 162.41 (d, J=246.3 Hz, Cq), 162.65 (d, J=245.4 Hz, Cq) 163.70 (Cq).

NMR $^{19}$F (376 MHz, CD$_3$OD) δ (ppm): −116.02 (s), −116.39 (s).

Synthesis of Compound CV25 (See Table 1): 1-methyl-2-(2-fluorobenzyl-7-(4-fluorobenzyl)oxy-9-(4-fluorobenzyl)-β-carbolin-2-ium bromide The title compound was synthesized from CV11 (0.110 g, 0.265 mmol) in presence of 1-bromomethyl-2-fluorobenzene (0.502 g, 2.650 mmol) as described here above.

Yellow powder; Yield=56%; Rf=0.43 (CH$_2$Cl$_2$/ethanol 85/15); Molecular formula=C$_{33}$H$_{26}$BrF$_3$N$_2$O; Melting point=>200° C.; Mass spectra: [M+1]=523.0 m/z NMR $^1$H (400 MHz, CD$_3$OD) δ (ppm): 2.94 (s, 3H, CH$_3$), 5.21 (s, 2H, O—CH$_2$), 5.92 (s, 2H, N—CH$_2$), 5.98 (s, 2H, N—CH$_2$), 7.00-7.06 (m, 7H, 7ArH), 7.16-7.23 (m, 4H, H-8, H-6, 2ArH), 7.40-7.45 (m, 3H, 3ArH), 8.34 (d, 1H, J$_{5-6}$=8.7 Hz, H-5), 8.48 (d, 1H, J$_{4-3}$=6.6 Hz, H-4), 8.62 (d, 1H, J$_{3-4}$=6.4 Hz, H-3).

NMR $^{13}$C (100 MHz, CD$_3$OD) δ (ppm): 15.28 (CH$_3$), 48.25 (N—CH$_2$), 54.96 (d, J=4.8 Hz, N—CH$_2$), 69.65 (O—CH$_2$), 94.40 (C-8), 113.38 (Cq), 114.24 (C-4), 114.46 (C-6), 114.98 (d, J=22.0 Hz, 2C—ArH), 115.77 (d, J=22,0 Hz, 2C—ArH), 115.79 (d, J=21.1 Hz, C—ArH), 121.29 (d, J=11.5 Hz, Cq), 124.44 (C-5), 125.09 (d, J=2.9 Hz, C—ArH), 127.26 (d, J=7.7 Hz, 2C—ArH), 128.78 (d, J=1.9 Hz, C—ArH), 129.58 (d, J=8.6 Hz, 2C—ArH), 131.14 (d, J=8.6 Hz, C—ArH), 132.41 (d, J=2.9 Hz, Cq), 132.76 (d, J=2.9 Hz, Cq), 134.63 (Cq), 135.83 (C-3), 135.95 (Cq), 139.64 (Cq), 148.67 (Cq), 160.16 (d, J=207.0 Hz, Cq), 162.53 (d, J=224.3 Hz, Cq), 162.73 (d, J=226.2 Hz, Cq), 163.75 (Cq).

NMR $^{19}$F (376 MHz, CD$_3$OD) δ (ppm): −116.05 (s), −116.40 (s), −118.43 (s).

Synthesis of Compound CV29 (See Table 1): 1-methyl-2-(4-fluorobenzyl)-7-(4-fluorobenzyl)oxy-9-(4-fluorobenzyl)-β-carbolin-2-ium bromide The title compound was synthesized from CV11 (0.100 g, 0.241 mmol) in presence of 1-bromomethyl-4-fluorobenzene (0.456 g, 2.410 mmol) as described here above.

Yellow powder; Yield=63%; Rf=0.24 (CH$_2$Cl$_2$/ethanol 85/15); Molecular formula=C$_{33}$H$_{26}$BrF$_3$N$_2$O; Melting point=>200° C.; Mass spectra: [M+1]=523.0 m/z RMN $^1$H (400 MHz, CD$_3$OD) δ (ppm): 2.92 (s, 3H, CH$_3$), 5.20 (s, 2H, O—CH$_2$), 5.92 (s, 4H, 2N—CH$_2$), 6.98-7.22 (m, 12H, H-6+H-8+10ArH), 7.41-7.45 (m, 2H, 2ArH), 8.34 (d, 1H, J$_{5-6}$=8.9 Hz, H-5), 8.50 (d, 1H, J$_{4-3}$=6.6 Hz, H-4), 8.63 (d, 1H, J$_{3-4}$=6.6 Hz, H-3).

RMN $^{13}$C (100 MHz, CD$_3$OD) δ (ppm): 15.44 (CH$_3$), 48.23 (N—CH$_2$), 59.72 (N—CH$_2$), 69.67 (O—CH$_2$), 94.45 (C-8), 113.40 (C$_q$), 114.35 (C-4), 114.42 (C-6), 114.97 (d, J=22.0 Hz, 2C—ArH), 115.76 (d, J=22.0 Hz, 2C—ArH), 115.98 (d, J=23.0 Hz, 2C—ArH), 124.41 (C-5), 127.26 (d, J=8.6 Hz, 2C—ArH), 128.85 (d, J=8.6 Hz, 2C—ArH), 129.56 (d, J=8.6 Hz, 2C—ArH), 130.19 (d, J=2.9 Hz, C$_q$), 132.42 (d, J=2.9 Hz, C$_q$), 132.75 (d, J=2.9 Hz, C$_q$), 134.61 (C$_q$), 135.74 (C-3), 136.09 (C$_q$), 139.51 (C$_q$), 148.61 (C$_q$), 162.43 (d, J=246.3 Hz, C$_q$), 162.64 (d, J=245.4 Hz, C$_q$), 162.89 (d, J=247.3 Hz, C$_q$), 163.70 (C$_q$).

RMN $^{19}$F (376 MHz, CD$_3$OD) δ (ppm): 114.73 (s), 116.05 (s), 116.40 (s).

Synthesis of Compound CV16 (See Table 1): 1-methyl-2-benzyl-7-(3-fluorobenzyl)oxy-9-(3-fluorobenzyl)$_{43}$-carbolin-2-ium bromide The title compound was synthesized from CV5 (0.07 g, 0.169 mmol) in presence of 1-bromomethylbenzene (0.289 g, 1.690 mmol) as described here above.

Yellow powder; Yield=26%; Rf=0.43 (CH$_2$Cl$_2$/ethanol 85/15); Molecular formula=C$_{33}$H$_{27}$BrF$_2$N$_2$O; Melting point=>200° C.; Mass spectra: [M+1]=505.3 m/z;

NMR $^1$H (400 MHz, DMSO-d$_6$) δ (ppm): 2.90 (s, 3H, CH$_3$), 5.25 (s, 2H, O—CH$_2$), 5.94 (s, 2H, N—CH$_2$), 5.95 (s, 2H, N—CH$_2$), 6.73 (d, 1H, J=9.4 Hz, ArH), 6.78 (d, 1H, J=7.3 Hz, ArH), 6.98-7.38 (m, 13H, H-6+H-8+11ArH), 8.37 (d, 1H, J$_{5-6}$=9.4 Hz, H-5), 8.52 (d, 1H, J$_{4-3}$=6.6 Hz, H-4), 8.65 (d, 1H, J$_{3-4}$=6.6 Hz, H-3).

NMR $^{13}$C (100 MHz, DMSO-d$_6$) δ (ppm): 15.33 (CH$_3$), 48.39 (N—CH$_2$), 60.47 (N—CH$_2$), 69.48 (O—CH$_2$), 94.41 (C-8), 112.20 (d, J=23.0 Hz, C—ArH), 113.47 (Cq), 113.88 (d, J=22.0 Hz, C—ArH), 114.39 (C-4+C-6), 114.49 (d, J=21.1 Hz, 2C—ArH), 120.99 (d, J=2.9 Hz, C—ArH), 122.93 (d, J=2.9 Hz, C—ArH), 124.48 (C-5), 126.42 (2C—ArH), 128.58 (C—ArH), 129.21 (2C—ArH), 130.10 (d, J=7.7 Hz, C—ArH), 130.99 (J=8.6 Hz, C—ArH), 134.17 (Cq), 134.62 (Cq), 135.95 (C-3), 136.08 (Cq), 139.22 (d, J=7.7 Hz, Cq), 139.60 (Cq), 139.75 (d, J=6.7 Hz, Cq), 148.54 (Cq), 163.02 (d, J=244.4 Hz, Cq), 163.44 (d, J=246.3 Hz, Cq), 163.60 (Cq).

NMR $^{19}$F (376 MHz, CD$_3$OD) δ (ppm): −113.52 (s), −114.84 (s).

Synthesis of Compound CV19 (See Table 1): 1-methyl-2-(2-fluorobenzyl)-7-(3-fluorobenzyl)oxy-9-(3-fluorobenzyl)-β-carbolin-2-ium bromide The title compound was synthesized from CV5 (0.07 g, 0.169 mmol) in presence of 1-bromomethyl-2-fluorobenzene (0.319 g, 1.690 mmol) as described here above.

Yellow powder; Yield=48%; Rf=0.51 (CH$_2$Cl$_2$/ethanol 85/15); Molecular formula=C$_{33}$H$_{26}$BrF$_3$N$_2$O; Melting point=>200° C.; Mass spectra: [M+1]=523.1 m/z RMN $^1$H (400 MHz, CD$_3$OD) δ (ppm): 2.94 (s, 3H, CH$_3$), 5.25 (s, 2H, O—CH$_2$), 5.95 (s, 2H, N—CH$_2$), 5.98 (s, 2H, N—CH$_2$), 6.74 (d, 1H, J=9.4 Hz, ArH), 6.80 (d, 1H, 7.3 Hz, ArH), 6.98-7.08 (m, 3H, H-6+2ArH), 7.15-7.45 (m, 9H, H-8+8ArH), 8.36 (d, 1H, J$_{5-6}$=9.6 Hz, H-5), 8.49 (d, 1H, J$_{4-3}$=6.6 Hz, H-4), 8.63 (d, J$_{3-4}$=6.6 Hz, H-3).

RMN $^{13}$C (100 MHz, CD$_3$OD) δ (ppm): 15.24 (CH$_3$), 48.40 (N—CH$_2$), 55.00 (d, J=3.8 Hz, N—CH$_2$), 69.47 (O—CH$_2$), 94.41 (C-8), 112.23 (d, J=23.0 Hz, C—ArH), 113.45 (C$_q$), 113.87 (d, J=22.0 Hz, C—ArH), 114.31 (C-4), 114.39 (d, J=2.9 Hz, C—ArH), 114.44 (C-6), 114.60 (d, J=2.9 Hz, C—ArH), 115.80 (d, J=21.09 Hz, C—ArH), 121.01 (d, J=2.9 Hz, C—ArH), 121.27 (d, J=13.4 Hz, C$_q$), 122.93 (d, J=2.9 Hz, C—ArH), 124.51 (C-5), 125.09 (d, J=2.9 Hz, C—ArH), 128.77 (d, J=2.9 Hz, C—ArH), 130.10 (d, J=7.7 Hz, C—ArH), 131.00 (d, J=8.6 Hz, C—ArH), 131.15 (J=8.6 Hz, C—ArH), 134.65 (C$_q$), 135.92 (C-3), 135.99 (C$_q$), 139.21 (d, J=6.7 Hz, C$_q$), 139.69 (C$_q$), 139.73 (d, J=6.7 Hz, C$_q$), 148.62 (C$_q$), 160.37 (d, J=246.3 Hz, C$_q$), 163.00 (d, J=244.4 Hz, C$_q$), 163.44 (d, J=246.3 Hz, C$_q$), 163.65 (C$_q$).

RMN $^{19}$F (376 MHz, CD$_3$OD) δ (ppm): −113.53 (s), −114.85 (s), −118.43 (s).

Synthesis of Compound CV22 (See Table 1): 1-methyl-2-(4-fluorobenzyl)-7-(3-fluorobenzyl)oxy-9-(3-fluorobenzyl)-β-carbolin-2-ium bromide The title compound was synthesized from CV5 (0.125 g, 0.302 mmol) in presence of 1-bromomethyl-4-fluorobenzene (0.570 g, 3.020 mmol) as described here above.

Yellow powder; Yield=92%; Rf=0.43 ($CH_2Cl_2$/ethanol 85/15); Molecular formula=$C_{33}H_{26}BrF_3N_2O$; Melting point=>200° C.; Mass spectra: [M+1]=523.1 m/z RMN $^1$H (400 MHz, $CD_3OD$) δ (ppm): 2.90 (s, 3H, $CH_3$), 5.25 (s, 2H, O—$CH_2$), 5.92 (s, 2H, N—$CH_2$), 5.95 (s, 2H, N—$CH_2$), 6.74 (d, 1H, J=9.6 Hz, ArH), 6.79 (d, 1H, J=7.8 Hz, ArH), 6.97-7.03 (m, 2H, 2ArH), 7.10-7.35 (m, 10H, H-6+H-8+8ArH), 8.37 (d, 1H, $J_{5-6}$=9.4 Hz, H-5), 8.51 (d, 1H, $J_{4-3}$=6.4 Hz, H-4), 8.64 (d, 1H, $J_{3-4}$=6.6 Hz, H-3).

RMN $^{13}$C (100 MHz, $CD_3OD$) δ (ppm): 15.40 ($CH_3$), 49.24 (N—$CH_2$), 59.73 (N—$CH_2$), 69.47 (O—$CH_2$), 94.40 (C-8), 112.23 (d, J=23.0 Hz, C—ArH), 113.45 ($C_q$), 113.87 (d, J=23.0 Hz, C—ArH), 114.41 (C-4+C-6), 114.51 (d, J=15.3 Hz, 2C—ArH), 115.99 (d, J=22.0 Hz, 2C—ArH), 121.01 (d, J=2.9 Hz, C—ArH), 122.93 (d, J=1.9 Hz, C—ArH), 124.50 (C-5), 128.85 (d, J=8.6 Hz, 2C—ArH), 130.10 (d, J=7.7 Hz, C—ArH), 130.19 (d, J=2.9 Hz, $C_q$), 131.00 (d, J=8.6 Hz, C—ArH), 134.61 ($C_q$), 135.81 (C-3), 136.13 ($C_q$), 139.22 (d, J=7.7 Hz, $C_q$), 139.44 ($C_q$), 139.74 (d, J=6.7 Hz, $C_q$), 148.55 ($C_q$), 162.89 (d, J=247.3 Hz, $C_q$), 163.00 (d, J=245.4 Hz, $C_q$), 163.43 (d, J=246.3 Hz, $C_q$), 163.61 ($C_q$).

RMN $^{19}$F (376 MHz, $CD_3OD$) δ (ppm): −113.53 (s), −114.76 (s), −114,87 (s).

Synthesis of Compound CV24 (Ssee Table 1): 1-methyl-2-benzyl-7-cyclohexylmethyloxy-9-cyclohexylmethyl-β-carbolin-2-ium bromide The title compound was synthesized from CV12 (0.125 g, 0.32 mmol) in presence of 1-bromomethylbenzene (0.547 g, 3.200 mmol) as described here above.

Yellow powder; Yield=74%; Rf=0.33 ($CH_2Cl_2$/ethanol 85/15); Molecular formula=$C_{33}H_{41}BrN_2O$; Melting point=>200° C.; Mass spectra: [M+1]=480.3 m/z RMN $^1$H (400 MHz, $CD_3OD$) δ (ppm): 1.07-1.44 (m, 12H, 12CH(cyclohexyl)), 1.61-1.95 (m, 10H, 10CH(cyclohexyl)), 3.10 (s, 3H, $CH_3$), 4.00 (d, 2H, J=6.2 Hz, O—$CH_2$), 4.51 (d, 2H, J=7.3 Hz, N—$CH_2$), 6.00 (s, 2H, N—$CH_2$), 7.08 (dd, 1H, $J_{6-5}$=8.9 Hz, $J_{6-8}$=2.1 Hz, H-6), 7.15-7.16 (m, 2H, 2ArH), 7.23 (d, 1H, $J_{8-6}$=2.1 Hz, H-8), 7.35-7.44 (m, 3H, 3ArH), 8.25 (d, 1H, $J_{5-6}$=8.9 Hz, H-5), 8.43 (d, 1H, $J_{4-3}$=6.6 Hz, H-4), 8.60 (d, 1H, $J_{3-4}$=6.6 Hz, H-3).

RMN $^{13}$C (100 MHz, $CD_3OD$) δ (ppm): 15.62 ($CH_3$), 25.49 (CH(cyclohexyl)), 25.66 (CH(cyclohexyl)), 25.80 (CH (cyclohexyl)), 26.27 (CH(cyclohexyl)), 29.58 (CH(cyclohexyl)), 30.28 (CH(cyclohexyl)), 37.74 (CH(cyclohexyl)), 40.24 (CH(cyclohexyl)), 51.03 (N—$CH_2$), 60.42 (N—$CH_2$), 73.96 (O—$CH_2$), 94.52 (C-8), 112.79 ($C_q$), 113.84 (C-4+C-6), 123.92 (C-5), 126.36 (2C—ArH), 128.58 (C—ArH), 129.25 (2C—ArH), 134.42 ($C_q$), 134.53 ($C_q$), 135.48 (C-3), 135.54 ($C_q$), 139.25 ($C_q$), 149.14 ($C_q$), 164.11 ($C_q$).

Synthesis of Compound CV26 (See Table 1): 1-methyl-2-(2-fluorobenzyl)-7-cyclohexylmethyloxy-9-cyclohexylmethyl-β-carbolin-2-ium bromide The title compound was synthesized from CV12 (0.110 g, 0.282 mmol) in presence of 1-bromomethyl-2-fluorobenzene (0.532 g, 2.820 mmol) as described here above.

Yellow powder; Yield=53%; Rf=0.38 ($CH_2Cl_2$/ethanol 85/15); Molecular formula=$C_{33}H_{40}BrFN_2O$; Melting point=>200° C.; Mass spectra: [M+1]=499.2 m/z RMN $^1$H (400 MHz, $CD_3OD$) δ (ppm): 1.07-1.43 (m, 12H, 12CH(cyclohexyl)), 1.61-1.95 (m, 10H, 10CH(cyclohexyl)), 3.14 (s, 3H, $CH_3$), 4.00 (d, 2H, J=6.2 Hz, O—$CH_2$), 4.53 (d, 2H, J=7.3 Hz, N—$CH_2$), 6.04 (s, 2H, N—$CH_2$), 7.01-7.09 (m, 2H, H-6+1ArH), 7.20-7.27 (m, 3H, H-8+2ArH), 7.43-7.48 (m, 1H, ArH), 8.24 (d, 1H, $J_{5-6}$=8.9 Hz, H-5), 8.42 (d, 1H, $J_{4-3}$=6.6 Hz, H-4), 8.58 (d, 1H, $J_{3-4}$=6.4 Hz, H-3).

RMN $^{13}$C (100 MHz, $CD_3OD$) δ (ppm): 15.51 ($CH_3$), 25.49 (CH(cyclohexyl)), 25.66 (CH(cyclohexyl)), 25.81 (CH (cyclohexyl)), 26.27 (CH(cyclohexyl)), 29.58 (CH(cyclohexyl)), 30.27 (CH(cyclohexyl)), 37.73 (CH(cyclohexyl)), 40.25 (CH(cyclohexyl)), 51.04 (N—$CH_2$), 54.83 (d, J=4.8 Hz, N—$CH_2$), 73.96 (O—$CH_2$), 94.49 (C-8), 112.77 ($C_q$), 113.82 (C-4), 113.92 (C-6), 115.83 (d, J=21.1 Hz, C—ArH), 121.53 (d, J=12.5 Hz, $C_q$), 123.94 (C-5), 125.13 (d, J=3.8 Hz, C—ArH), 128.57 (d, J=2.9 Hz, C—ArH), 131.11 (d, J=8.6 Hz, C—ArH), 134.57 ($C_q$), 135.38 (C-3+$C_q$), 139.32 ($C_q$), 149.24 ($C_q$), 160.36 (d, J=248.24 Hz, $C_q$), 164.17 ($C_q$).

RMN $^{19}$F (376 MHz, $CD_3OD$) δ (ppm): −118.56 (s).

Synthesis of Compound CV30 (See Table 1): 1-methyl-2-(4-fluorobenzyl)-7-cyclohexylmethyloxy-9-cyclohexylmethyl-β-carbolin-2-ium bromide The title compound was synthesized from CV12 (0.100 g, 0.256 mmol) in presence of 1-bromomethyl-4-fluorobenzene (0.484 g, 2.560 mmol) as described here above.

Yellow powder; Yield=76%; Rf=0.25 ($CH_2Cl_2$/ethanol 85/15); Molecular formula=$C_{33}H_{40}BrFN_2O$; Melting point=>200° C.; Mass spectra: [M+1]=499.1 m/z RMN $^1$H (400 MHz, $CD_3OD$) δ (ppm): 1.07-1.44 (m, 12H, 12CH(cyclohexyl)), 1.61-1.95 (m, 10H, 10CH(cyclohexyl)), 3.10 (s, 3H, $CH_3$), 4.00 (d, 2H, J=6.2 Hz, O—$CH_2$), 4.52 (d, 2H, J=7.3 Hz, N—$CH_2$), 5.98 (s, 2H, N—$CH_2$), 7.07 (dd, 1H, $J_{6-8}$=2.1 Hz, $J_{6-5}$=8.9 Hz, H-6), 7.14-7.25 (m, 5H, 4ArH+H-8), 8.25 (d, 1H, $J_{5-6}$=8.7 Hz, H-5), 8.44 (d, 1H, $J_{4-3}$=6.4 Hz, H-4), 8.60 (d, 1H, $J_{3-4}$=6.6 Hz, H-3).

RMN $^{13}$C (100 MHz, $CD_3OD$) δ (ppm): 15.67 ($CH_3$), 25.50 (CH(cyclohexyl)), 25.66 (CH(cyclohexyl)), 25.81 (CH (cyclohexyl)), 26.27 (CH(cyclohexyl)), 29.58 (CH(cyclohexyl)), 30.29 (CH(cyclohexyl)), 37.73 (CH(cyclohexyl)), 40.28 (CH(cyclohexyl)), 51.02 (N—$CH_2$), 59.67 (N—$CH_2$), 73.95 (O—$CH_2$), 94.48 (C-8), 112.75 ($C_q$), 113.86 (C-6), 113.90 (C-4), 116.03 (d, J=22.0 Hz, 2C—ArH), 123.92 (C-5), 128.78 (d, J=7.7 Hz, 2C—ArH), 130.42 (d, J=2.9 Hz, $C_q$), 134.51 ($C_q$), 135.34 (C-3), 135.49 ($C_q$), 139.23 ($C_q$), 149.13 ($C_q$), 162.90 (d, J=247.3 Hz, $C_q$), 164.10 ($C_q$).

RMN $^{19}$F (376 MHz, $CD_3OD$) δ (ppm): −114.81 (s).

Synthesis of Compound CV53 (See Table 1): 1-methyl-2-hexyl-7-benzyloxy-9-benzyl-β-carbolin-2-ium bromide The title compound was synthesized from CV9 (0.200 g, 0.528 mmol) in presence of 1-bromohexane (0.872 g, 5,284 mmol) as described here above.

Yellow-brown powder; Yield=34%; Rf=0.81 ($CH_2Cl_2$/ethanol 85/15); Molecular formula=$C_{32}H_{35}BrN_2O$; Melting point=>150° C.; Mass spectra: [M+1]=463.3 m/z RMN $^1$H (400 MHz, $CD_3OD$) δ (ppm): 0.87-0.92 (m, 6H, N—$CH_2$—$CH_2$—$(CH_2)_3$—$CH_3$), 1.88-1.89 (m, 3H, N—$CH_2$—$CH_2$—$(CH_2)_3$—$CH_3$), 3.02 (s, 3H, $CH_3$), 4.62 (m, 2H, N—$CH_2$—$CH_2$), 5.19 (s, 2H, O—$CH_2$), 5.96 (s, 2H, N—$CH_2$), 7.03 (d, 2H, J=6.4 Hz, N—$CH_2$), 7.15-7.41 (m, 12H, H-8+H-6+10ArH), 8.30 (d, 1H, $J_{5-6}$=8.7 Hz, H-5), 8.40 (d, 1H, $J_{4-3}$=6.6 Hz, H-4), 8.49 (d, 1H, $J_{3-4}$=6.6 Hz, H-3).

RMN $^{13}$C (100 MHz, CD$_3$OD) δ (ppm): 12.94 (CH$_3$), 13.08 (CH$_3$), 22.21 (N—(CH$_2$)$_4$—CH$_2$), 25.72 (—N—(CH$_2$)$_3$—CH$_2$), 30.51 (N—(CH$_2$)$_2$—CH$_2$), 31.07 (N—CH$_2$—CH$_2$), 57.47 (N—CH$_2$), 67.62 (N—CH$_2$), 70.35 (O—CH$_2$), 94.32 (C-8), 114.17 (C-6), 124.14 (C-4), 125.26 (C-5), 127.48 (C—ArH), 127,70 (C—ArH), 127.84 (C—ArH), 128.27 (C—ArH), 128.52 ($C_q$), 129.08 ($C_q$), 131.05 ($C_q$), 133.86 ($C_q$), 134,89 ($C_q$), 135.92 ($C_q$), 136.36 ($C_q$), 136.98 (C-3), 148.38 ($C_q$), 163.58 ($C_q$).

Synthesis of Compound CV56 (See Table 1): 1-methyl-2-propyl-7-benzyloxy-9-benzyl-β-carbolin-2-ium bromide The title compound was synthesized from CV9 (0.400 g, 1.057 mmol) in presence of 1-bromopropane (1.300 g, 10.569 mmol) as described here above.

Yellow powder; Yield=7%; Rf=0.33 (CH$_2$Cl$_2$/ethanol 85/15); Molecular formula=C$_{29}$H$_{29}$BrN$_2$O; Melting point=>200° C.; Mass spectra: [M+1]=421.3 m/z RMN $^1$H (400 MHz, CD$_3$OD) δ (ppm): 0.98-1.07 (m, 3H, CH$_3$), 3.02 (s, 3H, CH$_3$), 4.58-4.61 (m, 2H, N—CH$_2$—CH$_2$), 5.19 (s, 2H, O—CH$_2$), 5.96 (s, 2H, N—CH$_2$), 7.04 (d, 2H, J=6.7 Hz, N—CH$_2$), 7.15-7.40 (m, 12H, H-8+H-6+10ArH), 8.30 (d, 1H, $J_{5-6}$=8.7 Hz, H-5), 8,40 (d, 1H, $J_{4-3}$=6.6 Hz, H-4), 8.49 (d, 1H, $J_{3-4}$=6.6 Hz, H-3).

RMN $^{13}$C (100 MHz, CD$_3$OD) δ (ppm): 9.58 (CH$_3$), 14.88 (CH$_3$), 23.84 (N—CH$_2$—CH$_2$—CH$_3$), 58.77 (N—CH$_2$), 67.76 (N—CH$_2$), 70.34 (O—CH$_2$), 94.36 (C-8), 113.26 ($C_q$), 114.12 (C-6), 124.17 (C-4), 125.27 (C-5), 127.48 (C—ArH), 127.69 (C—ArH), 127.84 (C—ArH), 128.27 (C—ArH), 129,08 (C—ArH), 133.83 ($C_q$), 134.96 ($C_q$), 135.89 ($C_q$), 136.37 ($C_q$), 136.98 ($C_q$), 138.88 (C-3), 148.38 ($C_q$), 163.54 ($C_q$).

Alternative General Procedure for N$_2$-alkylation of 1-methyl-O$_7$-substituted-N$_9$-substituted-7-hydroxy-β-carboline (Reaction c. of Scheme 1)

According to reaction c. of Scheme 1,1-methyl-O$_7$-substituted-N$_9$-substituted-7-hydroxy-β-carboline (200 mg) is dissolved in tetrahydrofurane (10 mL), ten equivalents of R$^1$-L$^1$-Br (in particular, 1-bromoethylbenzene, or 1-bromomethylalkane) are added, and the mixture is placed in the microwave reactor at 155° C. during 4 h. At the end of the process, a TLC (CH$_2$Cl$_2$/ethanol 85/15) is carried out. Then, the solvents are evaporated under reduced pressure to give the crude product which is purified by column chromatography as described in the general section with a mobile phase of dichloromethane/ethanol (from 100/0 to 85/15) as eluant.

Synthesis of Compound PL2 (See Table 1): 1-methyl-2-(3-methylbutyl)-7-benzyloxy-9-benzyl-β-carbolin-2-ium bromide The title compound was synthesized from CV9 (0.400 g, 1,061 mmol) in presence of 1-bromo-3-methylbutane (1.596 g, 10.567 mmol) as described here above.

White powder; Yield=17%; Rf=0.34 (CH$_2$Cl$_2$/ethanol 85/15); Molecular formula=C$_{31}$H$_{33}$BrN$_2$O; Melting point=>200° C.; Mass spectra: [M+1]=449.2 m/z RMN $^1$H (400 MHz, DMSO-d$_6$) δ (ppm): 0.91-0.92 (m, 6H, CH$_3$), 1.62-1.72 (m, 3H, CH$_2$—CH(CH$_3$)$_2$), 2.95 (s, 3H, CH$_3$), 4.59-4.63 (m, 2H, N—CH$_2$), 5.22 (s, 2H, O—CH$_2$), 6.00 (s, 2H, N—CH$_2$), 7.00-7.49 (m, 12H, H-8+H-6+10ArH), 8.41 (d, 1H, $J_{5-6}$=8.7 Hz, H-5), 8.59 (d, 1H, $J_{4-3}$=6.6 Hz, H-4), 8.67 (d, 1H, $J_{3-4}$=6.6 Hz, H-3).

RMN $^{13}$C (100 MHz, DMSO-d$_6$) δ (ppm): 16.12 (CH$_3$), 22.68 (CH$_3$), 26.01 (N—(CH$_2$)$_2$—CH), 48.86 (N—CH$_2$—CH$_2$—CH$_2$), 56.27 (N—CH$_2$—CH$_2$), 70.56 (N—CH$_2$), 70.64 (N—CH$_2$), 95.57 (C-8), 113.35 ($C_q$), 113.38 ($C_q$), 114.07 (C-6), 115.07 ($C_q$), 125.25 (C-4), 126.07 (C-5), 128.07 (C—ArH), 129.02 (C—ArH), 129.62 (C—ArH), 133.35 (C—ArH), 135.64 (C—ArH), 135.82 ($C_q$), 136.71 ($C_q$), 138.11 (C-3), 139.64 ($C_q$), 148.18 ($C_q$), 163.18 ($C_q$).

Synthesis of Compound PL4 (See Table 1): 1-methyl-2-phenethyl-7-benzyloxy-9-benzyl-β-carbolin-2-ium bromide The title compound was synthesized from CV9 (0.200 g, 0.541 mmol) in presence of 2-bromoethylbenzene (0.977 g, 5.280 mmol) as described here above.

White powder; Yield=32%; Rf=0.36 (CH$_2$Cl$_2$/ethanol 85/15); Molecular formula=C$_{34}$H$_{31}$BrN$_2$O; Melting point=>200° C.; Mass spectra: [M+1]=483,4 m/z RMN $^1$H (400 MHz, DMSO-d$_6$) δ (ppm): 2.91 (s, 3H, CH$_3$), 3.12 (t, 2H, J=7.2 Hz, N—CH$_2$—CH$_2$), 4.88 (t, 2H, J=7.2 Hz, N—CH$_2$—CH$_2$), 5.23 (s, 2H, N—CH$_2$), 6.01 (s, 2H, O—CH$_2$), 6.96-7.50 (m, 17H, H-8+H-6+15ArH), 8.39 (d, 1H, $J_{5-6}$=8.9 Hz, H-5), 8.50-8.53 (m, 2H, H-3+H-4).

RMN $^{13}$C (100 MHz, DMSO-d$_6$) δ (ppm): 16.11 (CH$_3$), 36.37 (N—CH$_2$—CH$_2$), 48.89 (N—CH$_2$), 58.28 (N—CH$_2$), 70.63 (O—CH$_2$), 95.60 (C-8), 113.32 ($C_q$), 114.13 (C-6), 114.78 (C-4), 125.31 (C-5), 126.01 (C—ArH), 128.65 (C—ArH), 129.01 (C—ArH), 129.51 (C—ArH), 129.63 (C—ArH), 133.39 ($C_q$), 135.55 ($C_q$), 135.95 ($C_q$), 136.76 (C-3), 136.85 ($C_q$), 138.06 ($C_q$), 139.85 ($C_q$), 148.23 ($C_q$), 163.19 ($C_q$).

General Procedure for O$_7$-dealkylation from 1-methyl-O$_7$-substituted-N$_9$-substituted-7-hydroxy-β-carboline (Reaction d. of Scheme 1)

According to reaction d. of Scheme 1,1-methyl-O$_7$-substituted-N$_9$-substituted-7-hydroxy-β-carboline (150 mg) is dissolved under stirring in methanol (10 mL). Palladium/charcoal 10% w/w (20 mg) is added, and the mixture is stirred at room temperature under hydrogen atmosphere for 48 h. The reaction is followed by TLC (CH$_2$Cl$_2$/ethanol 9/1). At the end of the reaction, the mixture is filtered, and the filtrate is evaporated under reduced pressure to give a crude residue which is purified by column chromatography as described in the general section with a mobile phase of dichloromethane/ethanol (95/5) as eluant.

Synthesis of Compound CV27 (See Table 1): 1-methyl-7-hydroxy-9-benzyl-β-carboline The title compound was synthesized from CV9 (0.150 g, 0.40 mmol) in presence of palladium/charcoal 10% w/w (20 mg) as described here above.

Yellow powder; Yield=89%; Rf=0.43 (CH$_2$Cl$_2$/ethanol 85/15); Molecular formula=C$_{19}$H$_{16}$N$_2$O; Melting point=234° C.; Mass spectra: [M+1]=289.0 m/z RMN $^1$H (400 MHz, CD$_3$OD) δ (ppm): 2.90 (s, 3H, CH$_3$), 5.81 (s, 2H, N—CH$_2$), 6.88 (d, 1H, $J_{8-6}$=1.8 Hz, H-8), 6.94 (dd, 1H, $J_{6-5}$=8.7 Hz, $J_{6-8}$=1.8 Hz, H-6), 6.98 (d, 2H, J=6.6 Hz, 2Ar—H), 7.23-7.32 (m, 3H, 3Ar—H), 8.17 (d, 1H, $J_{5-6}$=8.7 Hz, H-5), 8.18 (d, 1H, $J_{3-4}$=6.0 Hz, H-3), 8.25 (d, 1H, $J_{4-3}$=6.0 Hz, H-4).

RMN $^{13}$C (100 MHz, CD$_3$OD) δ (ppm): 17.25 (CH$_3$), 47.91 (N—CH$_2$), 94.93 (C-8), 112.90 (C$_q$), 112.99 (C-6), 113.45 (C-4), 124.01 (C-5), 125.12 (2C—ArH), 127.58 (C—ArH), 128.95 (2C—ArH), 130.34 (C-3), 134.12 (C$_q$), 134.34 (C$_q$), 136.91 (C$_q$), 137.33 (C$_q$), 147.31 (C$_q$), 162.26 (C$_q$).

General Procedure for O$_7$-alkylation from 1-methyl-7-hydroxy-β-carboline (Reaction e. of Scheme 1)

According to reaction e. of Scheme 1, O$_7$-alkylation from 1-methyl-7-hydroxy-β-carboline (500 mg), in presence of cesium carbonate (1,410 g) is dissolved in DMF (10 ml), and the mixture is stirred under argon atmosphere. Then, one and half equivalent of R$^3$-L$^3$-Br is added, and the mixture is stirred at room temperature for 5 h. At the end of the reaction, the mixture is diluted with dichloromethane (40 mL). The organic layer is washed once with water (10 ml) and three times with brine (10 mL), dried with MgSO$_4$ which is collected by filtration. The organic layer was finally evaporated under reduced pressure to give the crude product which is purified by column chromatography as described in the general section with a mobile phase of dichloromethane/ethanol (95/5) as eluant.

Synthesis of Compound JR79 (See Table 1): 1-methyl-7-benzyloxy-β-carboline

The title compound was synthesized from 1-methyl-7-hydroxy-β-carboline (0.500 g, 1.59 mmol) in presence of cesium carbonate (1.410 g, 4.33 mmol) and 1-bromomethylbenzene (0.432 g, 2.53 mmol) as described here above.

White powder; Yield=70%; Rf=0.69 (CH$_2$Cl$_2$/ethanol 80/20); Molecular formula=C$_{19}$H$_{16}$N$_2$O; Melting point=212.3° C.; Mass spectra: [M+1]=289.1 m/z RMN $^1$H (400 MHz, CDCl$_3$) δ (ppm): 2.78 (s, 3H, CH$_3$), 5.17 (s, 2H, O—CH$_2$), 6.98 (dd, 1H, J$_{6-5}$=8.7 Hz, J$_{6-8}$=2.3 Hz, H-6), 7.01 (d, 1H, J$_{8-6}$=2.1 Hz, H-8), 7.32-7.47 (m, 5H, 5Ar—H), 7.71 (d, 1H, J$_{4-3}$=5.5 Hz, H-4), 7.97 (d, 1H, J$_{5-6}$=8.5 Hz, H-5), 8.28 (s, 1H, N—H), 8.32 (d, 1H, J$_{3-4}$=5.3 Hz, H-4).

RMN $^{13}$C (100 MHz, CDCl$_3$) δ (ppm): 20.31 (CH$_3$), 70.50 (O—CH$_2$), 96.11 (C-8), 110.39 (C-6), 112.34 (C-4), 116.16 (C$_q$), 122.82 (C-5), 127.56 (C—ArH), 128.18 (C—ArH), 128.64 (C$_q$), 128.77 (C—ArH), 134.74 (C$_q$), 136.84 (C$_q$), 139.06 (C-3), 141.12 (C$_q$), 141.60 (C$_q$), 159.96 (C$_q$).

General Procedure for N$_9$-alkylation from 1-methyl-O$_7$-substituted-7-hydroxy-β-carboline (Reaction f. of Scheme 1)

According to reaction f. of Scheme 1, N$_9$-alkylation from 1-methyl-O$_7$-substituted-7-hydroxy-β-carboline (100 mg), in presence of one equivalent of R$^2$-L$^2$-I (in particular 1-iodopropane) and five equivalents of NaH are dissolved in DMF (15 mL). The mixture is stirred at room temperature for 24 h under argon atmosphere. At the end of the reaction, the mixture is diluted with dichloromethane (40 mL). The organic layer is washed once with water (10 mL) and three times with brine (10 mL), dried with MgSO$_4$ which is collected by filtration. The organic layer was finally evaporated under reduce pressure to give the crude product which is purified by column chromatography as described in the general section with a mobile phase of dichloromethane/ethanol (95/5) as eluant.

Synthesis of Compound CV33 (See Table 1): 1-methyl-7-benzyloxy-9-propyl-β-carboline The title compound was synthesized from JR79 (1.280 g, 4.45 mmol) in presence of 1-iodopropane (0.920 g, 5.43 mmol) and NaH (0.530 g, 22.2 mmol) as described here above.

Brown powder; Yield=52%; Rf=0.53 (CH$_2$Cl$_2$/ethanol 90/10); Molecular formula=C$_{22}$H$_{22}$N$_2$O; Melting point=113° C.; Mass spectra: [M+1]=331.2 m/z RMN $^1$H (400 MHz, CDCl$_3$) δ (ppm): 0.98 (t, 3H, J=7.5 Hz, CH$_2$—CH$_2$—CH$_3$), 1.77-1.87 (m, 2H, CH$_2$—CH$_2$—CH$_3$), 3.00 (s, 3H, CH$_3$), 4.38 (t, 2H, J=7.8 Hz, CH$_2$—CH$_2$—CH$_3$), 5.20 (s, 2H, O—CH$_2$), 6.93 (d, 1H, J$_{8-6}$=1.8 Hz, H-8), 6.96 (dd, 1H, J$_{6-5}$=8.5 Hz, J$_{6-8}$=2.1 Hz, H-6), 7.33-7.51 (m, 5H, ArH), 7.72 (d, 1H, J$_{4-3}$=5.3 Hz, H-4), 7.97 (d, 1H, J$_{5-6}$=8.5 Hz, H-5), 8.28 (d, 1H, J$_{3-4}$=5.3 Hz, H-3)

RMN $^{13}$C (100 MHz, CDCl$_3$) δ (ppm): 11.35 (CH$_3$), 23.47 (CH$_3$), 23.96 (CH$_2$—CH$_2$—CH$_3$), 46.47 (CH$_2$—CH$_2$—CH$_3$), 70.67 (O—CH$_2$), 94.99 (C-8), 109.27 (C-6), 112.38 (C-4), 115.48 (C$_q$), 122.46 (C-5), 127.69 (s, C—ArH), 128.21 (s, C—ArH), 128.78 (s, C—ArH), 129.36 (C$_q$), 135.48 (C$_q$), 136.92 (C$_q$), 138.27 (C-3), 140.66 (C$_q$), 143.11 (C$_q$), 159.98 (C$_q$).

General Procedure for N$_2$-alkylation of 1-methyl-O$_7$-substituted-N$_9$-substituted-7-hydroxy-β-carboline (Reaction h. of Scheme 1)

According to reaction h. of Scheme 1, 1-methyl-O$_7$-substituted-N$_9$-substituted-7-hydroxy-β-carboline (100 mg) is dissolved in tetrahydrofurane (15 mL), ten equivalents of R$^1$-L$^1$-Br (in particular, 1-bromomethylbenzene, substituted or not) are added, and the mixture is refluxed for 48 h under argon atmosphere. The reaction is followed by TLC (CH$_2$Cl$_2$/ethanol 85/15). At the end of the reaction, the solvents are evaporated under reduced pressure to give the crude product which is purified by column chromatography as described in the general section with a mobile phase of dichloromethane/ethanol (95/5) as eluant.

Synthesis of Compound CV34 (See Table 1): 1-methyl-2-benzyl-7-benzyloxy-9-propyl-β-carbolin-2-ium bromide The title compound was synthesized from CV33 (0.150 g, 0.454 mmol) in presence of 1-bromomethyl-benzene (0.773 g, 4.540 mmol) as described here above.

Brown powder; Yield=69%; Rf=0.22 (CH$_2$Cl$_2$/ethanol 90/10); Molecular formula=C$_{29}$H$_{29}$BrN$_2$O; Melting point=>200° C.; Mass spectra: [M+1]=421.3 m/z RMN $^1$H (400 MHz, CD$_3$OD) δ (ppm): 0.94 (t, 3H, J=7.5 Hz, CH$_2$—CH$_2$—CH$_3$), 1.78-1.87 (m, 2H, CH$_2$—CH$_2$—CH$_3$), 3.12 (s, 3H, CH$_3$), 4.58 (t, 2H, J=7,8 Hz, CH$_2$—CH$_2$—CH$_3$), 5.32 (s, 2H, O—CH$_2$), 5.99 (s, 2H, N—CH$_2$), 7.13-7.51 (m, 12H, 10ArH+H-6+H-8), 8.27 (d, 1H, J$_{5-6}$=8,9 Hz, H-5), 8.43 (d, 1H, J$_{4-3}$=6.4 Hz, H-4), 8.60 (d, 1H, J$_{3-4}$=6.4 Hz, H-3).

RMN $^{13}$C (100 MHz, CD$_3$OD) δ (ppm): 9.86 (CH$_2$—CH$_2$—CH$_3$), 15.49 (CH$_3$), 23.51 (CH$_2$—CH$_2$—CH$_3$), 46.85 (CH$_2$—CH$_2$—CH$_3$), 60.44 (N—CH$_2$), 70.43 (O—CH$_2$), 94.57 (C-8), 113.19 (C$_q$), 114.03 (C-6+C-4), 124.12 (C-5), 126.44 (2C—ArH), 127.45 (2C—ArH), 127.89 (C—ArH), 128.35 (2C—ArH), 128.58 (C—ArH), 129.26 (2C—ArH), 134.18 (C$_q$), 134.34 (C$_q$), 135.33 (C-3), 135,38 (C$_q$), 136.60 (C$_q$), 139.18 (C$_q$), 148.13 (C$_q$), 163.50 (C$_q$).

Synthesis of Compound CV35 (See Table 1): 1-methyl-2-(2-fluorobenzyl)-7-benzyloxy-9-propyl-β-carbolin-2-ium bromide The title compound was synthesized from CV33 (0.150 g, 0.454 mmol) in presence of 1-bromomethyl-2-fluorobenzene (0.858 g, 4.540 mmol) as described here above.

Yellow powder; Yield=61%; Rf=0.60 ($CH_2Cl_2$/ethanol 85/15); Molecular formula=$C_{29}H_{28}BrFN_2O$; Melting point=>200° C.; Mass spectra: [M+1]=439.3 m/z RMN $^1H$ (400 MHz, $CD_3OD$) δ (ppm): 0.95 (t, 3H, J=7.3 Hz, $CH_2$—$CH_2$—$CH_3$), 1.80-1.89 (m, 2H, $CH_2$—$CH_2$—$CH_3$), 3.16 (s, 3H, $CH_3$), 4.60 (t, 2H, J=7.8 Hz, $CH_2$—$CH_2$—$CH_3$), 5.32 (s, 2H, O—$CH_2$), 6.04 (s, 2H, N—$CH_2$), 7.05-7.51 (m, 11H, 9ArH+H-6+H-8), 8.26 (d, 1H, $J_{5-6}$=8.9 Hz, H-5), 8.41 (d, 1H, $J_{4-3}$=6,6 Hz, H-4), 8.58 (d, 1H, $J_{3-4}$=6.4 Hz, H-3).

RMN $^{13}C$ (100 MHz, $CD_3OD$) δ (ppm): 9.87 ($CH_2$—$CH_2$—$CH_3$), 15.57 ($CH_3$), 23.50 ($CH_2$—$CH_2$—$CH_3$), 46.88 ($CH_2$—$CH_2$—$CH_3$), 54.88 (d, J=3.8 Hz, N—$CH_2$), 70.44 (O—$CH_2$), 94.56 (C-8), 113.17 ($C_q$), 114.02 (C-4), 114.08 (C-6), 115.82 (d, J=21.1 Hz, C—ArH), 121.44 (d, J=13.4 Hz, $C_q$), 124.16 (C-5), 125.17 (d, J=2.9 Hz, C—ArH), 127.45 (2C—ArH), 127.90 (C—ArH), 128.35 (2C—ArH), 128.73 (d, J=2.9 Hz, C—ArH), 131.14 (d, J=8.6 Hz, C—ArH), 134.22 ($C_q$), 135.25 (C-3), 135.30 ($C_q$), 136.58 ($C_q$), 139.21 ($C_q$), 148.22 ($C_q$), 160.36 (d, J=247.3 Hz, $C_q$), 163.56 ($C_q$).

RMN $^{19}F$ (376 MHz, $CD_3OD$) δ (ppm): −118.45 (s).

Synthesis of Compound CV36 (See Table 1): 1-methyl-2-(4-fluorobenzyl)-7-benzyloxy-9-propyl-β-carbolin-2-ium bromide The title compound was synthesized from CV33 (0.150 g, 0.454 mmol) in presence of 1-bromomethyl-4-fluorobenzene (0.858 g, 4.540 mmol) as described here above.

Brown powder; Yield=39%; Rf=0.56 ($CH_2Cl_2$/ethanol 85/15); Molecular formula=$C_{29}H_{28}BrFN_2O$; Melting point=>200° C.; Mass spectra: [M+1]=439.3 m/z RMN $^1H$ (400 MHz, $CD_3OD$) δ (ppm): 0.95 (t, 3H, J=7.3 Hz, $CH_2$—$CH_2$—$CH_3$), 1.79-1.89 (m, 2H, $CH_2$—$CH_2$—$CH_3$), 3.13 (s, 3H, $CH_3$), 4.59 (t, 2H, J=7.8 Hz, $CH_2$—$CH_2$—$CH_3$), 5.32 (s, 2H, O—$CH_2$), 5.97 (s, 2H, N—$CH_2$), 7.13-7.52 (m, 11H, 9ArH+H-6+H-8), 8.27 (d, 1H, $J_{5-6}$=8.9 Hz, H-5), 8.43 (d, 1H, $J_{4-3}$=6.4 Hz, H-4), 8.59 (d, 1H, $J_{3-4}$=6.6 Hz, H-3).

RMN $^{13}C$ (100 MHz, $CD_3OD$) δ (ppm): 9.86 ($CH_2$—$CH_2$—$CH_3$), 15.49 ($CH_3$), 23.49 ($CH_2$—$CH_2$—$CH_3$), 46.92 ($CH_2$—$CH_2$—$CH_3$), 59.70 (N—$CH_2$), 70.46 (O—$CH_2$), 94.61 (C-8), 113.20 ($C_q$), 114.06 (C-6), 114.09 (C-4), 116.04 (d, J=22.0 Hz, C—ArH), 124.13 (C-5), 127.44 (C—ArH), 127,89 (C—ArH), 128.35 (C—ArH), 128.82 (d, J=8.6 Hz, C—ArH), 130.33 (d, J=2.9 Hz, $C_q$), 134.23 ($C_q$), 135.17 (C-3), 135.44 ($C_q$), 136.60 ($C_q$), 139.15 ($C_q$), 148.18 ($C_q$), 162.91 (d, J=248.2 Hz, $C_q$), 163.56 ($C_q$).

RMN $^{19}F$ (376 MHz, $CD_3OD$) δ (ppm): −114.81 (s).

Other compounds based on general formulas (Ia) or (Ib) can be made through similar synthesis routes such as the ones exemplified above and in Table 1.

Example 2

In Vitro Characterization of the Biological Effects of the Compounds According to the Invention A/ Effect on Overall Cell Growth MTT tests were performed in order to rapidly, i.e., within 5 days, measure the effect of the present compounds on the overall cell growth. The test measured the number of metabolically active living cells that were able to transform the yellow product 3-(4,5-dimethylthiazol-2-yl)-2,5-diphenyl tetrazolium bromide (herein referred as MTT) into the blue product formazan dye by mitochondrial reduction. The amount of formazan obtained at the end of the experiment, measured by means of a spectrophotometer, is directly proportional to the number of living cells. Optical density determination thus enabled a quantitative measurement of the effect of the investigated compounds as compared to the control condition (untreated cells) and/or to other reference compounds.

Five human cancer cell lines set forth in Table 3 were used in the MTT tests. These cancer cell lines cover two histological cancer types including glioma (Hs683, T98G, U373), and oesophageal (OE21, OE33) cancers. The U373 cell line is apoptosis-resistant but autophagy-sensitive.

To perform the assay, cells were allowed to grow in 96-well micro-wells with a flat bottom with an amount of 100 μl of cell suspension per well with 5,000 to 8,000 cells/well depending on the cell type used. Each cell line was seeded in its appropriate culture medium.

The detailed experimental procedure was as follows: after a 24-hour period of incubation at 37° C., the culture medium was replaced by 100 μl of fresh medium in which the tested compound was previously dissolved, at the following molar concentrations: $1\times10^{-8}$ M, $5\times10^{-8}$ M, $1\times10^{-7}$ M, $5\times10^{-7}$ M, $1\times10^{-6}$ M, $5\times10^{-6}$ M, $1\times10^{-5}$ M, $5\times10^{-5}$ M and $1\times10^{-4}$ M. Each experiment was performed in sestuplicate (6 times).

After 72 hours of incubation at 37° C. with (experimental conditions) or without (control condition) the compound to be tested, the medium was replaced by 100 μl MTT dissolved in RPMI (1640 without phenol red) at a concentration of 0.5 or 1 mg/ml. The micro-wells were subsequently incubated during 3 hours and a half at 37° C. and centrifuged at 1300 rpm during 10 minutes. MTT was removed and formazan crystals formed were dissolved in 100 ml DMSO. The micro-wells were shaken for 5 minutes and read on a spectrophotometer at wavelengths of 570 nm (maximal formazan absorbance).

For each experimental condition, the mean optical density was calculated, allowing the determination of the percentage of remaining living cells in comparison to the control.

Table 3 shows the IC50 (representing the range of concentration of the compound tested that resulted in a 50% inhibition of overall tumour cells growth) for each compound in each cell line investigated.

The origin of all the cell lines we used, along with their biological characteristics, and the validation procedures of the MTT colorimetric assay as employed here are fully detailed in Van Quaquebeke et al., 2005, J Med Chem 48:849-856; Ingrassia et al., 2009, J Med Chem 52:1100-1114; Mathieu et al., 2009, J Cell Mol Med, Feb. 20, 2009.

TABLE 3

IC$_{50}$ (µM) values. IC50: Concentration of drug needed in order to inhibit cell population growth by 50% (MTT test)

| Compound | Antiproliferative class[a] (GGR[b]) | U373 | T98G | Hs683 | OE21 | OE33 | Mean ± SEM |
|---|---|---|---|---|---|---|---|
| harmine | I (0.3) | 32 ± 2 | 24 ± 2 | 37 ± 1 | 32 ± 2 | 18 ± 1 | 28 ± 3 |
| CV9/JR84 | II (0.3) | 18 ± 2 | 36 ± 2 | 33 ± 1 | 28 ± 3 | 40 ± 4 | 31 ± 4 |
| CV5 | I (0.9) | 0.40 ± 0.06 | 27 ± 1 | 17.5 ± 0.9 | 7.9 ± 0.2 | 16 ± 2 | 14 ± 5 |
| CV11 | III (0.2) | 30 ± 1 | 14 ± 2 | 17 ± 2 | 15 ± 2 | 25 ± 2 | 20 ± 3 |
| CV12 | II (0.2) | 30.7 ± 0.8 | 32 ± 1 | 30 ± 2 | 17 ± 2 | 15 ± 3 | 25 ± 4 |
| CV21/JR95 | I (0.4) | 0.44 ± 0.01 | 0.48 ± 0.02 | 0.49 ± 0.05 | 1.3 ± 0.2 | 0.7 ± 0.1 | 0.7 ± 0.2 |
| CV18 | I (0.3) | 0.5 ± 0.2 | 0.37 ± 0.01 | 0.44 ± 0.04 | 0.38 ± 0.02 | 0.70 ± 0.08 | 0.48 ± 0.06 |
| CV17 | I (0.4) | 0.59 ± 0.06 | 0.56 ± 0.05 | 1.6 ± 0.3 | 0.61 ± 0.04 | 2.4 ± 0.3 | 1.2 ± 0.4 |
| CV23 | I (0.3) | 0.43 ± 0.07 | 0.40 ± 0.04 | 0.9 ± 0.1 | 0.50 ± 0.09 | 1.4 ± 0.1 | 0.8 ± 0.2 |
| CV25 | I (0.4) | 0.46 ± 0.08 | 0.43 ± 0.02 | 1.2 ± 0.4 | 1.6 ± 0.3 | 1.6 ± 0.2 | 1.1 ± 0.3 |
| CV16 | I (0.4) | 0.82 ± 0.08 | 0.97 ± 0.02 | 2.8 ± 0.4 | 0.4 ± 0.1 | 2.9 ± 0.1 | 1.6 ± 0.5 |
| CV19 | I (0.2) | 0.6 ± 0.2 | 0.7 ± 0.2 | 2.2 ± 0.2 | 1.4 ± 0.3 | 3.0 ± 0.2 | 1.6 ± 0.4 |
| CV22 | I (0.5) | 0.9 ± 0.1 | 1.9 ± 0.3 | 4.5 ± 0.4 | 2.9 ± 0.1 | 3.4 ± 0.1 | 2.7 ± 0.6 |
| CV24 | I (0.3) | 0.37 ± 0.02 | 0.16 ± 0.03 | 0.38 ± 0.009 | 0.42 ± 0.008 | 0.37 ± 0.01 | 0.34 ± 0.05 |
| CV26 | I (0.2) | 1.42 ± 0.08 | 0.070 ± 0.008 | 0.25 ± 0.02 | 0.35 ± 0.01 | 0.35 ± 0.02 | 0.5 ± 0.2 |
| CV29 | IV (0.1) | 2.9 ± 0.1 | 14 ± 2 | 13 ± 1 | 3.7 ± 0.2 | 3.1 ± 0.3 | 7 ± 3 |
| CV30 | I (0.8) | 0.04 ± 0.01 | 2.0 ± 0.6 | 3.1 ± 0.3 | 1.4 ± 0.2 | 1.0 ± 0.1 | 1.6 ± 0.4 |
| CV34 | III (0.3) | 0.41 ± 0.03 | 1.7 ± 0.5 | 2.6 ± 0.2 | 0.57 ± 0.08 | 0.3 ± 0.05 | 1.1 ± 0.4 |
| CV35 | I (0.4) | 0.39 ± 0.01 | 1.8 ± 0.3 | 0.45 ± 0.02 | 0.42 ± 0.02 | 0.25 ± 0.02 | 0.7 ± 0.3 |
| CV36 | IV (0.1) | 0.88 ± 0.06 | 5.7 ± 0.2 | 3.1 ± 0.6 | 1.9 ± 0.3 | 1.0 ± 0.1 | 2.5 ± 0.9 |
| CV27 | II (0.2) | 80 ± 2 | 81 ± 11 | 79 ± 4 | 35 ± 2 | 35 ± 2 | 62 ± 11 |
| CV33 | III (0.3) | 26 ± 1 | 34 ± 1 | 13 ± 1 | 23 ± 2 | 9 ± 1 | 21 ± 4 |
| CV53 | | 0.66 ± 0.09 | 3.1 ± 0.5 | 0.6 ± 0.1 | 1.9 ± 0.3 | ND | 1.5 ± 0.6 |
| CV56 | | 2.5 ± 0.3 | 11 ± 1 | 0.6 ± 0.1 | 3.4 ± 0.8 | ND | 5 ± 2 |
| PL2 | | 0.39 ± 0.01 | 1.2 ± 0.2 | 0.37 ± 0.03 | 0.50 ± 0.09 | ND | 0.6 ± 0.2 |
| PL4 | | 2.0 ± 0.3 | 2.4 ± 0.4 | 2.31 ± 0.09 | 2.4 ± 0.3 | ND | 2.3 ± 0.1 |
| JR222 | II (0.4) | 2.5 ± 0.2 | 3.6 ± 0.2 | 8.1 ± 0.2 | 5.0 ± 0.4 | 6.3 ± 0.1 | 5 ± 1 |
| JR79 | III (0.2) | 9.3 ± 0.2 | 17 ± 3 | 17 ± 2 | 21 ± 1 | 4.1 ± 0.6 | 14 ± 3 |
| JR84 | II (0.3) | 18 ± 2 | 36 ± 2 | 33 ± 1 | 28 ± 3 | 40 ± 4 | 31 ± 4 |
| JR212 | I (0.3) | 24 ± 1 | 29 ± 2 | 30 ± 3 | 28 ± 2 | 31 ± 2 | 29 ± 1 |
| JR220 | I (0.2) | 64 ± 4 | 61 ± 7 | 53 ± 6 | 53 ± 4 | 66 ± 3 | 60 ± 3 |
| JR110 | IV (0.2) | >100 | 86 ± 11 | >100 | >100 | >100 | >97 |
| CV52 | | 22 ± 2 | 19 ± 2 | 26 ± 3 | 17 ± 2 | ND | 21 ± 2 |
| PL1 | | 9 ± 2 | 61 ± 6 | 31 ± 3 | 25 ± 4 | ND | 32 ± 11 |
| JR88 | II (0.2) | 3.9 ± 0.2 | 5.6 ± 0.2 | 3.6 ± 0.1 | 6.0 ± 0.6 | 5.5 ± 0.3 | 5 ± 1 |
| JR167 | IV (0.1) | 7.48 ± 0.07 | 7.2 ± 0.2 | 22 ± 2 | 8.3 ± 0.2 | 8.1 ± 0.2 | 11 ± 3 |
| JR155 | IV (0.2) | 9.1 ± 0.6 | 21 ± 1 | 21 ± 3 | 14 ± 1 | 7.9 ± 0.3 | 15 ± 3 |
| JR147 | IV (0.2) | 7.4 ± 0.4 | 12 ± 2 | 19 ± 2 | 33 ± 8 | 8.2 ± 0.4 | 16 ± 5 |
| JR169 | I (0.4) | 21.3 ± 0.8 | 20 ± 2 | 20 ± 1 | 16 ± 3 | 23 ± 3 | 20 ± 1 |
| JR221 | IV (0.1) | 24 ± 1 | 22 ± 3 | 23 ± 1 | 12 ± 3 | 25 ± 1 | 22 ± 3 |
| JR211 | II (0.2) | 32 ± 2 | 32.0 ± 0.7 | 28 ± 1 | 27 ± 2 | 29.8 ± 0.7 | 30 ± 1 |
| JR140 | III (0.2) | 27 ± 2 | 42 ± 3 | 53 ± 3 | 30 ± 4 | 31 ± 4 | 37 ± 5 |
| JR226 | I (0.3) | 42 ± 2 | 53 ± 3 | 41 ± 3 | 30 ± 4 | 63 ± 4 | 46 ± 6 |
| PL11 | | 2.5 ± 0.3 | 2.9 ± 0.4 | 4.0 ± 0.3 | 7.6 ± 0.3 | ND | 4.0 ± 1 |
| PL12 | | 0.22 ± 0.03 | 0.41 ± 0.01 | 0.26 ± 0.01 | 0.48 ± 0.04 | ND | 0.34 ± 0.06 |
| PL13 | | 3.4 ± 0.1 | 3.5 ± 0.1 | 3.1 ± 0.1 | 3.7 ± 0.1 | ND | 3.4 ± 0.1 |

[a]The antiproliferative class is determined by cellular imaging of cultured U373 cells over three consecutive days: class I: actually cytostatic for 3 days (<10% of cell death at the 3$^{rd}$ day). class II: cyctostatic but becomes cytotoxic with <10% cell death on the 2$^{nd}$ day, and >20% of cell death on the 3$^{rd}$ day. class III: cytostatic but rapidly becomes cytotoxic with <10% cell death on the 1$^{st}$ day, >20% of cell death on the 2$^{nd}$ day and >50% of cell death on the 3$^{rd}$ day. class IV: cytotoxic (>50% of cell death on the first day)
[b]The global growth (GG) is deduced by dividing the number of cells on the last image by the number of cells on the first image. The global growth ratio (GGR) is the ratio GG treated cells/GG control cells (without addition of drug), was further calculated thereby obtaining a value that describes the effect of compounds on the overall cell growth. The global grow ratio (GGR) is calculated 72 h after drug addition. The drug is used at a concentration corresponding to its IC50 (MTT-test determined).

B/ Impairment of Cell Proliferation and Cell Migration Triggered by the Compounds Described Herein in Various Cell Lines The effects of the di- and tri-substituted beta-carboline derivatives as described herein can also be determined on cell proliferation, migration and morphology by means of a cellular imaging approach (Debeir et al., Cytometry 60:29-40, 2004; Debeir et al., IEEE Trans Med Imaging 24:697-711, 2005) either in, e.g., the human U373-MG glioma cell line, which is apoptosis-resistant but autophagy-sensitive (Lefranc F et al., Neurosurgery 2008) or in, e.g., the human A549 non-small-cell-lung cancer cell line, which is apoptosis-resistant and autophagy-resistant (Mijatovic T et al., Neoplasia 2006, May; 8(5):402-12).

Investigations can also be performed in human normal fibroblasts (e.g., WS1 and W138). Cellular imaging relies on the use of computer-assisted phase-contrast microscopy making it possible to film the behaviour of living cells in culture dishes for several days.

Cells are seeded in a 25-cm$^2$ flask at a low density, treated or not with the compounds described herein (at a concentration of about 50 µM) and filmed thereafter for a period of 72 h. The experiments are conducted in quadruplicates.

The behaviour of the cells, in terms of morphology, growth and death are thus investigated. The effect on the overall growth is measured by counting the number of cells on the first (0 h) and the last image (72 h) of each film. The global growth ratio (GGR) is then deduced by dividing the number of cells on the last image by the number of cells on the first image. The ratio $GGR_{treated\ cells}/GGR_{control\ cells}$ is further calculated thereby providing a value that describes the effect of compounds of the present invention on the overall cell growth.

The methodology is fully described and validated in Debeir et al., 2008, Exp Cell Res 314:2985-2998 and Mathieu et al., 2009, J Cell Mol Med, Feb. 20, 2009.

Example 3

Dyrk1A Kinase Inhibition Profile of JR212, JR220, JR84, CV12, CV24, JR95

The IC50 profile of JR212, JR220, JR84, CV12, CV24, and JR95 was determined on DYRK1A protein kinase. IC50 values were measured by testing 10 concentrations of the compounds in the range from about $1 \times 10^{-4}$ M to about $3 \times 10^{-8}$ M in triplicate. Compound cv12 was tested in the range from about $5 \times 10^{-5}$ M to about $1.5 \times 10^{-9}$ M in triplicate.

A radiometric protein kinase assay (33PanQinase® Activity Assay) was used for measuring the kinase activity of DYRK1A protein kinase. All kinase assays were performed in 96-well FlashPlates™ from Perkin Elmer (Boston, Mass., USA) in a 50 µl reaction volume. The reaction cocktail was pipetted in four steps in the following order: 20 µl of assay buffer (standard buffer); 5 µl of [γ-33P]-ATP solution (in H2O); 5 µl of test compound (in 10% DMSO); 10 µl of substrate/10 µl of enzyme solution (premixed).

The assay contained 60 mM HEPES-NaOH, pH 7.5, 3 mM $MgCl_2$, 3 mM $MnCl_2$, 3 µM Na-orthovanadate, 1.2 mM DTT, 50 µg/ml PEG20000, 1 µM [γ-$^{33}$P]-ATP (approx. $3 \times 10^5$ cpm per well), protein kinase, and substrate.

For the determination of inhibitory profiles, DYRK1A protein kinase was used, which was purchased from Invitrogen Corporation. The kinase was expressed in 519 insect cells as human recombinant GST-fusion protein by means of the baculovirus expression system. According to the data sheet, the purity of the kinase was checked by SDS-PAGE/Coomassie staining and the identity of the kinase was verified by mass spectroscopy. About 5 ng/50 µl (about 0.9 nM) of dyrk1A kinase and about 2000 ng/50 µl of substrate (RBER-CHKtide) are used in each assay.

The reaction cocktails were incubated at 30° C. for 60 minutes. The reaction was stopped with 50 µl of 2% (v/v) $H_3PO_4$, plates were aspirated and washed two times with 200 µl 0.9% (w/v) NaCl. Incorporation of $^{33}$P was determined with a microplate scintillation counter (Microbeta, Wallac).

All assays were performed with a BeckmanCoulter/SAGIAN™ Core System.

For each plate, the median value of the cpm of the wells with complete reaction cocktails, but without kinase or compound to be tested, was defined as "low control" (n=8). This value reflects unspecific binding of radioactivity to the plate in the absence of protein kinase but in the presence of the substrate. Additionally, for each plate the median value of the cpm of the wells with the complete reaction cocktail, but without any compound, was taken as the "high control", i.e., full activity in the absence of any inhibitor (n=8). The difference between high and low control of was taken as 100% activity for each kinase. As part of the data evaluation the "low control" value from a particular plate was subtracted from the "high control" value as well as from all 80 "compound values" of the corresponding plate. The residual activity (in %) for each compound well was calculated by using the following formula: Res. Activity (%)=100×[(cpm of compound−low control)/(high control−low control)].

Figure 1B:
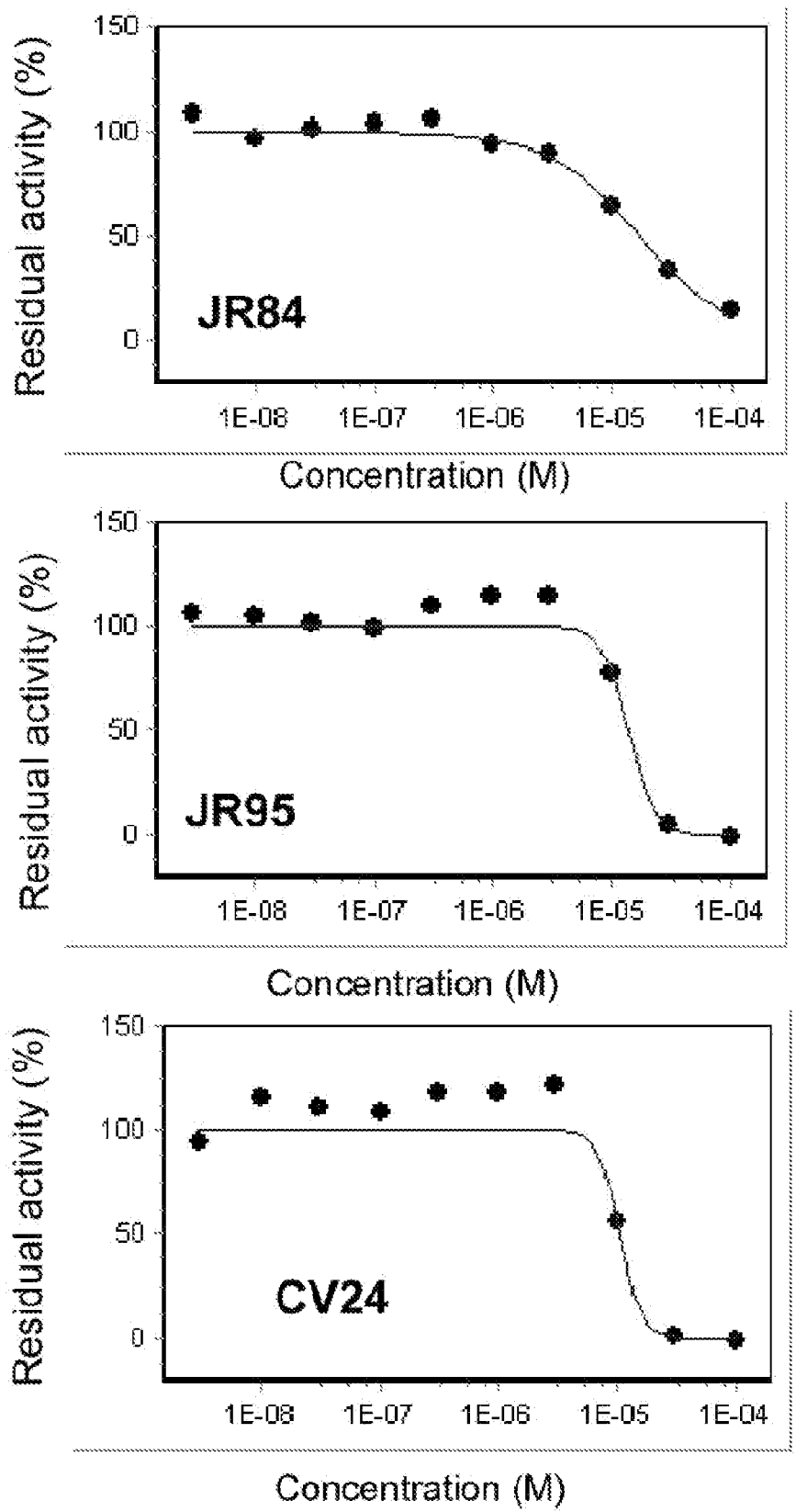
Figure 1C:
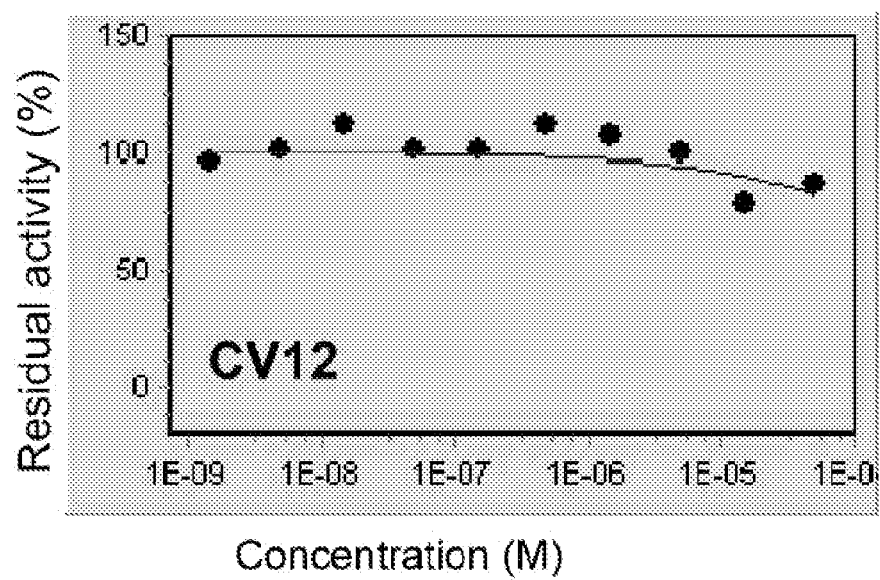

The dyrk1A kinase activity was tested in presence of JR212, JR220, JR84, CV12, CV24, JR95 at 10 concentrations to establish the kinase inhibition profile of the compounds. FIG. 1 A-C and Table 4 show that there is no correlation between the affinity of the compounds of the invention with DYRK1A and their anti-proliferative properties. Indeed, although several compounds exhibited similar IC50 towards DYRK1A, they however belonged to different anti proliferative class (GGR).

TABLE 4

| Compounds | $IC_{50}$: Concentration of drug (µM) needed in order to inhibit dyrk1A kinase activity by 50% | IC50 µM growth inhibition (MTT test) (anti-proliferative class-GGR) |
|---|---|---|
| JR212 | 10 | 29 (I) |
| JR220 | 15.5 | 60 (I) |
| JR84 | 16.3 | 31 (II) |
| CV12 | >10 | 25 (n.d)* |
| CV24 | 43 | 0.34 (n.d)* |
| JR95 | 21.2 | 0.7 (I) |

*n.d = not determined

Example 4

Analysis of the Cytostatic Vs Cytotoxic Effects of the Compounds Described Herein Quantitative videomicroscopy (Debeir O, et al. *IEEE Trans Med Imaging* 2005, 24, 697-711; Debeir O, et al. *Exp Cell Res* 2008, 314, 2985-2998) can be used to determine the cytostatic vs cytotoxic effects of the compounds of the invention. Each compound is tested on several cell lines (e.g., glioblastoma, melanoma) at the $IC_{50}$ concentration determined by the MTT test (see, above, example 2). For in vivo experiments, intravenous administration of cytotoxic compounds and oral administration for cytostatic compounds are preferred.

Example 5

FACS Cycle Measurement

The effects of the drugs are evaluated on the different stages of cell division identified by flow cytometry (G0/G1, S & G2M). Thus, anti-cancer agents exhibiting cell cycle arrest capabilities will stop the cells proliferating and hence result in elevated levels of a particular phase(s). Following pre-treatment of the test cells with a compound, the cells are incubated with a mixture of a fluorescent DNA stain (e.g., propidium iodide), RNase (to remove RNA) and a mild detergent (e.g., Triton X-100) to facilitate staining of the DNA in each cell. The amount of specific fluorescence is proportional to the amount of DNA in each cell. Cells are treated for 24, 48, or 72 h with the vehicle (control) or with the compounds of the invention at specified concentrations, washed with phosphate buffered saline (PBS), stained at 4° C. overnight with, e.g., PI (about 50 mg/ml in 0.1% sodium citrate and 0.1% Triton X-100), and submitted to FACS analysis on a Beckton-Dickinson. Several computer programs are available to analyze the cell cycle distribution so obtained (e.g., Modifit's program by Becton Dickinson).

Flow cytometry can also be used to determine the effect of the drugs on apoptosis induction as described, e.g., in Barthomeuf et al. (2008) Phytomedicine 15(1-2):103-11. The number of early apoptotic cells can be determined with, e.g., the annexin V-PI detection kit (BD Biosciences), as described by Tan et al. (2005) were cells are treated for about 48 h with the compounds of the invention, washed with DMEM and incubated in the dark at about 4° C. with Annexin V$^{FITC}$ and PI for about 15 min before dual-color flow cytometry. Early apoptotic cells may be Annexin V$^{FITC}$ positive and PI negative.

What is claimed is:

1. A compound of Formulas (Ia), or stereoisomeric forms thereof,

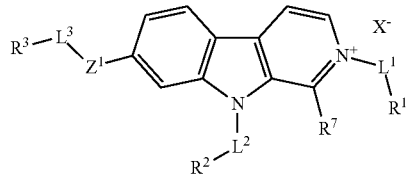
(Ia)

wherein
Z$^1$ is —O—,
R$^1$-L$^1$- is C$_{1-6}$alkyl optionally substituted with hydroxy, or R$^1$-L$^1$- is benzyl optionally substituted with fluoro;
R$^2$-L$^2$- is n-propyl or 3-methyl-butyl;
R$^3$-L$^3$- is C$_{1-6}$alkyl or benzyl;
R$^7$ is C$_{1-6}$alkyl;
X$^-$ is an organic or inorganic anion;
or pharmaceutically acceptable addition salts, hydrates or solvates thereof.

2. The compound according to claim 1, wherein R$^1$-L$^1$- is methyl, ethyl, propyl, butyl, pentyl or hexyl, each group being optionally substituted with hydroxy.

3. The compound according to claim 1, wherein R$^3$-L$^3$ is propyl or 3-methyl-butyl.

4. The compound according to claim 1, wherein R$^7$ is methyl or ethyl.

5. A compound of the general formula (VIIa), or stereoisomeric forms thereof,

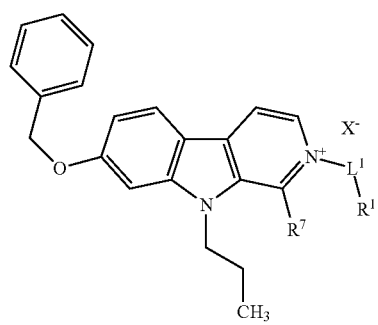
(VIIa)

wherein
R$^7$, R$^1$, L$^1$ and X$^-$ have their respective meanings as set forth in claim 1;
or the pharmaceutically acceptable addition salts, hydrates or solvates thereof.

6. The compound according to claim 1, selected from the following compounds:

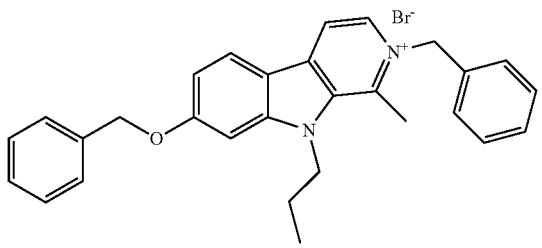

CV34

1-methyl-2-benzyl-7-benzyloxy-9-propyl-β-carbolin-2-ium bromide

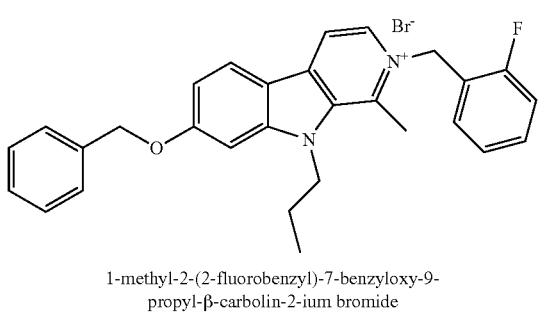

CV35

1-methyl-2-(2-fluorobenzyl)-7-benzyloxy-9-propyl-β-carbolin-2-ium bromide

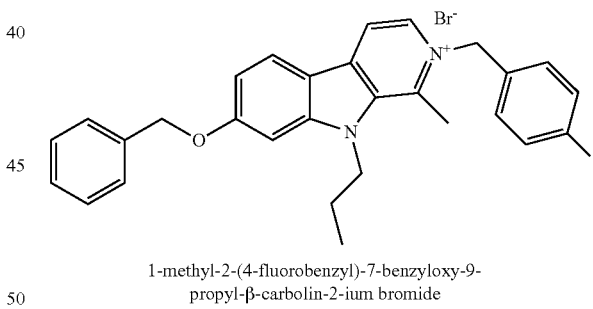

CV36

1-methyl-2-(4-fluorobenzyl)-7-benzyloxy-9-propyl-β-carbolin-2-ium bromide

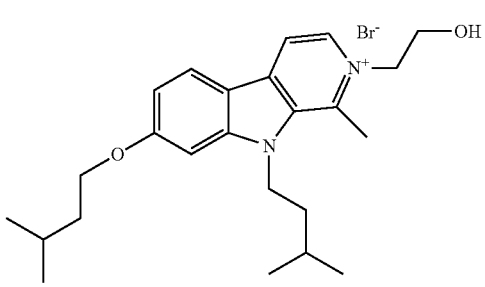

PL11

1-methyl-2-hydroxyethyl-7-(3-methylbutyloxy)-9-(3-methylbutyl)-β-carbolin-2-ium bromide

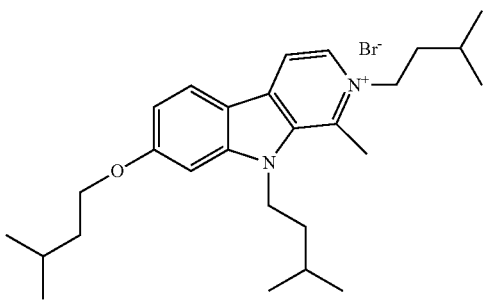

1-methyl-2-(3-methylbutyl)-7-(3-methylbutyloxy)-9-(3-methylbutyl)-β-carbolin-2-ium bromide

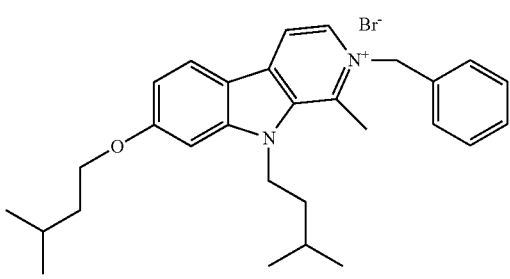

1-methyl-2-benzyl-7-(3-methylbutyloxy)-9-(3-methylbutyl)-β-carbolin-2-ium bromide 7. A pharmaceutical composition comprising the compound according to claim 1, the stereoisomeric forms thereof or the pharmaceutically acceptable addition salts, hydrates or solvates thereof, and one or more pharmaceutically acceptable excipients.

8. The compound according to claim 1, the stereoisomeric forms thereof or the pharmaceutically acceptable addition salts, hydrates or solvates thereof, optionally in combination with one or more pharmaceutically acceptable excipients, for use as a medicament.

9. A method for treating a proliferative disorder in a subject in need of such treatment, comprising administering to said subject a therapeutically effective amount of the compound according to claim 1, the stereoisomeric forms thereof or the pharmaceutically acceptable addition salts, hydrates or solvates thereof, optionally in combination with one or more pharmaceutically acceptable excipients.

10. The method according to claim 9, wherein the proliferative disorder is a cancer selected from the group of: non-small cell lung cancer, prostate cancer, breast cancer, glioma, colon cancer and melanoma.

11. The method according to claim 9, wherein the proliferative disorder is an apoptosis-resistant tumour or cancer.

12. The compound according to claim 1, wherein $R^1$-$L^1$- is ethyl, 2-hydroxyethyl, propyl, butyl, pentyl, 3-methyl-butyl, or hexyl.

13. The compound according to claim 1, wherein $R^7$ is methyl.

14. The compound according to claim 1, wherein $X^-$ is halide.

15. The compound according to claim 1, wherein $X^-$ is bromide.

16. The compound according to claim 5, wherein $R^1$-$L^1$- is benzyl, 2-fluoro-phen-1-ylmethyl, or 4-fluoro-phen-1-ylmethyl; $R^7$ is methyl; and $X^-$ is halide.

17. The compound according to claim 16, wherein $X^-$ is bromide.

* * * * *